US008829170B2

(12) United States Patent
Dale et al.

(10) Patent No.: US 8,829,170 B2
(45) Date of Patent: *Sep. 9, 2014

(54) CONSTRUCT CAPABLE OF RELEASE IN CLOSED CIRCULAR FORM FROM A LARGER NUCLEOTIDE SEQUENCE PERMITTING SITE SPECIFIC EXPRESSION AND/OR DEVELOPMENTALLY REGULATED EXPRESSION OF SELECTED GENETIC SEQUENCES

(75) Inventors: James Langham Dale, Anstead (AU); Benjamin Dugdale, Milton (AU); Greg John Hafner, Carina (AU); Scott Richard Hermann, Strathpine (AU); Douglas Kenneth Becker, Alderley (AU); Robert Maxwell Harding, Highgate Hill (AU); Srimek Chowpongpang, Samut (TH)

(73) Assignee: Queensland University of Technology, Brisbane, Queensland (AU)

( * ) Notice: Subject to any disclaimer, the term of this patent is extended or adjusted under 35 U.S.C. 154(b) by 488 days.

This patent is subject to a terminal disclaimer.

(21) Appl. No.: 12/948,005

(22) Filed: Nov. 17, 2010

(65) Prior Publication Data

US 2011/0119782 A1 May 19, 2011

Related U.S. Application Data

(63) Continuation of application No. 10/168,653, filed as application No. PCT/AU01/00349 on Mar. 28, 2001, now Pat. No. 7,863,430.

(30) Foreign Application Priority Data

Mar. 28, 2000 (AU) .............................................. 6516
Oct. 27, 2000 (AU) .............................................. 1081

(51) Int. Cl.
*C07H 21/04* (2006.01)

(52) U.S. Cl.
USPC ...................................................... 536/23.1

(58) Field of Classification Search
None
See application file for complete search history.

(56) References Cited

U.S. PATENT DOCUMENTS 6,077,992 A 6/2000 Yadav

FOREIGN PATENT DOCUMENTS

WO WO 00/17365 3/2000

OTHER PUBLICATIONS

Atkinson, R. G., et al., "Post-Transcriptional Silencing of Chalcone Synthase in Petunia Using a Geminivirus-Based Episomal Vector," *The Plant Journal*, 1998, pp. 593-604, vol. 15 (5).

Behjatnia, et al., *Nucleic Acids Research*, 1998, vol. 26, pp. 925-931.
Genbank Accession No. M81103.
Hafner, G. J., et al., "Nicking and Joining Activity of Banana Bunchy Top Virus Replication Protein in vitro," Journal of General Virology, 1997, pp. 1795-1799, vol. 78, Great Britain.
Im, et al., *J. Virol.*, 1989, vol. 63, pp. 3095-3104, abstract.
International Search Report from corresponding International Application PCT/AU01/00349 dated May 24, 2001.
Kilby, N. J., et al., "Site-Specific Recombinases: Tools for Genome Engineering," *TIG*, 1993, pp. 413-421, vol. 9 (12).
Laufs, et al., *Biochimie*, 1995, vol. 77, pp. 765-773.
Lazarowitz, S. G., "Geminiviruses: Genome Structure and Gene Function," *Critical Reviews in Plant Sciences*, 1992, pp. 327-349, vol. 11 (4).
Liu, et al., *Journal of General Virology*, 1990, vol. 80, pp. 501-506.
Mourgues, et al., *Trends Biotechnol.*, 1998, vol. 16, pp. 203-210.
Needham, P. D., et al., "GUS Expression Patterns from a Tobacco Yellow Dwarf Virus-Based Episomal Vector," *Plant Cell Reports*, 1998, pp. 631-639, vol. 17.
Onouchi, H., et al., "Operation of an Efficient Site-Specific Recombination System of *Zygosaccharomyces rouxii* in Tobacco Cells," *Nucleic Acids Research*, 1991, pp. 6373-6378, vol. 19 (23).
Palmer, K. E., and E. P Rybicki, "The Molecular Biology of Mastreviruses," *Advances in Virus Research*, 1998, pp. 183-234, vol. 50.
Ryan, et al., *J. Virol.*, 1996, vol. 70, pp. 1542-1553, abstract.
Satoh, W., et al., "Site Specific Integration of an Adeno-Associated Virus Vector Plasmid Mediated by Regulated Expression of Rep based on Cre-*loxP* recombination." Journal of Virology, Nov. 2000, pp. 10631-10638, vol. 74 No. 22, American Society for Microbiology.
Wu, et al., *Archives of Biochemistry*, 2001, vol. 389, pp. 271-277.

*Primary Examiner* — Ileana Popa
(74) *Attorney, Agent, or Firm* — Alston & Bird LLP

(57) ABSTRACT

The present invention relates generally to constructs and in particular genetic constructs comprising polynucleotide sequences capable of release in covalently closed, circular form from a larger nucleotide sequence such as, but not limited to, a genome of a eukaryotic cell. Preferably, once released, a polynucleotide sequence is reconstituted in a form which permits expression of the polynucleotide sequence. In one embodiment, the reconstituted polynucleotide sequence comprises a coding sequence with all or part of an extraneous nucleotide such as, but not limited to, an intronic sequence or other splice signal inserted therein. Expression and in particular transcription of the coding sequence involves splicing out the extraneous sequence. The release and circularization is generally in response to a stimulus such as a protein-mediated stimulus. More particularly, the protein is a viral or prokaryotic or eukaryotic derived protein or developmentally and/or tissue specific regulated protein.

Figure 1:
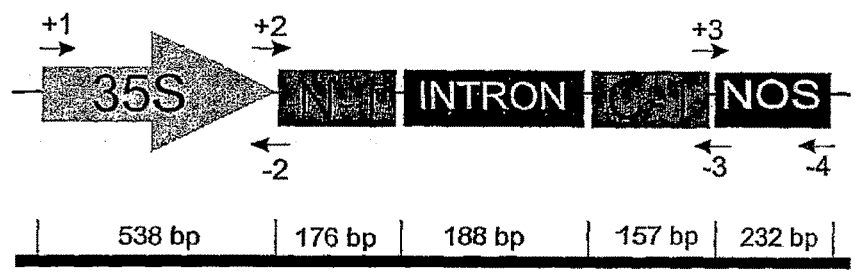

8 Claims, 21 Drawing Sheets pTBN pTBN6 pRTBN6 pRTBN1 pGI pRGI6 pRGI1

Expression and accumulation of Human serum albumin (HSA) *in planta*

SEQUENCE LISTING

```
<160> NUMBER OF SEQ ID NOS: 73

<210> SEQ ID NO 1
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 1
aagcttcatg gagtcaaaga                                                   20

<210> SEQ ID NO 2
<211> LENGTH: 29
<212> TYPE: DNA
<213> ORGANISM: Artificial Sequence
<220> FEATURE:
<223> OTHER INFORMATION: Synthetic oligonucleotide

<400> SEQUENCE: 2
tcatttggag aggatccatg gcacaggtt                                         29

<210> SEQ ID NO 3
<211> LENGTH: 29
<212> TYPE: DNA
<213> ORGANISM: Artificial Sequence
<220> FEATURE:
<223> OTHER INFORMATION: Synthetic oligonucleotide

<400> SEQUENCE: 3
aacctgtgcc atggatcctc tccaaatga                                         29

<210> SEQ ID NO 4
<211> LENGTH: 29
<212> TYPE: DNA
<213> ORGANISM: Artificial Sequence
<220> FEATURE:
<223> OTHER INFORMATION: Synthetic oligonucleotide

<400> SEQUENCE: 4
aaaatcagat aagagctcga tcgttcaaa                                         29

<210> SEQ ID NO 5
<211> LENGTH: 29
<212> TYPE: DNA
<213> ORGANISM: Artificial Sequence
```

```
<220> FEATURE:
<223> OTHER INFORMATION: Synthetic oligonucleotide

<400> SEQUENCE: 5
tttgaacgat cgagctctta tctgatttt                                    29

<210> SEQ ID NO 6
<211> LENGTH: 23
<212> TYPE: DNA
<213> ORGANISM: Artificial Sequence
<220> FEATURE:
<223> OTHER INFORMATION: Synthetic oligonucleotide

<400> SEQUENCE: 6
aagcttttcg ccattcaggc tgc                                          23

<210> SEQ ID NO 7
<211> LENGTH: 28
<212> TYPE: DNA
<213> ORGANISM: Artificial Sequence
<220> FEATURE:
<223> OTHER INFORMATION: Synthetic oligonucleotide

<400> SEQUENCE: 7
tatcattaat tagtaagttg tgctgtaa                                     28

<210> SEQ ID NO 8
<211> LENGTH: 28
<212> TYPE: DNA
<213> ORGANISM: Artificial Sequence
<220> FEATURE:
<223> OTHER INFORMATION: Synthetic oligonucleotide

<400> SEQUENCE: 8
ttacagcaca acttactaat taatgata                                     28

<210> SEQ ID NO 9
<211> LENGTH: 28
<212> TYPE: DNA
<213> ORGANISM: Artificial Sequence
<220> FEATURE:
<223> OTHER INFORMATION: Synthetic oligonucleotide

<400> SEQUENCE: 9
ggaaggcaga agcgagtaat ataatatt                                     28

<210> SEQ ID NO 10
<211> LENGTH: 28
<212> TYPE: DNA
<213> ORGANISM: Artificial Sequence
<220> FEATURE:
<223> OTHER INFORMATION: Synthetic oligonucleotide

<400> SEQUENCE: 10
aatattatat tactcgcttc tgccttcc                                     28

<210> SEQ ID NO 11
<211> LENGTH: 29
<212> TYPE: DNA
<213> ORGANISM: Artificial Sequence
<220> FEATURE:
<223> OTHER INFORMATION: Synthetic oligonucleotide

<400> SEQUENCE: 11
atcattaatt agtcacacta tgacaaaag                                    29
```

```
<210> SEQ ID NO 12
<211> LENGTH: 29
<212> TYPE: DNA
<213> ORGANISM: Artificial Sequence
<220> FEATURE:
<223> OTHER INFORMATION: Synthetic oligonucleotide

<400> SEQUENCE: 12
ttgtcatagt gtgactaatt aatgataat                                   29

<210> SEQ ID NO 13
<211> LENGTH: 29
<212> TYPE: DNA
<213> ORGANISM: Artificial Sequence
<220> FEATURE:
<223> OTHER INFORMATION: Synthetic oligonucleotide

<400> SEQUENCE: 13
gacatttgca tcagtaatat aatatttca                                   29

<210> SEQ ID NO 14
<211> LENGTH: 29
<212> TYPE: DNA
<213> ORGANISM: Artificial Sequence
<220> FEATURE:
<223> OTHER INFORMATION: Synthetic oligonucleotide

<400> SEQUENCE: 14
aatattatat tactgatgca aatgtcccg                                   29

<210> SEQ ID NO 15
<211> LENGTH: 29
<212> TYPE: DNA
<213> ORGANISM: Artificial Sequence
<220> FEATURE:
<223> OTHER INFORMATION: Synthetic oligonucleotide

<400> SEQUENCE: 15
tcagataaga gctcagtaac agcaacaac                                   29

<210> SEQ ID NO 16
<211> LENGTH: 29
<212> TYPE: DNA
<213> ORGANISM: Artificial Sequence
<220> FEATURE:
<223> OTHER INFORMATION: Synthetic oligonucleotide

<400> SEQUENCE: 16
gctgttactg agctcttatc tgatctttg                                   29

<210> SEQ ID NO 17
<211> LENGTH: 23
<212> TYPE: DNA
<213> ORGANISM: Artificial Sequence
<220> FEATURE:
<223> OTHER INFORMATION: Synthetic oligonucleotide

<400> SEQUENCE: 17
aagcttattt cccaaatata cgt                                         23

<210> SEQ ID NO 18
<211> LENGTH: 21
<212> TYPE: DNA
<213> ORGANISM: Artificial Sequence
<220> FEATURE:
<223> OTHER INFORMATION: Primer
```

```
<400> SEQUENCE: 18
ggatccgcac aggttatcaa c                                              21

<210> SEQ ID NO 19
<211> LENGTH: 41
<212> TYPE: DNA
<213> ORGANISM: Artificial Sequence
<220> FEATURE:
<223> OTHER INFORMATION: Primer

<400> SEQUENCE: 19
gctcttcctg caggcggccg cattaaggct caagtaccgt a                        41

<210> SEQ ID NO 20
<211> LENGTH: 41
<212> TYPE: DNA
<213> ORGANISM: Artificial Sequence
<220> FEATURE:
<223> OTHER INFORMATION: Primer

<400> SEQUENCE: 20
gctcttcgtc gacgaattca ttttcaactt tgggatgtca c                        41

<210> SEQ ID NO 21
<211> LENGTH: 24
<212> TYPE: DNA
<213> ORGANISM: Artificial Sequence
<220> FEATURE:
<223> OTHER INFORMATION: Primer

<400> SEQUENCE: 21
gaattccatg gagtcaaaga ttca                                           24

<210> SEQ ID NO 22
<211> LENGTH: 32
<212> TYPE: DNA
<213> ORGANISM: Artificial Sequence
<220> FEATURE:
<223> OTHER INFORMATION: Primer

<400> SEQUENCE: 22
gcccgctgca gagtttaaag aaagatcaaa gc                                  32

<210> SEQ ID NO 23
<211> LENGTH: 34
<212> TYPE: DNA
<213> ORGANISM: Artificial Sequence
<220> FEATURE:
<223> OTHER INFORMATION: Primer

<400> SEQUENCE: 23
gccccggtcg acgatctatt ttttaattga ttgg                                34

<210> SEQ ID NO 24
<211> LENGTH: 33
<212> TYPE: DNA
<213> ORGANISM: Artificial Sequence
<220> FEATURE:
<223> OTHER INFORMATION: Primer

<400> SEQUENCE: 24
ttcgagctgg tcacctgtaa ttcacacgtg gtg                                 33

<210> SEQ ID NO 25
```

```
<211> LENGTH: 18
<212> TYPE: DNA
<213> ORGANISM: Artificial Sequence
<220> FEATURE:
<223> OTHER INFORMATION: Primer

<400> SEQUENCE: 25
ccatggtaga tctgaggg                                                    18

<210> SEQ ID NO 26
<211> LENGTH: 25
<212> TYPE: DNA
<213> ORGANISM: Artificial Sequence
<220> FEATURE:
<223> OTHER INFORMATION: Primer

<400> SEQUENCE: 26
tacgtacact tttcccggca ataac                                            25

<210> SEQ ID NO 27
<211> LENGTH: 23
<212> TYPE: DNA
<213> ORGANISM: Artificial Sequence
<220> FEATURE:
<223> OTHER INFORMATION: Primer

<400> SEQUENCE: 27
gtaacgcgct ttcccaccaa cgc                                              23

<210> SEQ ID NO 28
<211> LENGTH: 26
<212> TYPE: DNA
<213> ORGANISM: Artificial Sequence
<220> FEATURE:
<223> OTHER INFORMATION: Primer

<400> SEQUENCE: 28
ctcgagatta aggctcaagt accgta                                           26

<210> SEQ ID NO 29
<211> LENGTH: 21
<212> TYPE: DNA
<213> ORGANISM: Artificial Sequence
<220> FEATURE:
<223> OTHER INFORMATION: Primer

<400> SEQUENCE: 29
agtttaaaga aagatcaaag c                                                21

<210> SEQ ID NO 30
<211> LENGTH: 20
<212> TYPE: DNA
<213> ORGANISM: Artificial Sequence
<220> FEATURE:
<223> OTHER INFORMATION: Primer

<400> SEQUENCE: 30
aattaaccct cactaaaggg                                                  20

<210> SEQ ID NO 31
<211> LENGTH: 32
<212> TYPE: DNA
<213> ORGANISM: Artificial Sequence
<220> FEATURE:
<223> OTHER INFORMATION: Primer

<400> SEQUENCE: 31
```

-continued

```
gcatgcaaga gttggcggta gattccgcat gt                                    32

<210> SEQ ID NO 32
<211> LENGTH: 35
<212> TYPE: DNA
<213> ORGANISM: Artificial Sequence
<220> FEATURE:
<223> OTHER INFORMATION: Primer

<400> SEQUENCE: 32
gctcttcgcg gccgcgctcc tgaatcgtcg agtca                                 35

<210> SEQ ID NO 33
<211> LENGTH: 22
<212> TYPE: DNA
<213> ORGANISM: Artificial Sequence
<220> FEATURE:
<223> OTHER INFORMATION: Primer

<400> SEQUENCE: 33
tttaaacgtt tagggttag ca                                                22

<210> SEQ ID NO 34
<211> LENGTH: 18
<212> TYPE: DNA
<213> ORGANISM: Artificial Sequence
<220> FEATURE:
<223> OTHER INFORMATION: Primer

<400> SEQUENCE: 34
tcagtgactc gacgattc                                                    18

<210> SEQ ID NO 35
<211> LENGTH: 18
<212> TYPE: DNA
<213> ORGANISM: Artificial Sequence
<220> FEATURE:
<223> OTHER INFORMATION: Primer

<400> SEQUENCE: 35
ttaatatgcc ttcagccc                                                    18

<210> SEQ ID NO 36
<211> LENGTH: 20
<212> TYPE: DNA
<213> ORGANISM: Artificial Sequence
<220> FEATURE:
<223> OTHER INFORMATION: Primer

<400> SEQUENCE: 36
atgattgaac aagatggatt                                                  20

<210> SEQ ID NO 37
<211> LENGTH: 18
<212> TYPE: DNA
<213> ORGANISM: Artificial Sequence
<220> FEATURE:
<223> OTHER INFORMATION: Primer

<400> SEQUENCE: 37
tgagaagaac tcgtcaag                                                    18

<210> SEQ ID NO 38
<211> LENGTH: 25
<212> TYPE: DNA
```

```
<213> ORGANISM: Artificial Sequence
<220> FEATURE:
<223> OTHER INFORMATION: Primer

<400> SEQUENCE: 38
gttattgccg ggaaaagtgt acgta                                        25

<210> SEQ ID NO 39
<211> LENGTH: 25
<212> TYPE: DNA
<213> ORGANISM: Artificial Sequence
<220> FEATURE:
<223> OTHER INFORMATION: Primer

<400> SEQUENCE: 39
ctagcttgtt tgcctccctg ctgcg                                        25

<210> SEQ ID NO 40
<211> LENGTH: 34
<212> TYPE: DNA
<213> ORGANISM: Artificial Sequence
<220> FEATURE:
<223> OTHER INFORMATION: Primer

<400> SEQUENCE: 40
ggatccatgg cacaggttat caacacgttt gacg                              34

<210> SEQ ID NO 41
<211> LENGTH: 28
<212> TYPE: DNA
<213> ORGANISM: Artificial Sequence
<220> FEATURE:
<223> OTHER INFORMATION: Primer

<400> SEQUENCE: 41
ctagagttat ctgatttttg taaaggtc                                     28

<210> SEQ ID NO 42
<211> LENGTH: 31
<212> TYPE: DNA
<213> ORGANISM: Artificial Sequence
<220> FEATURE:
<223> OTHER INFORMATION: Primer

<400> SEQUENCE: 42
ggatccgcac aggttatcaa cacgtttgac g                                 31

<210> SEQ ID NO 43
<211> LENGTH: 25
<212> TYPE: DNA
<213> ORGANISM: Artificial Sequence
<220> FEATURE:
<223> OTHER INFORMATION: Primer

<400> SEQUENCE: 43
atggcgggcc ggtataaggg tttgg                                        25

<210> SEQ ID NO 44
<211> LENGTH: 26
<212> TYPE: DNA
<213> ORGANISM: Artificial Sequence
<220> FEATURE:
<223> OTHER INFORMATION: Primer

<400> SEQUENCE: 44
ttattgattg ccaactgatt tgaaat                                       26
```

<210> SEQ ID NO 45
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 45
aagcttcatg gagtcaaaga                                          20

<210> SEQ ID NO 46
<211> LENGTH: 27
<212> TYPE: DNA
<213> ORGANISM: Artificial Sequence
<220> FEATURE:
<223> OTHER INFORMATION: Synthetic oligonucleotide

<400> SEQUENCE: 46
ggatccatga gtaaaggaga agaactt                                  27

<210> SEQ ID NO 47
<211> LENGTH: 29
<212> TYPE: DNA
<213> ORGANISM: Artificial Sequence
<220> FEATURE:
<223> OTHER INFORMATION: Synthetic oligonucleotide

<400> SEQUENCE: 47
aagtcaagtt tgaggtaagt ttctgcttc                                29

<210> SEQ ID NO 48
<211> LENGTH: 29
<212> TYPE: DNA
<213> ORGANISM: Artificial Sequence
<220> FEATURE:
<223> OTHER INFORMATION: Synthetic oligonucleotide

<400> SEQUENCE: 48
gaagcagaaa cttacctcaa acttgactt                                29

<210> SEQ ID NO 49
<211> LENGTH: 29
<212> TYPE: DNA
<213> ORGANISM: Artificial Sequence
<220> FEATURE:
<223> OTHER INFORMATION: Synthetic oligonucleotide

<400> SEQUENCE: 49
ttgttgatgt gcagggagac accctcgtc                                29

<210> SEQ ID NO 50
<211> LENGTH: 29
<212> TYPE: DNA
<213> ORGANISM: Artificial Sequence
<220> FEATURE:
<223> OTHER INFORMATION: Synthetic oligonucleotide

<400> SEQUENCE: 50
gacgagggtg tctccctgca catcaacaa                                29

<210> SEQ ID NO 51
<211> LENGTH: 27
<212> TYPE: DNA
<213> ORGANISM: Artificial Sequence
<220> FEATURE:

<223> OTHER INFORMATION: Synthetic oligonucleotide

<400> SEQUENCE: 51
gagctcttat ttgtatagtt catccat                                      27

<210> SEQ ID NO 52
<211> LENGTH: 23
<212> TYPE: DNA
<213> ORGANISM: Artificial Sequence
<220> FEATURE:
<223> OTHER INFORMATION: Synthetic oligonucleotide

<400> SEQUENCE: 52
aagcttttcg ccattcaggc tgc                                          23

<210> SEQ ID NO 53
<211> LENGTH: 28
<212> TYPE: DNA
<213> ORGANISM: Artificial Sequence
<220> FEATURE:
<223> OTHER INFORMATION: Synthetic oligonucleotide

<400> SEQUENCE: 53
tatcattaat tagtaagttg tgctgtaa                                     28

<210> SEQ ID NO 54
<211> LENGTH: 28
<212> TYPE: DNA
<213> ORGANISM: Artificial Sequence
<220> FEATURE:
<223> OTHER INFORMATION: Synthetic oligonucleotide

<400> SEQUENCE: 54
aatattatat tactcgcttc tgccttcc                                     28

<210> SEQ ID NO 55
<211> LENGTH: 29
<212> TYPE: DNA
<213> ORGANISM: Artificial Sequence
<220> FEATURE:
<223> OTHER INFORMATION: Synthetic oligonucleotide

<400> SEQUENCE: 55
atcattaatt agtcacacta tgacaaaag                                    29

<210> SEQ ID NO 56
<211> LENGTH: 30
<212> TYPE: DNA
<213> ORGANISM: Artificial Sequence
<220> FEATURE:
<223> OTHER INFORMATION: Synthetic oligonucleotide

<400> SEQUENCE: 56
aatattatat tactgatgca aatgtccccg                                   30

<210> SEQ ID NO 57
<211> LENGTH: 30
<212> TYPE: DNA
<213> ORGANISM: Artificial Sequence
<220> FEATURE:
<223> OTHER INFORMATION: Primer

<400> SEQUENCE: 57
ccatggatct cattctcctt caacaaggcg                                   30

```
<210> SEQ ID NO 58
<211> LENGTH: 33
<212> TYPE: DNA
<213> ORGANISM: Artificial Sequence
<220> FEATURE:
<223> OTHER INFORMATION: Primer

<400> SEQUENCE: 58
ccatggtttc aacttcttct tttgtgttat ttg                              33

<210> SEQ ID NO 59
<211> LENGTH: 27
<212> TYPE: DNA
<213> ORGANISM: Artificial Sequence
<220> FEATURE:
<223> OTHER INFORMATION: Primer

<400> SEQUENCE: 59
gaattcaggg gtaagtttgc aaatatc                                     27

<210> SEQ ID NO 60
<211> LENGTH: 26
<212> TYPE: DNA
<213> ORGANISM: Artificial Sequence
<220> FEATURE:
<223> OTHER INFORMATION: Primer

<400> SEQUENCE: 60
cgaggttgtg ccagtcgagc attgcc                                      26

<210> SEQ ID NO 61
<211> LENGTH: 30
<212> TYPE: DNA
<213> ORGANISM: Artificial Sequence
<220> FEATURE:
<223> OTHER INFORMATION: Primer

<400> SEQUENCE: 61
ccatggtttg aggcgaggtg ataggattgg                                  30

<210> SEQ ID NO 62
<211> LENGTH: 30
<212> TYPE: DNA
<213> ORGANISM: Artificial Sequence
<220> FEATURE:
<223> OTHER INFORMATION: Primer

<400> SEQUENCE: 62
ccatggagat agagtcttta gagcagtttc                                  30

<210> SEQ ID NO 63
<211> LENGTH: 30
<212> TYPE: DNA
<213> ORGANISM: Artificial Sequence
<220> FEATURE:
<223> OTHER INFORMATION: Primer

<400> SEQUENCE: 63
ggatcctatt gtgttcctgc atcgacctta                                  30

<210> SEQ ID NO 64
<211> LENGTH: 34
<212> TYPE: DNA
<213> ORGANISM: Artificial Sequence
<220> FEATURE:
<223> OTHER INFORMATION: Primer
```

-continued

```
<400> SEQUENCE: 64
ccatgggcat gcacgcttct ccagcgtaga agcg                                34

<210> SEQ ID NO 65
<211> LENGTH: 30
<212> TYPE: DNA
<213> ORGANISM: Artificial Sequence
<220> FEATURE:
<223> OTHER INFORMATION: Primer

<400> SEQUENCE: 65
ggatcctcag tttcgcgccc tgagcgccgg                                     30

<210> SEQ ID NO 66
<211> LENGTH: 1294
<212> TYPE: DNA
<213> ORGANISM: Artificial Sequence
<220> FEATURE:
<223> OTHER INFORMATION: Synthetic construct

<400> SEQUENCE: 66
catggagtca aagattcaaa tagaggacct aacagaactc gccgtaaaga ctggcgaaca    60
gttcatacag agtctcttac gactcaatga caagaagaaa tcttcgtca acatggtgga   120 gcacgacaca cttgtctact ccaaaaatat caaagataca gtctcagaag accaaagggc   180
aattgagact tttcaacaaa gggtaatatc cggaaacctc ctcggattcc attgcccagc   240
tatctgtcac tttattgtga agatagtgga aaggaaggt ggctcctaca aatgccatca   300
ttgcgataaa ggaaaggcca tcgttgaaga tgcctctgcc gacagtggtc ccaaagatgg   360
acccccaccc acgaggagca tcgtggaaaa agaagacgtt ccaaccacgt cttcaaagca   420
agtggattga tgtgatatct ccactgacgt aagggatgac gcacaatccc actatccttc   480
gcaagaccct tcctctatat aaggaagttc atttcatttg gagaggatcc catggcacag   540
gttatcaaca cgtttgacgg ggttgcggat tatcttcaga catatcataa gctacctgat   600
aattacatta caaaatcaga agcacaagcc ctcggctggg tggcatcaaa agggaacctt   660
gcagacgtcg ctccggggaa aagcatcggc ggagacatct tctcgaacag gtaagtttct   720
gcttctacct ttgatatata tataataatt atcattaatt agtagtaata taatatttca   780 aatattttt tcaaaataaa agaatgtagt atatagcaat tgcttttctg tagtttataa   840
gtgtgtatat tttaatttat aacttttcta atatatgacc aaaatttgtt gatgtgcagg   900
gagggcaagc tcccgggcaa aagcggacga acatggcgtg aagcggatat taactataca   960
tcaggcttca gaaattcaga ccggattctt tactcaagcg actggctgat ttacaaaaca  1020
acggaccatt atcagacctt tacaaaaatc agataactct agagtttctt aagattgaat  1080
cctgttgccg gtcttgcgat gattatcata taatttctgt tgaattacgt taagcatgta  1140
ataattaaca tgtaatgcat gacgttattt atgagatggg ttttatgat tagagtcccg  1200 caattataca tttaatacgc gatagaaaac aaaatatagc gcgcaaacta ggataaatta  1260
tcgcgcgcgg tgtcatctat gttactagat cggg                              1294

<210> SEQ ID NO 67
<211> LENGTH: 2708
<212> TYPE: DNA
<213> ORGANISM: Artificial Sequence
<220> FEATURE:
<223> OTHER INFORMATION: Synthetic construct

<400> SEQUENCE: 67
```

```
gcgaagttgt gctgtaatgt taattaataa aacgtatatt tgggaaattg atagttgtat      60
aaaacataca acacactatg aaatacaaga cgctatgaca aatgtacggg tatctgaatg     120
agttttagta tcgcttaagg gccgcaggcc cgttaaaaat aataatcgaa ttataaacgt     180
tagataataa tcagagatag gtgatcagat aatataaaca taaacgaagt atatgccggt     240
acaataataa aataagtaat aacaaaaaaa atatgtatac taatctctga ttggttcagg     300
agaaaggccc accaactaaa aggtggggag aatgtcccga tgacgtaagc acggggggact     360 attattaccc cccgtgctcg ggacgggaca tgacgtcagc aaggattata atgggctttt     420
tattagccca tttattgaat tgggccgggt tttgtcattt tacaaaagcc cggtccagga     480
taagtataat gtcacgtgcc gaattaaaag gttgcttcgc cacgaagaaa cctaatttga     540
ggttgcgtat tcaatacgct accgaatatc tattaatatg tgagtctctg ccgaaaaaaa     600
tcagagcgaa agcggaaggc agaagcgagt aatataatat ttcaaatatt tttttcaaaa     660
taaaagaatg tagtatatag caattgcttt tctgtagttt ataagtgtgt atattttaat     720
ttataacttt tctaatatat gaccaaaatt tgttgatgtg cagggagggc aagctcccgg     780
gcaaaagcgg acgaacatgg cgtgaagcgg atattaacta tacatcaggc ttcagaaatt     840
cagaccggat tctttactca agcgactggc tgatttacaa acaacggac cattatcaga     900 cctttacaaa aatcagataa gagctcgttt cttaagattg aatcctgttg ccggtcttgc     960
gatgattatc atataaatttc tgttgaatta cgttaagcat gtaataatta acatgtaatg    1020
catgacgtta tttatgagat gggtttttat gattagagtc ccgcaattat acatttaata    1080
cgcgatagaa aacaaaatat agcgcgcaaa ctaggataaa ttatcgcgcg cggtgtcatc    1140
tatgttacta gatcgggaa ttcactggcc gtcgttttac aacgtcgtga ctggaaaaac    1200
cctggcgtta cccaacttaa tcgccttgca gcacatcccc ctttcgccag ctggcgtaat    1260
agcgaagagg cccgcaccga tcgcccttcc caacagttgc gcagcctgaa tggcgaaaag    1320
cttcatggag tcaaagattc aaatagagga cctaacagaa ctcgccgtaa agactggcga    1380
acagttcata cagagtctct tacgactcaa tgacaagaag aaaatcttcg tcaacatggt    1440
ggagcacgac acacttgtct actccaaaaa tatcaaagat acagtctcag aagaccaaag    1500
ggcaattgag acttttcaac aaagggtaat atccggaaac ctcctcggat tccattgccc    1560
agctatctgt cactttattg tgaagatagt ggaaaaggaa ggtggctcct acaaatgcca    1620
tcattgcgat aaaggaaagg ccatcgttga agatgcctct gccgacagtg gtcccaaaga    1680 tggacccca cccacgagga gcatcgtgga aaaagaagac gttccaacca cgtcttcaaa    1740
gcaagtggat tgatgtgata tctccactga cgtaagggat gacgcacaat cccactatcc    1800
ttcgcaagac ccttcctcta taaggaag ttcatttcat tggagagga tccatgcaca    1860 ggttatcaac acgtttgacg gggttgcgga ttatcttcag acatatcata agctacctga    1920
taattacatt acaaaatcag aagcacaagc cctcggctgg gtggcatcaa aagggaacct    1980
tgcagacgtc gctccgggga aaagcatcgg cggagacatc ttctcgaaca ggtaagtttc    2040
tgcttctacc tttgatatat atataataat tatcattaat tagtaagttg tgctgtaatg    2100
ttaattaata aaacgtatat ttgggaaatt gatagttgta taaaacatac aacacactat    2160
gaaatacaag acgctatgac aaatgtacgg gtatctgaat gagttttagt atcgcttaag    2220
ggccgcaggc ccgttaaaaa taataatcga attataaacg ttagataata atcagagata    2280
ggtgatcaga taatataaac ataaacgaag tatatgccgg tacaataata aaataagtaa    2340
```

```
taacaaaaaa aatatgtata ctaatctctg attggttcag gagaaaggcc caccaactaa    2400
aaggtgggga gaatgtcccg atgacgtaag cacggggggac tattattacc ccccgtgctc   2460
gggacgggac atgacgtcag caaggattat aatgggcttt ttattagccc atttattgaa    2520
ttgggccggg ttttgtcatt ttacaaaagc ccggtccagg ataagtataa tgtcacgtgc    2580
cgaattaaaa ggttgcttcg ccacgaagaa acctaatttg aggttgcgta ttcaatacgc    2640
taccgaatat ctattaatat gtgagtctct gccgaaaaaa atcagagcga aagcggaagg    2700
cagaagcg                                                             2708
```

<210> SEQ ID NO 68
<211> LENGTH: 1512
<212> TYPE: DNA
<213> ORGANISM: Artificial Sequence
<220> FEATURE:
<223> OTHER INFORMATION: Synthetic construct

<400> SEQUENCE: 68

```
cacactatga caaaagtacg ggtatctgat tgggttatct taacgatcta gggccgtagg     60
cccgtgagca atgaacggcg agatcagatg tcccgagtta gtgcgccacg taagcgctgg    120
ggcttattat tacccccagc gctcgggacg ggacatttgc atcagtaata taatatttca    180
aatatttttt tcaaaataaa agaatgtagt atatagcaat tgcttttctg tagtttataa    240
gtgtgtatat tttaatttat aacttttcta atatatgacc aaaatttgtt gatgtgcagg    300
gagggcaagc tcccgggcaa aagcggacga acatggcgtg aagcggatat taactataca    360
tcaggcttca gaaattcaga ccggattctt tactcaagcg actggctgat ttacaaaaca    420
acggaccatt atcagacctt tacaaagatc agataagagc tcagtaacag caacaactgt    480
aatgaattat gtgatctgaa gtgttatgtt gtttgttcgt taagaatcaa ggaataaaag    540
ttgtgctgta atgttaatta ataaaacgta tatttgggaa ataagcttca tggagtcaaa    600
gattcaaata gaggacctaa cagaactcgc cgtaaagact ggcgaacagt tcatacagag    660
tctcttacga ctcaatgaca agaagaaaat cttcgtcaac atggtggagc acgacacact    720
tgtctactcc aaaaatatca aagatacagt ctcagaagac caaagggcaa ttgagacttt    780
tcaacaaagg gtaatatccg gaaacctcct cggattccat tgcccagcta tctgtcactt    840
tattgtgaag atagtggaaa aggaaggtgg ctccctacaaa tgccatcatt gcgataaagg    900
aaaggccatc gttgaagatg cctctgccga cagtggtccc aaagatggac ccccacccac    960
gaggagcatc gtggaaaaag aagacgttcc aaccacgtct tcaaagcaag tggattgatg   1020
tgatatctcc actgacgtaa gggatgacgc acaatcccac tatccttcgc aagacccttc   1080
ctctatataa ggaagttcat ttcatttgga gaggatccat gcacaggtta tcaacacgtt   1140
tgacggggtt gcggattatc ttcagacata tcataagcta cctgataatt acattacaaa   1200
atcagaagca caagccctcg gctggtggca tcaaaaggg aaccttgcag acgtcgctcc   1260
ggggaaaagc atcggcggag acatcttctc gaacaggtaa gtttctgctt ctacctttga   1320
tatatatata ataattatca ttaattagtc acactatgac aaaagtacgg gtatctgatt   1380
gggttatctt aacgatctag ggccgtaggc ccgtgagcaa tgaacggcga gatcagatgt   1440
cccgagttag tgcgccacgt aagcgctggg gcttattatt accccagcg ctcgggacgg    1500 gacatttgca tc                                                       1512
```

<210> SEQ ID NO 69
<211> LENGTH: 1691

<212> TYPE: DNA
<213> ORGANISM: Artificial Sequence
<220> FEATURE:
<223> OTHER INFORMATION: Synthetic construct

<400> SEQUENCE: 69

| | | | | | |
|---|---|---|---|---|---|
| aagcttcatg | gagtcaaaga | ttcaaataga | ggacctaaca | gaactcgccg | taaagactgg | 60 |
| cgaacagttc | atacagagtc | tcttacgact | caatgacaag | aagaaaatct | tcgtcaacat | 120 |
| ggtggagcac | gacacacttg | tctactccaa | aaatatcaaa | gatacagtct | cagaagacca | 180 |
| aagggcaatt | gagactttc | aacaagggt | aatatccgga | aacctcctcg | gattccattg | 240 |
| cccagctatc | tgtcactta | ttgtgaagat | agtggaaaag | gaaggtggct | cctacaaatg | 300 |
| ccatcattgc | gataaaggaa | aggccatcgt | tgaagatgcc | tctgccgaca | gtggtcccaa | 360 |
| agatggaccc | ccacccacga | ggagcatcgt | ggaaaaagaa | gacgttccaa | ccacgtcttc | 420 |
| aaagcaagtg | gattgatgtg | atatctccac | tgacgtaagg | gatgacgcac | aatcccacta | 480 |
| tccttcgcaa | gacccttcct | ctatataagg | aagttcattt | catttggaga | ggggatccat | 540 |
| gagtaaagga | gaagaacttt | tcactggagt | tgtcccaatt | cttgttgaat | tagatggtga | 600 |
| tgttaatggg | cacaaatttt | ctgtcagtgg | agagggtgaa | ggtgatgcaa | catacggaaa | 660 |
| acttaccctt | aaatttattt | gcactactgg | aaaactacct | gttccgtggc | caacacttgt | 720 |
| cactactttc | tcttatggtg | ttcaatgctt | ttcaagatac | ccagatcata | tgaagcggca | 780 |
| cgacttcttc | aagagcgcca | tgcctgaggg | atacgtgcag | gagaggacca | tcttcttcaa | 840 |
| ggacgacggg | aactacaaga | cacgtgctga | agtcaagttt | gaggtaagtt | tctgcttcta | 900 |
| cctttgatat | atatataata | attatcatta | attagtagta | atataaatatt | tcaaatattt | 960 |
| ttttcaaaat | aaaagaatgt | agtatatagc | aattgctttt | ctgtagttta | taagtgtgta | 1020 |
| tattttaatt | tataacttt | ctaatatatg | accaaaattt | gttgatgtgc | agggagacac | 1080 |
| cctcgtcaac | aggatcgagc | ttaagggaat | cgatttcaag | gaggacggaa | acatcctcgg | 1140 |
| ccacaagttg | gaatacaact | acaactccca | caacgtatac | atcatggccg | acaagcaaaa | 1200 |
| gaacggcatc | aaagccaact | tcaagacccg | ccacaacatc | gaagacggcg | gcgtgcaact | 1260 |
| cgctgatcat | tatcaacaaa | atactccaat | tggcgatggc | cctgtccttt | taccagacaa | 1320 |
| ccattacctg | tccacacaat | ctgcccttc | gaaagatccc | aacgaaaaga | gagaccacat | 1380 |
| ggtccttctt | gagtttgtaa | cagctgctgg | gattacacat | ggcatggatg | aactatacaa | 1440 |
| agctataaga | gctcgtttct | taagattgaa | tcctgttgcc | ggtcttgcga | tgattatcat | 1500 |
| ataatttctg | ttgaattacg | ttaagcatgt | aataattaac | atgtaatgca | tgacgttatt | 1560 |
| tatgagatgg | gttttatga | ttagagtccc | gcaattatac | atttaatacg | cgatagaaaa | 1620 |
| caaaatatag | cgcgcaaact | aggataaatt | atcgcgcgcg | gtgtcatcta | tgttactaga | 1680 |
| tcggggaatt | c | | | | | 1691 |

<210> SEQ ID NO 70
<211> LENGTH: 2315
<212> TYPE: DNA
<213> ORGANISM: Artificial Sequence
<220> FEATURE:
<223> OTHER INFORMATION: Synthetic construct

<400> SEQUENCE: 70

| | | | | | |
|---|---|---|---|---|---|
| aagcttcatg | gagtcaaaga | ttcaaataga | ggacctaaca | gaactcgccg | taaagactgg | 60 |
| cgaacagttc | atacagagtc | tcttacgact | caatgacaag | aagaaaatct | tcgtcaacat | 120 |

```
ggtggagcac gacacacttg tctactccaa aaatatcaaa gatacagtct cagaagacca      180
aagggcaatt gagacttttc aacaaagggt aatatccgga aacctcctcg gattccattg      240
cccagctatc tgtcacttta ttgtgaagat agtggaaaag aaggtggct cctacaaatg       300 ccatcattgc gataaaggaa aggccatcgt tgaagatgcc tctgccgaca gtggtcccaa      360
agatggaccc ccacccacga ggagcatcgt ggaaaaagaa gacgttccaa ccacgtcttc      420
aaagcaagtg gattgatgtg atatctccac tgacgtaagg gatgacgcac aatcccacta      480
tccttcgcaa gacccttcct ctatataagg aagttcattt catttggaga ggggatccat      540
gagtaaagga aagaactttt cactggagt tgtcccaatt cttgttgaat tagatggtga       600
tgttaatggg cacaaatttt ctgtcagtgg agagggtgaa ggtgatgcaa catacggaaa      660 acttacccctt aaatttattt gcactactgg aaaactacct gttccgtggc caacacttgt    720
cactactttc tcttatggtg ttcaatgctt ttcaagatac ccagatcata tgaagcggca      780
cgacttcttc aagagcgcca tgcctgaggg atacgtgcag gagaggacca tcttcttcaa     840
ggacgacggg aactacaaga cacgtgctga agtcaagttt gaggtaagtt tctgcttcta      900
cctttgatat atatataata attatcatta attagtgcga agttgtgctg taatgttaat      960
taataaaacg tatatttggg aaattgatag ttgtataaaa catacaacac actatgaaat     1020
acaagacgct atgacaaatg tacgggtatc tgaatgagtt ttagtatcgc ttaagggccg     1080
caggcccgtt aaaaataata atcgaattat aaacgttaga taataatcag agataggtga     1140
tcagataata taaacataaa cgaagtatat gccggtacaa taataaaata agtaataaca     1200
aaaaaaatat gtatactaat ctctgattgg ttcaggagaa aggcccacca actaaaaggt     1260
ggggagaatg tcccgatgac gtaagcacgg gggactatta ttaccccccg tgctcgggac     1320
gggacatgac gtcagcaagg attataatgg gcttttttatt agcccatta ttgaattggg     1380 ccgggttttg tcattttaca aaagcccggt ccaggataag tataatgtca cgtgccgaat     1440
taaaaggttg cttcgccacg aagaaaccta atttgaggtt gcgtattcaa tacgctaccg     1500
aatatctatt aatatgtgag tctctgccga aaaaaatcag agcgaaagcg gaaggcagaa     1560
gcgagtaata taatatttca aatatttttt tcaaaataaa agaatgtagt atatagcaat     1620
tgcttttctg tagtttataa gtgtgtatat tttaatttat aacttttcta atatatgacc     1680
aaaatttgtt gatgtgcagg gagacaccct cgtcaacagg atcgagctta agggaatcga     1740
tttcaaggag gacggaaaca tcctcggcca caagttggaa tacaactaca actcccacaa     1800
cgtatacatc atggccgaca gcaaaagaa cggcatcaaa gccaacttca gacccgccca     1860
caacatcgaa gacggcggcg tgcaactcgc tgatcattat caacaaaata ctccaattgg     1920
cgatggccct gtccttttac cagacaacca ttacctgtcc acacaatctg cccttttcgaa    1980 agatcccaac gaaaagagag accacatggt ccttcttgag tttgtaacag ctgctgggat     2040
tacacatggc atggatgaac tatacaaagc tagagctcgt ttcttaagat tgaatcctgt     2100
tgccggtctt gcgatgatta tcatataatt tctgttgaat tacgttaagc atgtaataat     2160
taacatgtaa tgcatgacgt tatttatgag atgggttttt atgattagag tcccgcaatt     2220
atacatttaa tacgcgatag aaaacaaaat atagcgcgca aactaggata aattatcgcg     2280
cgcggtgtca tctatgttac tagatcgggg aattc                                2315
```

<210> SEQ ID NO 71
<211> LENGTH: 1851
<212> TYPE: DNA
<213> ORGANISM: Artificial Sequence
<220> FEATURE:
<223> OTHER INFORMATION: Synthetic construct

<400> SEQUENCE: 71

```
aagcttcatg gagtcaaaga ttcaaataga ggacctaaca gaactcgccg taaagactgg      60
cgaacagttc atacagagtc tcttacgact caatgacaag aagaaaatct tcgtcaacat     120
ggtggagcac gacacacttg tctactccaa aaatatcaaa gatacagtct cagaagacca     180
aagggcaatt gagactttc aacaaagggt aatatccgga aacctcctcg gattccattg      240
cccagctatc tgtcacttta ttgtgaagat agtggaaaag gaaggtggct cctacaaatg     300
ccatcattgc gataaaggaa aggccatcgt tgaagatgcc tctgccgaca gtggtcccaa     360
agatggaccc ccacccacga ggagcatcgt ggaaaaagaa gacgttccaa ccacgtcttc     420
aaagcaagtg gattgatgtg atatctccac tgacgtaagg gatgacgcac aatcccacta     480
tccttcgcaa gacccttcct ctatataagg aagttcattt catttggaga ggggatccat     540
gagtaaagga agaaactttt cactggagt tgtcccaatt cttgttgaat tagatggtga      600
tgttaatggg cacaaatttt ctgtcagtgg agagggtgaa ggtgatgcaa catacggaaa     660
acttaccctt aaatttattt gcactactgg aaaactacct gttccgtggc caacacttgt     720
cactactttc tcttatggtg ttcaatgctt ttcaagatac ccagatcata tgaagcggca     780
cgacttcttc aagagcgcca tgcctgaggg atacgtgcag gagaggacca tcttcttcaa     840
ggacgacggg aactacaaga cacgtgctga agtcaagttt gaggtaagtt tctgcttcta     900
cctttgatat atatataata attatcatta attagtcaca ctatgacaaa agtacgggta     960
tctgattggg ttatcttaac gatctagggc cgtaggcccg tgagcaatga acggcgagat    1020
cagatgtccc gagttagtgc gccacgtaag cgctggggct tattattacc cccagcgctc    1080
gggacgggac atttgcatca gtaatataat atttcaaata ttttttttcaa aataaaagaa    1140
tgtagtatat agcaattgct tttctgtagt ttataagtgt gtatatttta atttataact    1200
tttctaatat atgaccaaaa tttgttgatg tgcagggaga caccctcgtc aacaggatcg    1260
agcttaaggg aatcgatttc aaggaggacg gaaacatcct cggccacaag ttggaataca    1320
actacaactc ccacaacgta tacatcatgg ccgacaagca aaagaacggc atcaaagcca    1380
acttcaagac ccgccacaac atcgaagacg gcggcgtgca actcgctgat cattatcaac    1440
aaaatactcc aattggcgat ggccctgtcc ttttaccaga caaccattac ctgtccacac    1500
aatctgccct ttcgaaagat cccaacgaaa agagagacca catggtcctt cttgagtttg    1560
taacagctgc tgggattaca catggcatgg atgaactata caaagctaga gctcgtttct    1620
taagattgaa tcctgttgcc ggtcttgcga tgattatcat ataatttctg ttgaattacg    1680
ttaagcatgt aataattaac atgtaatgca tgacgttatt tatgagatgg gttttttatga    1740
ttagagtccc gcaattatac atttaatacg cgatagaaaa caaaatatag cgcgcaaact    1800
aggataaatt atcgcgcgcg gtgtcatcta tgttactaga tcggggaatt c             1851
```

<210> SEQ ID NO 72
<211> LENGTH: 32
<212> TYPE: DNA
<213> ORGANISM: Artificial Sequence
<220> FEATURE:
<223> OTHER INFORMATION: Primer

<400> SEQUENCE: 72

```
ccatggagat gaagtgggta acctttattt cc                                    32
```

```
<210> SEQ ID NO 73
<211> LENGTH: 30
<212> TYPE: DNA
<213> ORGANISM: Artificial Sequence
<220> FEATURE:
<223> OTHER INFORMATION: Primer

<400> SEQUENCE: 73
ggatccttat aagcctaagg cagcttgact                                    30
```

CONSTRUCT CAPABLE OF RELEASE IN CLOSED CIRCULAR FORM FROM A LARGER NUCLEOTIDE SEQUENCE PERMITTING SITE SPECIFIC EXPRESSION AND/OR DEVELOPMENTALLY REGULATED EXPRESSION OF SELECTED GENETIC SEQUENCES

CROSS REFERENCE TO RELATED APPLICATIONS

This application is a continuation of U.S. application Ser. No. 10/168,653, filed Jun. 20, 2002, which is the U.S. National Stage of International Application No. PCT/AU2001/00349, filed Mar. 28, 2001, which was published by the International Bureau in English on Oct. 4, 2001, and which claims priority from AU PR 1081, filed Oct. 27, 2000, and AU PQ 6516, filed Mar. 28, 2000; all of which are incorporated herein by reference in their entirety.

FIELD OF THE INVENTION

The present invention relates generally to constructs and in particular genetic constructs comprising polynucleotide sequences capable of release in covalently closed, circular form from a larger nucleotide sequence such as, but not limited to, a genome of a eukaryotic cell. Preferably, once released, a polynucleotide sequence is reconstituted in a form which permits expression of the polynucleotide sequence. In one embodiment, the reconstituted polynucleotide sequence comprises a coding sequence with all or part of an extraneous nucleotide such as, but not limited to, intronic sequence or other splice signal inserted therein. Expression and in particular transcription of the coding sequence involves splicing out the extraneous sequence. According to this embodiment, the coding sequence may encode a peptide, polypeptide or protein, an antisense or sense nucleic acid molecule or a ribozyme. In another embodiment, the reconstituted polynucleotide sequence will comprise the extraneous polynucleotide sequence located between a promoter element and coding sequence. In this embodiment, expression of the coding sequence is not substantially adversely affected by the presence of the extraneous sequence. In still a further embodiment, the reconstituted sequence forms an RNA promoter or other regulatory genetic sequence comprising the extraneous sequence which does not affect the function of the promoter. The release and circularization is generally in response to a stimulus such as a protein-mediated stimulus. More particularly, the protein is a viral or prokaryotic or eukaryotic derived protein or developmentally and/or tissue specific regulated protein. The construct of the present invention is particularly useful in conferring genetic resistance against pathogens or inducing apoptosis or other cell death mechanisms useful, for example, in treating cancer or inducing male or female sterility in plants. The constructs permit, therefore, site specific expression and/or developmentally regulated expression of selected genetic sequences.

BACKGROUND OF THE INVENTION

Reference to any prior art in this specification is not, and should not be taken as, an acknowledgment or any form of suggestion that this prior art forms part of the common general knowledge in Australia or any other country.

The increasing sophistication of recombinant DNA technology is greatly facilitating research and development in a range of technological fields such as the medical, horticultural and agricultural industries. Of particular importance, is the exploitation of naturally occurring genetic mechanisms in, for example, pathogens, to induce useful phenotypic changes in cells, such as plant cells. This is particularly evident in the horticultural field in relation to mechanisms to induce resistance in plants to a range of plant pathogens.

There has been considerable progress in the development of virus resistance in crops, for example, through transformation with transgenes derived from the target viruses. The most successful use of transgenes has been with RNA plant viruses. However, despite a number attempts to control single stranded DNA (ssDNA) plant viruses through transgenic resistance, strategies which have been successful for RNA plant viruses have not been as effective for ssDNA plant viruses. DNA plant viruses and particularly the single stranded DNA (ssDNA) plant viruses are responsible for significant commercial losses in a wide range of fruit, vegetable, grain and fibre crops in the tropics and sub-tropics.

There have been two groups of ssDNA viruses which infect plants. These are the Geminiviridae and the recently described nanovirus group. Members of the Geminiviridae have geminate virions and either a monopartite or bipartite circular ssDNA genome. Each molecule is about 2.7 kb in length. Of the Geminiviridae genera, the begomoviruses and the mastreviruses are the most important. The begomoviruses are whitefly-transmitted and have either monopartite or bipartite genomes. Members of this genus include some of the most economically devastating viruses of modem agriculture such as tomato (yellow) leaf curl (consisting of a range of different viruses spread through most tropical and sub-tropical regions), African cassava mosaic (Africa), bean golden mosaic (South and Central America), mungbean yellow mosaic (India) and cotton leaf curl (South and South-East Asia) viruses. The impact of many of the begomoviruses has increased dramatically over recent years as a result of the widespread introduction of the aggressive "B biotype" of the whitefly vector, *Bemesia tabaci*. The mastreviruses have had a lesser impact on agriculture but are responsible for significant losses in some crops. These viruses are transmitted by the leafhoppers and have monopartite genomes. Members of this genus include maize streak (Africa), wheat dwarf (Europe) and tobacco yellow dwarf (Australia) viruses.

The nanoviruses have isometric virions and circular ssDNA genomes but these genomes are multi-component with at least six different integral genomic components each of which is approximately 1 kb. These viruses are transmitted by aphids except for one tentative nanovirus, coconut foliar decay virus, which is transmitted by a treehopper and has only been reported from Vanuatu. The economically most important nanovirus is banana bunchy top virus (BBTV) which nearly destroyed the Australian banana industry in the 1920s and causes major losses in the South Pacific, Asia and Africa. Subterranean clover stunt (Australia), faba bean necrotic yellows (Mediterranean) and coconut foliar decay (Vanuatu) viruses all cause significant yield loss.

The genome organization of the begomoviruses, the mastreviruses and the nanoviruses have significant differences including the number and size of genomic components and number and size of genes, the processing of transcripts, the orientation of genes and the like. There are, however, remarkable similarities which suggest that these viruses have very similar replication and infection strategies. All the gemini- and nanoviruses encode (i) a Rep protein which has nicking and joining activity and directs rolling circle replication of the viral genome; (ii) a virion coat protein; (iii) a protein that is involved in binding host cell retinoblastoma-like proteins resulting in the cell moving to S phase; (iv) a cell-to-cell movement protein; and (v) a nuclear shuttle protein. Further, the viruses have functionally similar intergenic regions (IR). For instance, the IR of begomovimses, the LIR of mastreviruses and the CR-SL of banana bunchy top nanovirus all contain (1) a stem/loop structure, the nonanucleotide loop sequence of which is highly conserved between all gemini- and nanoviruses and is the site of nicking and ligation by the Rep protein; and (ii) a domain within this region which recognizes the Rep protein. The SIR of the mastreviruses and the CR-M of banana bunchy top nanovirus are the site of binding of an endogenous primer responsible for priming the conversion of virion ssDNA into transcriptionally active dsDNA.

The success in developing transgenic resistance to RNA viruses in crops and the increasing demand for such resistance to ssDNA viruses has resulted in investigation of a wide range of strategies for ssDNA viruses targeting various viral genes including the coat protein gene, movement protein gene and the Rep protein gene. In addition, strategies using defective interfering DNAs and a suicide gene have been investigated. Most work in this area has involved begomoviruses rather than mastre- or nanoviruses.

In work leading up to the present invention, the inventors have exploited the replication mechanisms of ssDNA viruses in order to induce genetic resistance in plants. However, the present invention has wide ranging applications in modulating genetic activities such as expression of polynucleotide sequences to effect a particular phenotype in response to a stimulus.

SUMMARY OF THE INVENTION

Throughout this specification, unless the context requires otherwise, the word "comprise", or variations such as "comprises" or "comprising", will be understood to imply the inclusion of a stated element or integer or group of elements or integers but not the exclusion of any other element or integer or group of elements or integers.

Nucleotide and amino acid sequences are referred to by a sequence identifier number (SEQ ID NO:). The SEQ ID NOs: correspond numerically to the sequence identifiers <400>1, <400>2, etc. A sequence listing is provided after the claims.

One aspect of the present invention provides a construct comprising a genetic element operably flanked by nucleotide sequences recognizable by a viral-derived, replication-facilitating protein or its derivatives or eukaryotic and prokaryotic cell homologues when integrated into the genome of a eukaryotic cell which viral-derived, replication-facilitating protein or its derivatives or eukaryotic or prokaryotic cell homologues facilitates excision and circularization of the genetic element and all or part of the flanking nucleotide sequences and wherein said nucleotide sequences recognizable by said viral-derived, replication-facilitating protein or its derivatives or eukaryotic or prokaryotic cell homologues are adjacent to or inserted within one or more extraneous sequences including intron sequences or parts thereof or other splice signals wherein the genetic element and other nucleotide sequences, in a non-circular form, comprise two modular nucleotide sequences which, upon circularization, form a genetic sequence exhibiting a property or a capacity for exhibiting a property absent in the two modular nucleotide sequences prior to circularization or prior to circularization and expression.

Another aspect of the present invention provides a construct comprising a genetic element flanked by Rep-protein recognition sequences or functional homologues from other viruses or eukaryotic or prokaryotic cells which facilitate the generation of a circular nucleotide sequence comprising said genetic element in the presence of a Rep protein or its functional derivatives or homologues wherein said Rep-protein recognition sequences are adjacent to or inserted within one or more recognition sequences, said genetic element comprising a polynucleotide sequence operably linked to regulatory sequences required to permit expression of said polynucleotide sequence when said genetic element is contained within a circularized molecule wherein the genetic element in linear form comprises in the 5' to 3' order:— a polynucleotide sequence; and regulatory sequences to permit expression of said polynucleotide sequence when in circular form, such that upon circularization the genetic element comprises the regulatory sequence separated from the polynucleotide sequence by all or part of a Rep protein recognition sequence wherein upon expression, said polynucleotide sequence encodes an expression product.

A further aspect of the present invention provides a construct comprising in 5' to 3' order first, second, third, fourth, fifth and sixth nucleotide sequences wherein:

the first and sixth nucleotide sequences may be the same or different and each comprises a Rep protein-recognition sequence capable of being recognized by one or more Rep proteins or derivatives or homologues thereof such that genetic material flanked by said first and sixth sequences including all or part of said first and sixth sequences when said construct is integrated in a larger nucleotide sequence such as a genomic sequence, is capable of being excised and circularized wherein said Rep-protein recognition sequences are adjacent to or inserted within one or more extraneous sequences including intronic sequences or parts thereof or other splice signals;

the second nucleotide sequence comprises a 3' portion of polynucleotide sequence;

the third nucleotide sequence is a transcription terminator or functional derivative or homologue thereof operably linked to said second sequence;

the fourth nucleotide sequence is a promoter sequence operably linked to the fifth nucleotide sequence; and the fifth nucleotide sequence is a 5' portion of a polynucleotide sequence wherein the 5' and 3' portions of said polynucleotide sequence represent a full coding sequence of said polynucleotide sequence;

wherein in the presence of one or more Rep proteins, when the construct is integrated into a larger nucleotide sequence such as a genomic sequence, a circularized genetic sequence is generated separate from said larger nucleotide sequence comprising in order said promoter sequence operably linked to a polynucleotide sequence comprising all or part of the extraneous sequence or other splice signal comprising all or part of said first and/or sixth nucleotide sequences and a transcription terminator sequence.

Still another aspect of the present invention is directed to a genetic element for use in generating a construct, said genetic element comprising in 5' to 3' direction, a 3' portion of a polynucleotide sequence operably linked to a transcription terminator; a promoter operably linked to a 5' portion of a polynucleotide sequence wherein upon circularization, the 5' portion of the polynucleotide sequence is operably linked to said 3' portion of the polynucleotide sequence separated by all or part of an extraneous sequence or intron sequence or other splice signal.

Yet another aspect of the present invention provides a construct comprising the nucleotide sequence substantially as set forth in SEQ ID NO:31 to SEQ ID NO:36 or a nucleotide sequence having 60% similarity to each of SEQ ID NO:31 to SEQ ID NO:36 or a nucleotide sequence capable of hybridizing to one or more of SEQ ID NO:31 to SEQ ID NO:36 or a complementary form thereof under low stringency conditions at 42° C.

Even yet another aspect of the present invention contemplates a method for generating a transgenic plant or progeny thereof resistant to a ssDNA virus, said method comprising introducing into the genome of said plant a construct comprising in the 5' to 3' order, a Rep protein-recognition sequence adjacent to or within an intronic sequence or other splice signal, a 3' end portion of a polynucleotide sequence, a transcription terminator or its functional equivalent, a promoter sequence operably linked to a 5' end portion of the polynucleotide sequence wherein the 5' and 3' portions of the polynucleotide sequence represent the coding region of a peptide, polypeptide or protein capable of inducing cell death or dormancy, and same or different Rep protein-recognition sequences; wherein upon infection of said plant cells by ssDNA virus having a Rep protein which is capable of recognizing the flanking Rep protein-recognition sequences, the construct is excised and circularizes thus reconstituting said polynucleotide sequence in a form which is expressed into a peptide, polypeptide or protein which kills the plant cell or otherwise renders the plant cell dormant.

Even still another aspect of the present invention provides a construct comprising a genetic element flanked by a Rep protein-recognition sequences which facilitate the generation of a circular nucleotide sequence comprising said genetic element in the presence of a Rep protein or its functional derivatives or homologues wherein said Rep-protein recognition sequences are adjacent to or inserted within one or more extraneous sequences including intronic sequences or parts thereof or other splice signal, said genetic element comprising a 3' portion and a 5' portion of a promoter separated by a length of a nucleotide sequence to substantially prevent functioning of said promoter, said genetic element in linear form comprises in the 5' to 3' order:— a 3' portion of said promoter;

optionally a polynucleotide sequence operably linked to said 3' portion of said promoter; and a 5' portion of said promoter, such that upon circularization the genetic element comprises the 5' and 3' portions of the promoter sequence separated by all or part of a Rep protein-recognition sequence and/or intron sequences or other splice signal but which does not inactivate the activity of the promoter, said circular molecule optionally further comprising the promoter operably linked to polynucleotide sequence.

The promoter may be a DNA promoter or an RNA promoter.

BRIEF DESCRIPTION OF THE FIGURES

FIG. 1 is a diagrammatic representation of pTBN.

FIG. 2 is a diagrammatic representation of pTBN6.

FIG. 3 is a diagrammatic representation of pTBN1.

FIG. 4 is a diagrammatic representation of pRTBN6.

FIG. 5 is a diagrammatic representation of pRTBN1.

FIG. 6 is a diagrammatic representation of pRTBN 1/6.

FIG. 7 is a schematic representation of plasmid p35S-2301.

FIG. 8 is a schematic representation of plasmid pTEST1.

FIG. 9 is a schematic representation of plasmid pTEST2.

FIG. 10 is a schematic representation of plasmid pTEST3.

FIG. 11 is schematic representation of plasmid pTEST4.

FIG. 12 is a schematic representation of plasmid pBI-TYDV1.1mer.

FIG. 13 is a schematic representation of plasmid p35S-Rep.

FIG. 14 is a graphical representation of the results of a cell death assay using expression vectors. Error bars show 95% confidence intervals.

FIG. 15 is a graphical representation of the results of recircularization cell death assay using expression vectors. Error bars show 95% confidence intervals.

FIG. 16 is a graphical representation of the results from the inducible recircularization cell death assay using expression vectors. Error bars show 95% confidence intervals.

FIG. 17 is a schematic representation of plasmids (A) p35S-BTR-LIR and (B) p35S-BUTR-LIR.

FIG. 18 is a schematic representation of plasmids (A) p35S-BTR and (B) p35S-BUTR.

FIG. 19 is a schematic representation of plasmids (A) pBTR.test1 and (B) pBUTRtest1.

FIG. 20 is a diagrammatic representation of pGI.

FIG. 21 is a diagrammatic representation of pGI6.

FIG. 22 is a diagrammatic representation of pGI1.

FIG. 23 is a diagrammatic representation of pRGI6.

FIG. 24 is a diagrammatic representation of pRGI1.

FIG. 25 is a diagrammatic representation of pRGI 1/6.

FIG. 26 is a schematic representation of a proposed model for Rep-activated expression of human serum albumin from plasmid pHSA1.

FIG. 27 is a diagrammatic representation of a construct for use in sense/antisense modulation of genetic expression.

A summary of sequence identifiers is provided herewith.

SUMMARY OF SEQUENCE IDENTIFIERS

| SEQUENCE IDENTIFIER | DESCRIPTION |
|---|---|
| SEQ ID NO: 1 to SEQ ID NO: 18 | Synthetic oligonucleotide |
| SEQ ID NO: 19 to SEQ ID NO: 44 | Primers |
| SEQ ID NO: 45 to SEQ ID NO: 52 | Synthetic oligonucleotide |
| SEQ ID NO: 66 | Barnase pTBN |
| SEQ ID NO: 67 | Barnase pRTBN6 |
| SEQ ID NO: 68 | Barnase pRTBN1 |
| SEQ ID NO: 69 | GFP pGI |
| SEQ ID NO: 70 | GFP pGI6 |
| SEQ ID NO: 71 | GFP pGI1 |
| SEQ ID NO: 72 | primer |
| SEQ ID NO: 73 | primer |

DETAILED DESCRIPTION OF THE PREFERRED EMBODIMENTS

The present invention is predicated in part on the recognition that a viral-derived, replication-facilitating protein may be used to excise and circularize specific, targeted sequences from the genome of a eukaryotic cell. The term "excise" includes in this case release and more particularly replicative release of targeted sequences. The viral-derived, replication-facilitating proteins initiate nicking, excision and circularization of genetic elements flanked by particular sequences specific for and recognized by the viral-derived, replication-facilitating protein. The present invention extends to derivatives of the viral-derived facilitating proteins and eukaryotic and prokaryotic homologues thereof. The present invention extends to, therefore, any sequences capable of facilitating cleavage and ligation of polynucleotide sequences and are referred to hereinafter as "recognition sequences" and may also be considered herein as "extraneous sequences". The recognition sequences are adjacent to or inserted within extraneous sequences including intronic sequences or other splice signals.

In one embodiment, the circularization process permits the formation of a particular genetic sequence from two modular components separated by a splicable extraneous sequence upon expression. Prior to circularization, the modular components are genetically separated and hence not operably linked. Operable linkage is conveniently shown, for example, in one embodiment, by the ability for the genetic sequence comprising the modular components to be expressed. The term "expressed" in this instance includes transcription to an mRNA sequence and optionally translation of the mRNA sequence to a translation product. Expression, however, is not the sole criterion for constitution of a genetic sequence from modular components. In another embodiment, the genetic sequence produced following circularization may have other useful functions not requiring expression. For example, the resulting genetic sequence may comprise a protein binding recognition sequence thereby targeting particular cytoplasmic or nuclear proteins. Alternatively, the reconstituted polynucleotide sequence comprises an extraneous sequence between the promotors elements and a coding sequence. In the case of the former, the promoter is preferably an RNA promoter such as from a TMV, AMV or TEV virus. Alternatively, the promoter is a DNA promoter where the insertion of the recognition does not substantially adversely affect its activity.

Accordingly, one aspect of the present invention provides a construct comprising a genetic element operably flanked by nucleotide sequences recognizable by a viral-derived, replication-facilitating protein or its derivatives or eukaryotic and prokaryotic cell homologues when integrated into the genome of a eukaryotic cell which viral-derived, replication-facilitating protein or its derivatives or eukaryotic or prokaryotic cell homologues facilitates excision and circularization of the genetic element and all or part of the flanking nucleotide sequences and wherein said nucleotide sequences recognizable by said viral-derived, replication-facilitating protein or its derivatives or eukaryotic or prokaryotic cell homologues are adjacent to or inserted within one or more extraneous sequences including intron sequences or parts thereof or other splice signals wherein the genetic element and other nucleotide sequences, in a non-circular form, comprise two modular nucleotide sequences which, upon circularization, form a genetic sequence exhibiting a property or a capacity for exhibiting a property absent in the two modular nucleotide sequences prior to circularization or prior to circularization and expression.

The term "construct" is used in its broadest sense and includes a genetic construct, nucleic acid molecule, vector, plasmid or any other nucleotide sequence comprising at least two heterologous sequences. The construct, therefore, is a recombinant molecule engineered to comprise two or more nucleotide sequences from different genetic sources. In one embodiment, the construct is in an isolated form. The term "isolated" includes biologically pure, substantially pure or in another condition where at least one purification step has been performed on a sample comprising the construct. A "purification step" includes, for example, a precipitation, centrifugation and/or a chromatographic or electrophoretic separation. In another embodiment, the genetic construct is integrated into the genome of a host cell. The construct may comprise nucleotide sequences which are lost, removed or rearranged following integration. In yet another embodiment, the construct is in circular form either generated in vitro or following excision from the genome of the host cell.

The term "genetic element" is used in its broadest sense and includes a series of two or more nucleotide sequences engineered in a particular order relative to the 5' to 3' or 3' to 5' orientations of the genetic element. In essence, the genetic element comprises two nucleotide sequences in modular form. The term "modular" is not to impart any limitation to the construction or structure of the nucleotide sequences but emphasizes that a single genetic sequence is divided into two components, i.e. modular components. Upon circularization, the two modular components are orientated together to constitute, after removal of any extraneous sequences including intronic and splice sequences or other recognition sequences, a single genetic sequence exhibiting a particular activity or property not present when the genetic sequence is in separate modular form. In certain circumstances, extraneous sequences intervening the two modular components when in circular form may not need to be removed if their presence does not substantially adversely affect the function of the modular components when constituted in the correct orientation relative to each other after circularization. Generally, the modular components are referred to as 5' portions and 3' portions of a polynucleotide sequence. A portion comprises from a few nucleotides (i.e. from about 2 to about 500) to many (i.e. from about 501 to about 10,000). The 5' and 3' portions may encompass a central portion.

In a preferred embodiment, the genetic element comprises, when in circular form, a promoter operably linked to the genetic sequence comprising the two modular sequences. The two modular sequences may be separated by an intronic sequence, splice signal or other recognition sequence. The genetic element comprises, therefore, in linear form in the 5' to 3' direction, a first modular nucleotide sequence comprising the 3' portion of a polynucleotide sequence, a promoter sequence operably linked to the 5' portion of the above-mentioned polynucleotide sequence. Upon circularization, the 3' portion of the polynucleotide sequence is now orientated and fused by base linkage to the 5' portion of the polynucleotide sequence thus reconstituting a functional polynucleotide sequence operably linked to a promoter. Depending on the construct, an intronic sequence, splice signal or other recognition sequence may separate the 5' and 3' portions of the reconstituted polynucleotide sequence. Upon processing during expression, the intronic sequence, splice signal or other recognition sequence may be excised. In a particularly preferred embodiment, the genetic element comprises a transcription terminator sequence operably linked and downstream of the 3' portion of the polynucleotide sequence. Terms such as "promoter" and "terminator" are used in their broadest sense and are described in more detail below.

In another embodiment, the reconstituted polynucleotide sequence encodes an intronic, splice signal or other recognition sequence located between the promoter element and the coding sequence. According to this embodiment, the recognition sequence would not be removed during transcription.

In yet another alternative embodiment, the genetic element comprises two modular components of a promoter or other regulatory sequence. Preferably, the modular components form a promoter sequence after circularization. If an intronic sequence, splice signal or other recognition sequence separates the modular components of a promoter sequence, then such a sequence does not destroy or partially destroy the activity of the promoter sequence. Alternatively, the promoter is an RNA promoter such as a promoter from TMV, AMV or TEV.

The polynucleotide sequence, when reconstituted, exhibits an activity or property or a capacity to exhibit an activity or property not present in the separate modular nucleotide sequences prior to fusion following circularization. Such an activity or property includes the ability to encode a peptide, polypeptide or protein having a particular function, the ability to encode a mRNA sequence which may subsequently be translated into a peptide, polypeptide or protein or which may act as an antisense or sense molecule for down-regulation of a host gene or other genetic sequence or acting as a promoter or other regulatory sequence. Another property contemplated by the genetic sequences includes the ability to bind to protein to interact with nucleic regulatory sequences or to act or encode ribozyme and/or deoxyribozyme molecules.

Of particular importance, the genetic sequence may encode proteins having enzymic activity, regulatory activity or structural activity or exhibit a therapeutic activity if administered to a mammal such as a human or livestock animal. Examples of the latter type of molecule include cytokines, interferons and growth factors. Proteins having enzymic activity are particularly preferred and such proteins are useful in activating a biochemical pathway, facilitating the flow of metabolites down a particular pathway, conferring a property such as resistance to an insecticide, fungicide or herbicide or conferring resistance to a pathogen such as an intracellular pathogen including viruses and intracellular microorganisms. Cells contemplated as targets for the genetic construct of the present invention include animal cells, plant cells, unicellular organisms and microorganisms. Animal cells may be from primates, hmans, livestock animals, avian speices, fish, reptiles, amphibians and insects and arachnids. Plant cells may be from monocotyledonas or dicotyledonas plants.

In one particularly useful embodiment, the peptide, polypeptide or protein encoded by the polynucleotide sequence induces apoptosis or other form of cell death. This is particularly useful as a means of facilitating genetic resistance to viruses, for example, or for mediating cell death of particular types of cells.

In one embodiment, for example, the construct is used to facilitate resistance to a single stranded DNA (ssDNA) virus. Such viruses cause considerable damage to the agricultural and horticultural industries by infecting important crop and ornamental plants. Two groups of ssDNA viruses which infect plants are the gemini- and nanoviruses.

In one embodiment, the flanking sequences recognizable by a viral-derived, replication-facilitating protein or its derivatives or prokaryotic or eukaryotic cell homologues are stem/loop nucleotide structures. Preferably, the stem/loop structures comprise a short nucleotide sequence loop of from about 5 to about 20, preferably from about 6 to about 15 and most preferably about 9 nucleotides (i.e. nonanucleotide) and which is the site of nicking and ligation by the viral-derived, replication-facilitating protein or its derivatives or prokaryotic or eukaryotic cell homologues. In another embodiment, the flanking sequences are recognized by any protein having cleavage and ligation activity. An example of such a protein is topoisomerase. All these sequences are referred to herein as "recognition sequences". Most preferably, the recognition sequences are recognized by the "Rep" protein. This protein is derived from members of the geminiviridae and nanoviruses and binds to a 5' domain on a stem/loop structure comprising the recognition sequence. The present invention, however, is not limited to the use of a stem loop structure although such use is contemplated herein. The present invention extends to any Rep protein from a geminivirus or nanovirus as well as derivatives thereof or homologues from other viruses or from eukaryotic or prokaryotic cells. Examples of eukaryotic cells include mammalian, insect, reptilian; amphibian and yeast cells.

Examples of other recognition sequences or their equivalents include the intergenic regions of BBTV DNA 1-6, the short and long repeats of TLCV or TYDV. An "intronic sequence" is a sequence of nucleotides which, following transcription, have the capacity to be spliced out. In certain circumstances, the intronic sequence is not spliced out such as when the presence of the intronic sequence does not adversely affect the functioning of the sequence into which the intronic sequence is inserted.

The construct of this aspect of the present invention may comprise the same or substantially the same recognition sequences as flanking sequences, that is, the sequences recognizable by a single Rep protein or its derivatives or homologues or may comprise different recognition sequences recognizable by different Rep proteins or derivatives thereof or eukaryotic or prokaryotic cell homologues thereof. Furthermore, the recognition sequences may be full sequences or part sequences such as two half intronic sequences.

The Rep protein may be introduced to a cell such as following viral infection or be encoded by genetic sequences developmentally or tissue specifically expressed in the animal or plant or organism which carries the construct.

In another preferred embodiment, there is provided a construct comprising a genetic element flanked by Rep-protein recognition sequences or functional homologues from other viruses or eukaryotic or prokaryotic cells which facilitate the generation of a circular nucleotide sequence comprising said genetic element in the presence of a Rep protein or its functional derivatives or homologues wherein said Rep-protein recognition sequences are adjacent to or inserted within one or more recognition sequences, said genetic element comprising a polynucleotide sequence operably linked to regulatory sequences required to permit expression of said polynucleotide sequence when said genetic element is contained within a circularized molecule wherein the genetic element in linear form comprises in the 5' to 3' order:— a polynucleotide sequence; and regulatory sequences to permit expression of said polynucleotide sequence when in circular form, such that upon circularization the genetic element comprises the regulatory sequence separated from the polynucleotide sequence by all or part of a Rep protein-recognition sequence wherein upon expression, said polynucleotide sequence encodes an expression product.

Preferably, the regulatory sequences include or comprise a promoter sequence and optionally a transcription terminator. As stated above, a recognition sequence includes an extraneous sequence such as an intronic sequence or other splice signal.

In another embodiment, there is provided a construct comprising a genetic element flanked by a Rep protein-recognition sequences which facilitate the generation of a circular nucleotide sequence comprising said genetic element in the presence of a Rep protein or its functional derivatives or homologues wherein said Rep-protein recognition sequences are adjacent to or inserted within one or more extraneous sequences including intronic sequences or parts thereof or other splice signals, said genetic element comprising a 3' portion and a 5' portion of a promoter separated by a length of a nucleotide sequence to substantially prevent functioning of said promoter, said genetic element in linear form comprises in the 5' to 3' order:— a 3' portion of said promoter;

optionally a polynucleotide sequence operably linked to said 3' portion of said promoter; and a 5' portion of said promoter, such that upon circularization the genetic element comprises the 5' and 3' portions of the promoter sequence separated by all or part of a Rep protein-recognition sequence but which does not inactivate the activity of the promoter, said circular molecule optionally further comprising the promoter operably linked to polynucleotide sequence.

Alternatively, the promoter is an RNA promoter such as from TMV, TEV or AMV.

An advantage of such a system is that when the construct is in linear form and, for example, integrated into a larger nucleotide sequence such as a genome, the promoter sequence is inactive. However, upon circularization, the promoter sequence is reconstituted thus permitting promoter activity. The optionally present operably linked polynucleotide sequence is then expressed.

Examples of suitable promoters include the cauliflower mosaic virus 35S promoter. Another useful promoters is the ubiquitin promoter. Generally, monocot promoters such as the ubiquitin promoter require an intronic sequence between the promoter and the start codon of the expressed exon. Absent this intronic sequence, expression of the promoter is either very low or completely lacking. The genetic construct of the present invention may be designed such that upon circularization, the intronic sequence comprising the stem loop structure forms an intronic sequence downstream of the ubiquitin promoter thus permitting its operation.

Other suitable promoters are described below.

In another preferred embodiment, the present invention provides a construct comprising in 5' to 3' order first, second, third, fourth, fifth and sixth nucleotide sequences wherein:

the first and sixth nucleotide sequences may be the same or different and each comprises a Rep protein-recognition sequence capable of being recognized by one or more Rep proteins or derivatives or homologues thereof such that genetic material flanked by said first and sixth sequences including all or part of said first and sixth sequences when said construct is integrated in a larger nucleotide sequence such as a genomic sequence, is capable of being excised and circularized wherein said Rep-protein recognition sequences are adjacent to or inserted within one or more extraneous sequences including intronic sequences or parts thereof or other splice signals;

the second nucleotide sequence comprises a 3' portion of polynucleotide sequence;

the third nucleotide sequence is a transcription terminator or functional derivative or homologue thereof operably linked to said second sequence;

the fourth nucleotide sequence is a promoter sequence operably linked to the fifth nucleotide sequence; and the fifth nucleotide sequence is a 5' portion of a polynucleotide sequence wherein the 5' and 3' portions of said polynucleotide sequence represent a full coding sequence of said polynucleotide sequence;

wherein in the presence of one or more Rep proteins, when the construct is integrated into a larger nucleotide sequence such as a genomic sequence, a circularized genetic sequence is generated separate from said larger nucleotide sequence comprising in order said promoter sequence operably linked to a polynucleotide sequence comprising all or part of the extraneous sequence or other splice signal comprising all or part of said first and/or sixth nucleotide sequences and a transcription terminator sequence.

In accordance with the above-mentioned aspect of the present invention, the first and sixth nucleotide sequences represent recognition sequences for a viral-derived, replication-facilitating protein such as Rep or derivatives thereof or eukaroytic or prokaryotic derivatives thereof adjacent to or inserted within an intronic sequence or other splice signal. The second to fifth nucleotide sequences represent the genetic elements previously defined.

Yet another aspect of the present invention is directed to a genetic element for use in generating a construct, said genetic element comprising in 5' to 3' direction, a 3' portion of a polynucleotide sequence operably linked to a transcription terminator; a promoter operably linked to a 5' portion of a polynucleotide sequence wherein upon circularization, the 5' portion of the polynucleotide sequence is operably linked to said 3' portion of the polynucleotide sequence separated by all or part of an extraneous sequence or intron sequence or other splice signal.

The constructs of the present invention have a range of applications. In one embodiment, the construct is used to generate genetic resistance in plant cells to ssDNA viruses. The particular viruses for which protection is sought against include but not limited to geminivirus or nanovirus. In this embodiment, the construct comprises a "suicide gene", i.e. a gene encoding a product which induces cell apoptosis, lysis, death or a state of biochemical or physiological dormancy. The construct is introduced into a plant cell under conditions to permit integration into the plant cell genome. A plant is regenerated from the plant cell and propagated when the plant is infected by a particular ssDNA virus having a Rep protein which recognizes the Rep protein-recognition sequences flanking the genetic element of the construct, the construct is excised and recircularizes thus reconstituting the "suicide gene" and facilitating its expression. The cell then dies or otherwise becomes dormant thus preventing the replication and release of ssDNA viruses.

In a particularly preferred embodiment, the present invention provides a construct comprising the nucleotide sequence substantially as set forth in SEQ ID NO:31 to SEQ ID NO:36 or a nucleotide sequence having 60% similarity to each of SEQ ID NO:31 to SEQ ID NO:36 or a nucleotide sequence capable of hybridizing to one or more of SEQ ID NO:31 to SEQ ID NO:36 or a complementary form thereof under low stringency conditions at 42° C.

Accordingly, another aspect of the present invention contemplates a method for generating a transgenic plant or progeny thereof resistant to a ssDNA virus, said method comprising introducing into the genome of said plant a construct comprising in the 5' to 3' order, a Rep protein-recognition sequence adjacent to or within an intronic sequence or other splice signal, a 3' end portion of a polynucleotide sequence, a transcription terminator or its functional equivalent, a promoter sequence operably linked to a 5' end portion of the polynucleotide sequence wherein the 5' and 3' portions of the polynucleotide sequence represent the coding region of a peptide, polypeptide or protein capable of inducing cell death or dormancy, and same or different Rep protein-recognition sequences; wherein upon infection of said plant cells by ssDNA virus having a Rep protein which is capable of recognizing the flanking Rep protein-recognition sequences, the construct is excised and circularizes thus reconstituting said polynucleotide sequence in a form which is expressed into a peptide, polypeptide or protein which kills the plant cell or otherwise renders the plant cell dormant.

Another use of the instant construct is to produce male sterile plants. In this embodiment, a gene encoding a Rep protein is placed under the control of a pollen-specific promoter. A construct comprising the above described "suicide gene" is also generated using Rep protein-recognition sequences recognized by the Rep gene under the control of the pollen-specific promoter. When pollen is formed, the pollen-specific promoter is activated thus activating the suicide gene. Pollen cells are then selectively destroyed or rendered dormant.

Other uses of the construct herein described include introducing genetic material facilitating a colour change into plants or specific tissue or seeds or other reproductive material of plants. An example of a genetic sequence facilitating a colour change is a gene encoding an enzyme of a anthocyanin pathway such as a flavonal 3'-hydroxylase, flavonal 3',5'-hydroxylase, or flavone 3'-synthase.

In another embodiment, the construct may be flanked by two different Rep protein-recognition sequences, i.e. recognized by two different Rep proteins. One Rep protein may then be encoded by a gene inserted into the plant genome and the other Rep protein may be introduced by an infecting ssDNA virus. Alternatively, the Rep proteins may be encoded by different promoters which are expressed and certain development stages.

Although the present invention is particularly described in relation to plants and ssDNA viruses, the present invention extends to homologous excision structures and other proteins with site-specific excision and joining activities from other sources such as non-ssDNA viruses and eukaryotic cells such as insect, mammalian or reptilian cells. Insofar as the present invention relates to plants, the plants may be monocotyledonous or dicotyledonous plants.

The term "plant cell" as used herein includes protoplasts or other cells derived from plants, gamete-producing cells and cells which regenerate into whole plants. Plant cells include cells in plants as well as protoplasts or other cells in culture.

The term "polynucleotide" or "nucleic acid" as used herein designates mRNA, RNA, cRNA, cDNA or DNA.

"Polypeptide", "peptide" and "protein" are used interchangeably herein to refer to a polymer of amino acid residues and to variants of same.

Terms used to describe sequence relationships between two or more polynucleotides or polypeptides include "reference sequence", "comparison window", "sequence identity", "percentage of sequence identity" and "substantial identity". A "reference sequence" is at least 12 but frequently 15 to 18 and often at least 25 monomer units, inclusive of nucleotides and amino acid residues, in length. Because two polynucleotides may each comprise (1) a sequence (i.e., only a portion of the complete polynucleotide sequence) that the two polynucleotides, sequence comparisons between two (or more) polynucleotides are typically performed by comparing sequences of the two polynucleotides over a "comparison window" to identify and compare local regions of sequence similarity. A "comparison window" refers to a conceptual segment of at least 6 contiguous positions, usually about 50 to about 100, more usually about 100 to about 150 in which a sequence is compared to a reference sequence of the same number of contiguous positions after the two sequences are optimally aligned. The comparison window may comprise additions or deletions (i.e., gaps) of about 20% or less as compared to the reference sequence (which does not comprise additions or deletions) for optimal alignment of the two sequences. Optimal alignment of sequences for aligning a comparison window may be conducted by computerised implementations of algorithms (GAP, BESTFIT, FASTA, and TFASTA in the Wisconsin Genetics Software Package Release 7.0, Genetics Computer Group, 575 Science Drive Madison, Wis., USA) or by inspection and the best alignment (i.e., resulting in the highest percentage homology over the comparison window) generated by any of the various methods selected. Reference also may be made to the BLAST family of programs as for example disclosed by Altschul et al., 1997. A detailed discussion of sequence analysis can be found in Unit 19.3 of Ausubel et al., 1994-1998.

The term "sequence identity" as used herein refers to the extent that sequences are identical on a nucleotide-by-nucleotide basis or an amino acid-by-amino acid basis over a window of comparison. Thus, a "percentage of sequence identity" is calculated by comparing two optimally aligned sequences over the window of comparison, determining the number of positions at which the identical nucleic acid base (e.g., A, T, C, G, I) or the identical amino acid residue (e.g., Ala, Pro, Ser, Thr, Gly, Val, Leu, Ile, Phe, Tyr, Trp, Lys, Arg, His, Asp, Glu, Asn, Gln, Cys and Met) occurs in both sequences to yield the number of matched positions, dividing the number of matched positions by the total number of positions in the window of comparison (i.e., the window size), and multiplying the result by 100 to yield the percentage of sequence identity. For the purposes of the present invention, "sequence identity" will be understood to mean the "match percentage" calculated by the DNASIS computer program (Version 2.5 for windows; available from Hitachi Software engineering Co., Ltd., South San Francisco, Calif., USA) using standard defaults as used in the reference manual accompanying the software.

Reference herein to a low stringency includes and encompasses from at least about 0 to at least about 15% v/v formamide and from at least about 1 M to at least about 2 M salt for hybridization, and at least about 1 M to at least about 2 M salt for washing conditions. Generally, low stringency is at from about 25-30° C. to about 42° C. The temperature may be altered and higher temperatures used to replace formamide and/or to give alternative stringency conditions. Alternative stringency conditions may be applied where necessary, such as medium stringency, which includes and encompasses from at least about 16% v/v to at least about 30% v/v formamide and from at least about 0.5 M to at least about 0.9 M salt for hybridization, and at least about 0.5 M to at least about 0.9 M salt for washing conditions, or high stringency, which includes and encompasses from at least about 31% v/v to at least about 50% v/v formamide and from at least about 0.01 M to at least about 0.15 M salt for hybridization, and at least about 0.01 M to at least about 0.15 M salt for washing conditions. In general, washing is carried out $T_m=69.3+0.41$ (G+C) % (Marmur and Doty, 1962). However, the $T_m$ of a duplex DNA decreases by 1° C. with every increase of 1% in the number of mismatch base pairs (Bonner and Laskey, 1974). Formamide is optional in these hybridization conditions. Accordingly, particularly preferred levels of stringency are defined as follows: low stringency is 6×SSC buffer, 0.1% w/v SDS at 25-42° C.; a moderate stringency is 2×SSC buffer, 0.1% w/v SOS at a temperature in the range 20° C. to 65° C.; high stringency is 0.1×SSC buffer, 0.1% w/v SOS at a temperature of at least 65° C.

The term "transformation" means alteration of the genotype of an organism, for example, a eukaryotic cell, by the introduction of a foreign or endogenous nucleic acid.

By "vector" is meant a nucleic acid molecule, preferably a DNA molecule derived, for example, from a plasmid, bacteriophage, or plant virus, into which a nucleic acid sequence may be inserted or cloned. A vector preferably contains one or more unique restriction sites and may be capable of autonomous replication in a defined host cell including a target cell or tissue or a progenitor cell or tissue thereof, or be integrable with the genome of the defined host such that the cloned sequence is reproducible. Accordingly, the vector may be an autonomously replicating vector, i.e., a vector that exists as an extrachromosomal entity, the replication of which is independent of chromosomal replication, e.g., a linear or closed circular plasmid, an extrachromosomal element, a minichromosome, or an artificial chromosome. The vector may contain any means for assuring self-replication. Alternatively, the vector may be one which, when introduced into a cell, is integrated into the genome of the recipient cell and replicated together with the chromosome(s) into which it has been integrated. A vector system may comprise a single vector or plasmid, two or more vectors or plasmids, which together contain the total DNA to be introduced into the genome of the host cell, or a transposon. The choice of the vector will typically depend on the compatibility of the vector with the cell into which the vector is to be introduced. The vector may also include a selection marker such as an antibiotic resistance gene that can be used for selection of suitable transformants. Examples of such resistance genes are well known to those of skill in the art.

The term "gene" is used in its broadest sense and includes cDNA corresponding to the exons of a gene. Accordingly, reference herein to a "gene" is to be taken to include:—
(i) a classical genomic gene consisting of transcriptional and/or translational regulatory sequences and/or a coding region and/or non-translated sequences (i.e. introns, 5'- and 3'-untranslated sequences); or
(ii) mRNA or cDNA corresponding to the coding regions (i.e. exons) and 5'- and 3'-untranslated sequences of the gene; and/or
(iii) a structural region corresponding to the coding regions (i.e. exons) optionally further comprising untranslated sequences and/or a heterologous promoter sequence which consists of transcriptional and/or translational regulatory regions capable of conferring expression characteristics on said structural region.

The term "gene" is also used to describe synthetic or fusion molecules encoding all or part of a functional product, in particular, a sense or antisense mRNA product or a peptide, oligopeptide or polypeptide or a biologically-active protein. Reference to a "gene" also includes reference to a "synthetic gene".

The term "synthetic gene" refers to a non-naturally occurring gene as hereinbefore defined which preferably comprises at least one or more transcriptional and/or translational regulatory sequences operably linked to a structural gene sequence.

The term "structural gene" shall be taken to refer to a nucleotide sequence which is capable of being transmitted to produce mRNA and optionally, encodes a peptide, oligopeptide, polypeptide or biologically active protein molecule. Those skilled in the art will be aware that not all mRNA is capable of being translated into a peptide, oligopeptide, polypeptide or protein, for example, if the mRNA lacks a functional translation start signal or alternatively, if the mRNA is antisense mRNA. The present invention clearly encompasses synthetic genes comprising nucleotide sequences which are not capable of encoding peptides, oligopeptides, polypeptides or biologically-active proteins. In particular, the present inventors have found that such synthetic genes may be advantageous in modifying target gene expression in cells, tissues or organs of a eukaryotic organism.

The term "structural gene region" refers to that part of a synthetic gene which is expressed in a cell, tissue or organ under the control of a promoter sequence to which it is operably connected. A structural gene region may be operably under the control of a single promoter sequence or multiple promoter sequences. Accordingly, the structural gene region of a synthetic gene may comprise a nucleotide sequence which is capable of encoding an amino acid sequence or is complementary thereto. In this regard, a structural gene region which is used in the performance of the instant invention may also comprise a nucleotide sequence which encodes an amino acid sequence yet lacks a functional translation initiation codon and/or a functional translation stop codon and, as a consequence, does not comprise a complete open reading frame. In the present context, the term "structural gene region" also extends to a non-coding nucleotide sequences, such as 5'-upstream or 3'-downstream sequences of a gene which would not normally be translated in a eukaryotic cell which expresses said gene.

Accordingly, in the context of the present invention, a structural gene region may also comprise a fusion between two or more open reading frames of the same or different genes. In such embodiments, the invention may be used to modulate the expression of one gene, by targeting different non-contiguous regions thereof or alternatively, to simultaneously modulate the expression of several different genes, including different genes of a multigene family. In the case of a fusion nucleic acid molecule which is non-endogenous to a eukaryotic cell and in particular comprises two or more nucleotide sequences derived from a viral pathogen, the fusion may provide the added advantage of conferring simultaneous immunity or protection against several pathogens, by targeting the expression of genes in said several pathogens. Alternatively or in addition, the fusion may provide more effective immunity against any pathogen by targeting the expression of more than one gene of that pathogen.

Particularly preferred structural gene regions according to this aspect of the invention are those which include at least one translatable open reading frame, more preferably further including a translational start codon located at the 5'-end of said open reading frame, albeit not necessarily at the 5'-terminus of said structural gene region. In this regard, notwithstanding that the structural gene region may comprise at least one translatable open reading frame and/or AUG or ATG translational start codon, the including of such sequences in no way suggest that the present invention requires translation of the introduced nucleic acid molecule to occur in order to modulate the expression of the target gene. Whilst not being bound by any theory or mode of action, the inclusion of at least one translatable open reading frame and/or trauslational start codon in the subject nucleic acid molecule may serve to increase stability of the mRNA transcription product thereof, thereby improving the efficiency of the invention.

The optimum number of structural gene sequences which may be involved in the synthetic gene of the present invention will vary considerably, depending upon the length of each of said structural gene sequences, their orientation and degree of identity to each other. For example, those skilled in the art will be aware of the inherent instability of palindromic nucleotide sequences in vivo and the difficulties associated with constructing long synthetic genes comprising inverted repeated nucleotide sequences because of the tendency for such sequences to recombine in vivo. Notwithstanding such difficulties, the optimum number of structural gene sequences to be included in the synthetic genes of the present invention may be determined empirically by those skilled in the art, without any undue experimentation and by following standard procedures such as the construction of the synthetic gene of the invention using recombinase-deficient cell lines, reducing the number of repeated sequences to a level which eliminates or minimizes recombination events and by keeping the total length of the multiple structural gene sequence to an acceptable limit, preferably no more than 5-10 kb, more preferably no more than 2-5 kb and even more preferably no more than 0.5-2.0 kb in length.

For expression in eukaryotic cells, the construct generally comprises, in addition to the polynucleotide sequence, a promoter and optionally other regulatory sequences designed to facilitate expression of the polynucleotide sequence.

Reference herein to a "promoter" is to be taken in its broadest context and includes the transcriptional regulatory sequences of a classical genomic gene, including the TATA box which is required for accurate transcription initiation, with or without a CCAAT box sequence and additional regulatory elements (i.e. upstream activating sequences, enhancers and silencers) which alter gene expression in response to developmental and/or external stimuli, or in a tissue-specific manner. A promoter is usually, but not necessarily, positioned upstream or 5', or a structural gene region, the expression of which it regulates. Furthermore, the regulatory elements comprising a promoter are usually positioned within 2 kb of the start site of transcription of the gene.

In the present context, the term "promoter" is also used to describe a synthetic or fusion molecule, or derivative which confers, activates or enhances expression of a nucleic acid molecule in a cell.

Preferred promoters may contain additional copies of one or more specific regulatory elements, to further enhance expression of the sense molecule and/or to alter the spatial expression and/or temporal expression of said sense molecule. For example, regulatory elements which confer copper inducibility may be placed adjacent to a heterologous promoter sequence driving expression of a sense molecule, thereby conferring copper inducibility on the expression of said molecules.

Placing a nucleic acid molecule under the regulatory control of a promoter sequence means positioning the said molecule such that expression is controlled by the promoter sequence. Promoters are generally positioned 5' (upstream) to the genes that they control. In the construction of heterologous promoter/structural gene combinations, it is generally preferred to position the promoter at a distance from the gene transcription start site that is approximately the same as the distance between that promoter and the gene it controls in its natural setting, i.e. the gene from which the promoter is derived. As is known in the art, some variation in this distance can be accommodated without loss of promoter function. Similarly, the preferred positioning of a regulatory sequence element with respect to a heterologous gene to be placed under its control is defined by the positioning of the element in its natural setting, i.e. the genes from which it is derived. Again, as is known in the art, some variation in this distance can also occur.

Examples of promoters suitable for use in the synthetic genes of the present invention include viral, fungal, bacterial, animal and plant derived promoters capable of functioning in plant, animal, insect, fungal, yeast or bacterial cells. The promoter may regulate the expression of the structural gene component constitutively, or differentially with respect to cell, the tissue or organ in which expression occurs or, with respect to the developmental stage at which expression occurs, or in response to external stimuli such as physiological stresses, or pathogens, or metal ions, amongst others.

Preferably, the promoter is capable of regulating expression of a nucleic acid molecule in a eukaryotic cell, tissue or organ, at least during the period of time over which the target gene is expressed therein and more preferably also immediately preceding the commencement of detectable expression of the target gene in said cell, tissue or organ.

Accordingly, strong constitutive promoters are particularly useful for the purposes of the present invention or promoters which may be induced by virus infection or the commencement of target gene expression.

Plant-operable and animal-operable promoters are particularly preferred for use in the construct of the present invention. Examples of preferred promoters include the viral promoters such as bacteriophage T7 promoter, bacteriophage T3 promoter, SP6 promoter, bacterial promoters such as lac operator-promoter, tac promoter, viral promotors such as SV40 late promoter, SV40 early promoter, RSV-LTR promoter, CMV M promoter or plant viral promoters such as CaMV 35S promoter, SCSV promoter, SCBV promoter and the like.

In consideration of the preferred requirement for high-level expression which coincides with expression of the target gene or precedes expression of the target gene, it is highly desirable that the promoter sequence is a constitutive strong promoter in the host of interest such as the CMV-IE promoter or the SV40 early promoter sequence, the SV40 late promoter sequence for mammalian cells and, the CaMV 35S promoter, or the SCBV promoter in certain plant cells, amongst others. Those drilled in the art will readily be aware of additional promoter sequences other than those specifically described.

In the present context, the terms "in operable connection with" or "operably under the control" or similar shall be taken to indicate that expression of the structural gene region or multiple structural gene region is under the control of the promoter sequence with which it is spatially connected; in a cell, tissue, organ or whole organism.

The construct preferably contains additional regulatory elements for efficient transcription, for example, a transcription termination sequence.

The term "terminator" refers to a DNA sequence at the end of a transcriptional unit which signals termination of transcription. Terminators are 3'-non-translated DNA sequences generally containing a polyadenylation signal, which facilitates the addition of polyadenylate sequences to the 3'-end of a primary transcript. Terminators active in plant cells are known and described in the literature. They may be isolated from bacteria, fungi, viruses, animals and/or plants or synthesized de novo.

As with promoter sequences, the terminator may be any terminator sequence which is operable in the cells, tissues or organs in which it is intended to be used.

Examples of terminators particularly suitable for use in the synthetic genes of the present invention include the SV40 polyadenylation signal, the HSV TK polyadenylation the CYC1 terminator, ADH terminator, SPA terminator, nopaline synthase (NOS) gene terminator of *Agrobacterium tumefaciens*, the terminator of the cauliflower mosaic virus (CaMV) 35S gene, the zein gene terminator from *Zea mays*, the Rubisco small subunit gene (SSU) gene terminator sequences, subclover stunt virus (SCSV) gene sequence terminators, any rho-independent *E. coli* terminator, or the lacZ alpha terminator, amongst others.

In a particularly preferred embodiment, the terminator is the SV40 polyadenylation signal or the HSV TK polyadenylation signal which are operable in animal cells, tissues and organs, octopine synthase (OCS) or nopaline synthase (NOS) terminator active in plant cells, tissue or organs, or the lacZ alpha terminator which is active in prokaryotic cells.

Those skilled in the art will be aware of additional terminator sequences which may be suitable for use in performing the invention. Such sequences may readily be used without any undue experimentation.

Means for introducing (i.e. transfecting or transforming) cells with the constructs are well-known to those skilled in the art.

The constructs described supra are capable of being modified further, for example, by the inclusion of marker nucleotide sequences encoding a detectable marker enzyme or a functional analogue or derivative thereof, to facilitate detection of the synthetic gene in a cell, tissue or organ in which it is expressed. According to this embodiment, the marker nucleotide sequences will be present in a translatable format and expressed, for example, as a fusion polypeptide with the translation product(s) of any one or more of the structural genes or alternatively as a non-fusion polypeptide.

Those skilled in the art will be aware of how to produce the synthetic genes described herein and of the requirements for obtaining the expression thereof, when so desired, in a specific cell or cell-type under the conditions desired. In particular, it will be known to those skilled in the art that the genetic manipulations required to perform the present invention may require the propagation of a genetic construct described herein or a derivative thereof in a prokaryotic cell such as an *E. coli* cell or a plant cell or an animal cell.

The constructs of the present invention may be introduced to a suitable cell, tissue or organ without modification as linear DNA, optionally contained within a suitable carrier, such as a cell, virus particle or liposome, amongst others. To produce a genetic construct, the synthetic gene of the invention is inserted into a suitable vector or opisome molecule, such as a bacteriophage vector, viral vector or a plasmid, cosmid or artificial chromosome vector which is capable of being maintained and/or replicated and/or expressed in the host cell, tissue or organ into which it is subsequently introduced.

Accordingly, a further aspect of the invention provides a genetic construct which at least comprises a genetic element as herein described and one or more origins of replication and/or selectable marker gene sequences.

Genetic constructs are particularly suitable for the transformation of a eukaryotic cell to introduce novel genetic traits thereto, in addition to the provision of resistance characteristics to viral pathogens. Such additional novel traits may be introduced in a separate genetic construct or, alternatively, on the same genetic construct which comprises the synthetic genes described herein. Those skilled in the art will recognize the significant advantages, in particular in terms of reduced genetic manipulations and tissue culture requirements and increased cost-effectiveness, of including genetic sequences which encode such additional traits and the synthetic genes described herein in a single genetic construct.

Usually, an origin of replication or a selectable marker gene suitable for use in bacteria is physically-separated from those genetic sequences contained in the genetic construct which are intended to be expressed or transferred to a eukaryotic cell, or integrated into the genome of a eukaryotic cell.

As used herein, the term "selectable marker gene" includes any gene which confers a phenotype on a cell on which it is expressed to facilitate the identification and/or selection of cells which are transfected or transformed with a genetic construct of the invention or a derivative thereof.

Suitable selectable marker genes contemplated herein include the ampicillin-resistance gene ($Amp^r$), tetracycline-resistance gene ($Tc^r$), bacterial kanamycin-resistance gene ($Kan^r$), is the zeocin resistance gene (Zeocin is a drug of the bleomycin family which is trade mark of InVitrogen Corporation), the AURI-C gene which confers resistance to the antibiotic aureobasidin A, phosphinothricin-resistance gene, neomycin phosphotransferase gen (nptII), hygromycin-resistance gene, β-glucuronidase (GUS) gene, chloramphenicol acetyltransferase (CAT) gene, green fluorescent protein-encoding gene or the luciferase gene, amongst others.

Preferably, the selectable marker gene is the nptII gene or $Kan^r$ gene or green fluorescent protein (GFP)-encoding gene.

Those skilled in the art will be aware of other selectable marker genes useful in the performance of the present invention and the subject invention is not limited by the nature of the selectable marker gene.

The present invention extends to all genetic constructs essentially as described herein, which include further genetic sequences intended for the maintenance and/or replication of said genetic construct in prokaryotes or eukaryotes and/or the integration of said genetic construct or a part thereof into the genome of a eukaryotic cell or organism.

Standard methods described supra may be used to introduce the constructs into the cell, tissue or organ, for example, liposome-mediated transfection or transformation, transformation of cells with attenuated virus particles or bacterial cells, cell mating, transformation or transfection procedures known to those skilled in the art.

Additional means for introducing recombinant DNA into plant tissue or cells include, but are not limited to, transformation using $CaCl_2$ and variations thereof, direct DNA uptake into protoplasts, PEG-mediated uptake to protoplasts, microparticle bombardment, electroporation, microinjection of DNA, microparticle bombardment of tissue explant or cells, vacuum-infiltration of tissue with nucleic acid, or in the case of plants, T-DNA-mediate transfer from *Agrobacterium* to the plant tissue.

For microparticle bombardment of cells, a microparticle is propelled into a cell to produce a transformed cell. Any suitable ballistic cell transformation methodology and apparatus can be used in performing the present invention. Exemplary apparatus and procedures are disclosed by Stomp et al. (U.S. Pat. No. 5,122,466) and Sanford and Wolf (U.S. Pat. No. 4,945,050). When using ballistic transformation procedures, the genetic construct may incorporate a plasmid capable of replicating in the cell to be transformed.

Examples of microparticles suitable for use in such systems include 1 to 5 μm gold spheres. The DNA construct may be deposited on the microparticle by any suitable technique, such as by precipitation.

In a further embodiment of the present invention, the genetic constructs described herein are adapted for integration into the genome of a cell in which it is expressed. Those skilled in the art will be aware that, in order to achieve integration of a genetic sequence or genetic construct into the genome of a host cell, certain additional genetic sequences may be required. In the case of plants, left and right border sequences from the T-DNA of the *Agrobacterium tumefaciens* Ti plasmid will generally be required.

The present invention further extends to an isolated cell, tissue or organ comprising the constructs or parts thereof. The present invention extends further to regenerated tissues, organs and whole organisms derived from said cells, tissues and organs and to propagules and progeny thereof as well as seeds and other reproductive material.

For example, plants may be regenerated from transformed plant cells or tissues or organs on hormone-containing media and the regenerated plants may take a variety of forms, such as chimeras of transformed cells and non-transformed cells; clonal transformants (e.g. all cells transformed to contain the expression cassette); grafts of transformed and untransformed tissue (e.g. a transformed root stock grafted to an untransformed scion in citrus species). Transformed plants may be propagated by a variety of means, such as by clonal propagation or classical breeding techniques. For example, a first generation (or T1) transformed plants may be selfed to give homozygous second generation (or T2) transformed plants, and the T2 plants further propagated through classical breeding techniques.

In another embodiment, the construct is used to induce modulation of expression of a target genetic sequence. For example, a construct, when in linear form, comprises in the 5' to 3' direction an antisense sequence, a promoter and a sense sequence. These elements are then flanked by viral-derived, replication-faciliating protein recognition sequences (e.g. stem loop) or mammalian or microbial homologues. A terminator sequence is located outside the recognition-sequence flanked region. Upon replicative release, a polynucleotide sequence comprising antisense and sense forms of a target genetic sequence is produced.

Figure 27:
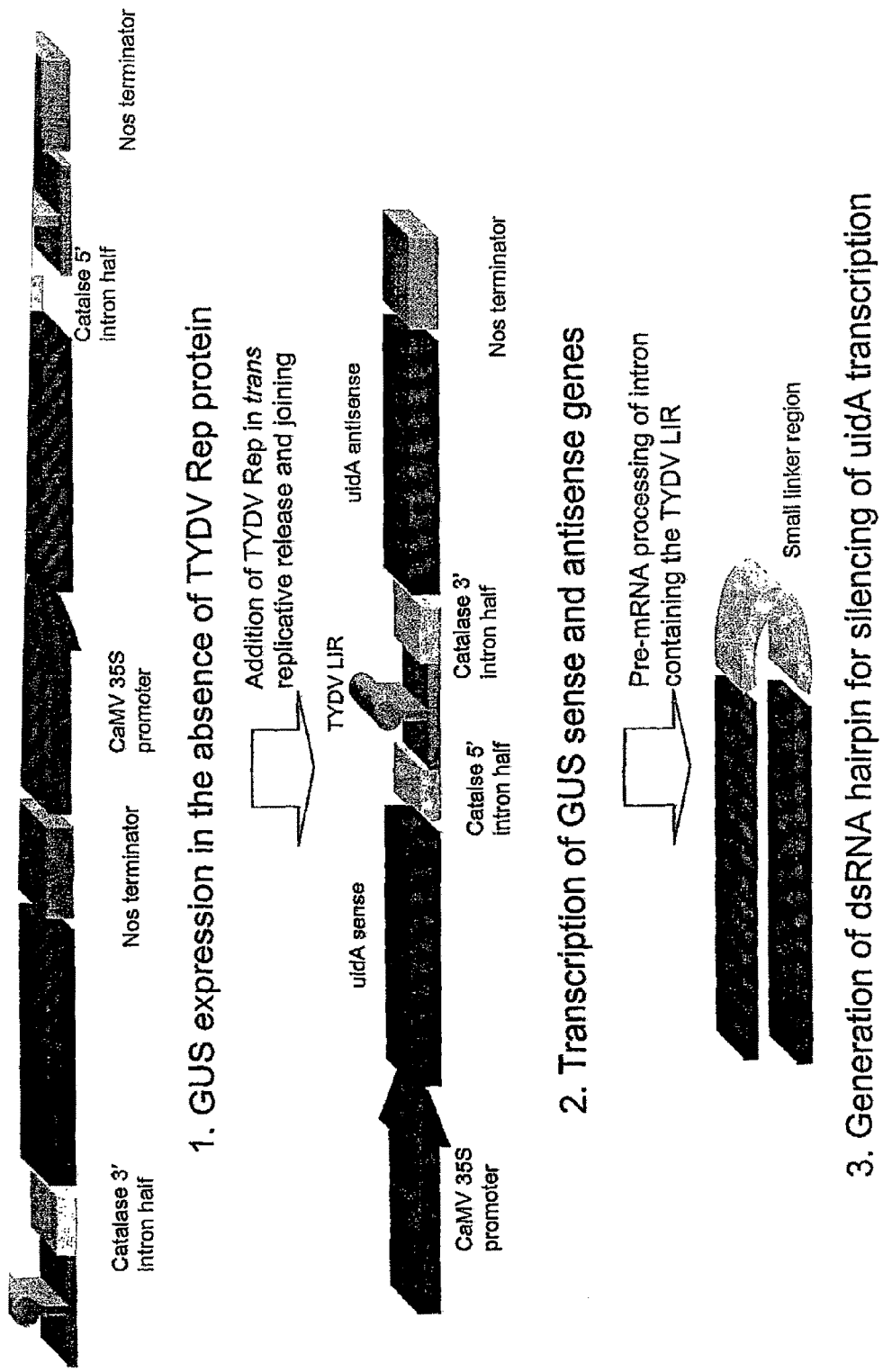

The resulting polynucleotide sequence may then form a hair-pin loop. The construct may be varied to produce tandem or multiple repeats, inverts or combinations thereof. Such constructs are useful for gene silencing in plant and animal cells. The order of elements in the linear form is not critical. For example, the location of the sense and antisense sequences may be exchanged. An example of one suitable construct is shown in FIG. 27.

The present invention is further described by the following non-limiting Examples.

Example 1

Expression Vectors Based on BBTV

A series of expression vectors were constructed which contain the cauliflower mosaic virus 35S promoter (355) driving expression of the gene encoding barnase, into which the intron from the potato light-inducible tissue-specific ST-LS1 gene was introduced (NT-INTRON-CT). The terminator was derived from either the gene encoding nopaline synthase (nos) or the major open-reading frame (ORF) of BBTV DNA-6 (BT6).

Figure 2:
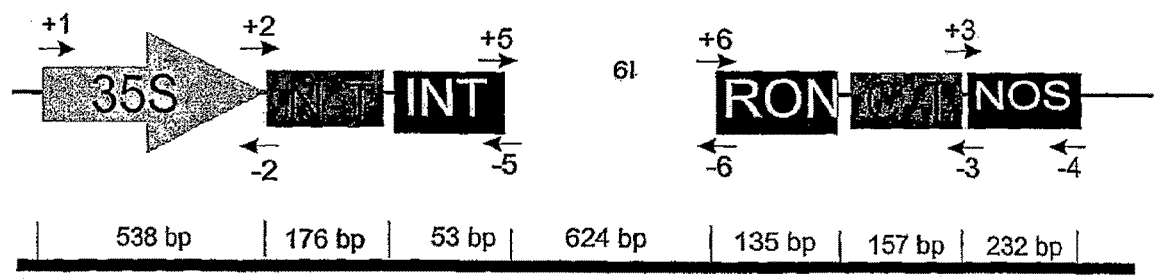
Figure 3:
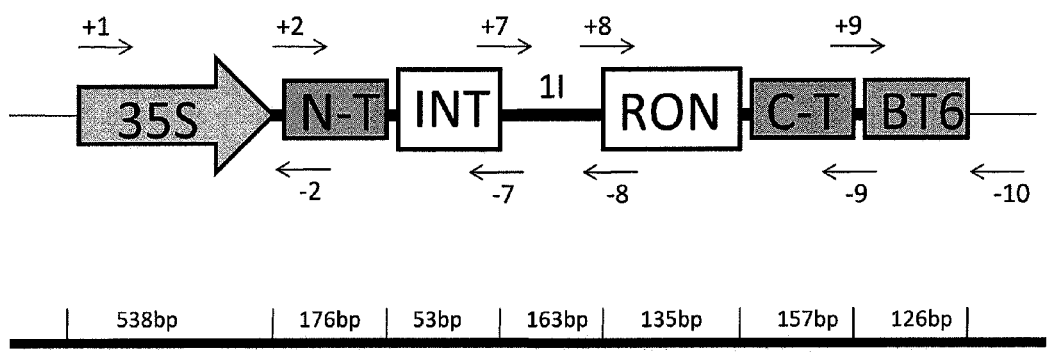

The constructs were assembled using PCR with overlapping primers (Table 1) and cloned into pGEM-T vectors using standard techniques known in the art. The expression vector pTBN was constructed and is shown in FIG. 1. pTBN (SEQ ID NO:66) represents the backbone upon which other expression vectors were constructed. Primer names and binding sites are indicated, as is the size of each sequence. pTBN (like the other constructs) was amplified in a step-wise manner. Initially, all three fragments were separately amplified (i.e. 35S, NT-INTRON-CT and nos). The entire sequence was then amplified by mixing each of the fragments in a PCR with primers +1 and −4.

pTBN6 (SEQ ID NO:67) shown in FIG. 2 contains a 624 by region containing the CR-SL and CR-M of BBTV DNA-6 (61), inserted into the intron.

pTBN1 (SEQ ID NO:68) shown in FIG. 3 contains 163 by region containing the CR-SL and CR-M of BBTV DNA-1 (1I), inserted into the intron, identically to pTBN6. The nos terminator was replaced by the 126 by terminator from BBTV DNA-6 large ORF.

Figure 4:
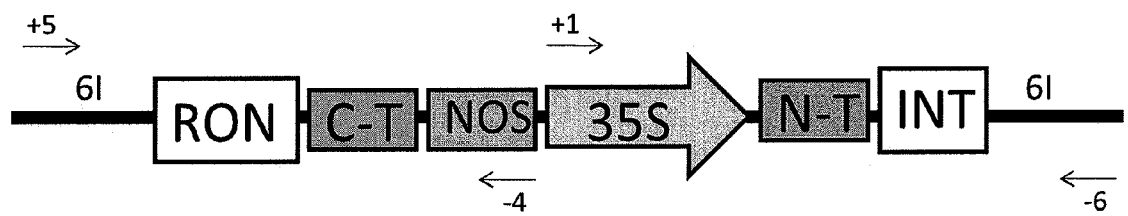
Figure 5:
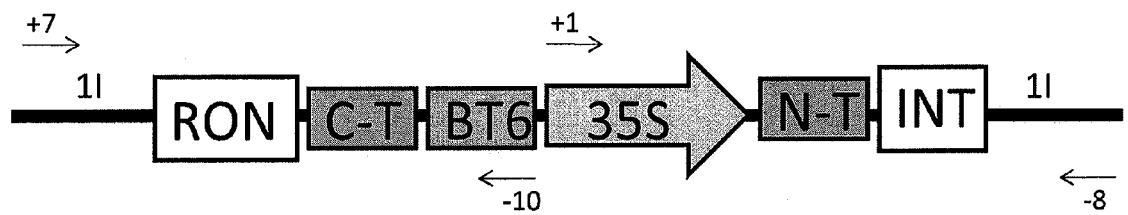
Figure 6:
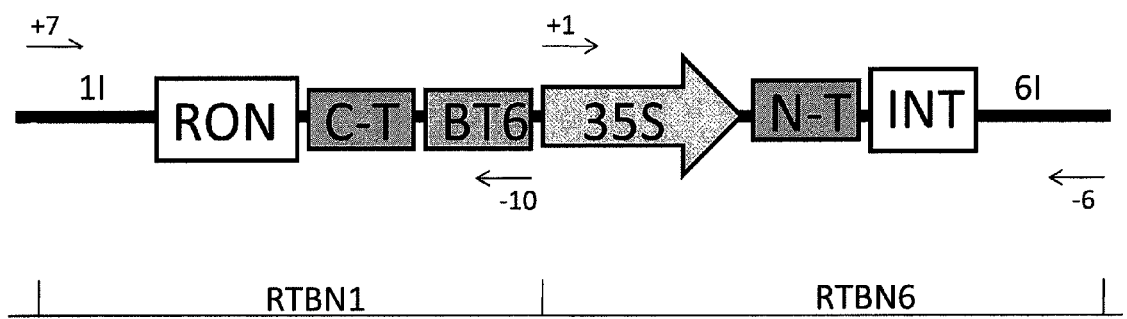

Recircularization vectors are based upon pTBN6 and pTBN1. They are flanked by Rep recognition sequences and designed to recircularize and subsequently be transcriptionally active, only in the presence of the BBTV Rep. Three different vectors were made: pRTBN6, pRTBN1 and pRTBN1/6.

pRTBN6 shown in FIG. 4 was constructed from pTBN6. Two fragments were amplified using +5 and −4 and +1 and −6 respectively. These were cloned into pGEM-T and sub-cloned to create pRTBN6.

pRTBN1 shown in FIG. 5 was constructed from pTBN1 in a similar fashion to pRTBN6.

pRTBN1/6 shown in FIG. 6 was a hybrid of pRTBN1 and pRTBN6.

Untranslatable vectors were also constructed for each of the constructs mentioned above (except pTBN). In these vectors, the start codon of the barnase gene was deleted using the +11 primer (refer to Table 1). The constructs were named pUBN6, pUBN1, pRUBN6 and pRUBN1.

TABLE 1

Oligonucleotide primer sequences

| Primer | Name | Sequence (5'-3') |
|---|---|---|
| +1 | 3TS1-H | AAGCTTCATGGAGTCAAAGA (SEQ ID NO: 1) |
| +2 | 35S1-B | TCATTTGGAGAGGATCCATGGCACAGGTT (SEQ ID NO: 2) |
| −2 | B2-35S | AACCTGTGCCATGGATCCTCTCCAAATGA (SEQ ID NO: 3) |
| +3 | B1-N | AAAATCAGATAAGAGCTCGATCGTTCAAA (SEQ ID NO: 4) |
| −3 | N2-B | TTTGAACGATCGAGCTCTTATCTGATTTT (SEQ ID NO: 5) |
| −4 | NOS4-H | AAGCTTTTCGCCATTCAGGCTGC (SEQ ID NO: 6) |
| +5 | B3-6 | TATCATTAATTAGTAAGTTGTGCTGTAA (SEQ ID NO: 7) |
| −5 | 6-B4 | TTACAGCACAACTTACTAATTAATGATA (SEQ ID NO: 8) |
| +6 | 6-B3 | GGAAGGCAGAAGCGAGTAATATAATATT (SEQ ID NO: 9) |
| −6 | B4-6 | AATATTATATTACTCGCTTCTGCCTTCC (SEQ ID NO: 10) |
| +7 | B5-I | ATCATTAATTAGTCACACTATGACAAAAG (SEQ ID NO: 11) |
| −7 | I-B6 | TTGTCATAGTGTGACTAATTAATGATAAT (SEQ ID NO: 12) |
| +8 | I-B5 | GACATTTGCATCAGTAATATAATATTTCA (SEQ ID NO: 13) |
| −8 | B6-I | AATATTATATTACTGATGCAAATGTCCCG (SEQ ID NO: 14) |
| +9 | B7-6T | TCAGATAAGAGCTCAGTAACAGCAACAAC (SEQ ID NO: 15) |
| −9 | 6T2-B | GCTGTTACTGAGCTCTTATCTGATCTTTG (SEQ ID NO: 16) |
| −10 | 6T4-H | AAGCTTATTTCCCAAATATACGT (SEQ ID NO: 17) |
| +11 | UNTBarn | GGATCCGCACAGGTTATCAAC (SEQ ID NO: 18) |

Example 2

Expression Vectors Based on TYDV (a) Construction of an Intron-Containing Gus Reporter Gene Expression Cassette The vector pCAMBIA 2301 was obtained from CAMBIA (Can berra, Australia). This vector contains a 189 by catalase intron within the 5' portion of the uidA coding region. The CaMV 35S promoter region (800 bp), uidA coding region, and nos terminator were removed from pCAMBIA 2301 as a HindIII/SphI fragment and inserted into similarly digested pGEM-T (Promega) vector. The subsequent construct was designated pGEM-2301. The 800 by CaMV 35S promoter was replaced with the stronger 530 by CaMV 35S promoter by NotI/BglII digestion and ligation. The subsequent vector was designated p35S-2301 (FIG. 7) and served as the template for all subsequent cloning steps.

(b) Isolation of the Tobacco Yellow Dwarf Mastrevirus (TYDV) 9 Large Intergenic Region and Insertion into the Catalase Intron of p35S-2301

A 272 by fragment incorporating the large intergenic region (LIR) (nt +1 to nt +272) of TYDV (Genbank Ace M81103) was amplified from TYDV-infected tobacco leaf tissue by PCR using primers LIR-F and LIR-R (see FIG. 1). This fragment was designated LIR.

Primers:

```
LIR-F
                                            [SEQ ID NO: 19]
5'-GCTCTTCCTGCAGGCGGCCGCATTAAGGCTCAAGTACCGTA 3'

LIR-R
                                            [SEQ ID NO: 20]
5'-GCTCTTCGTCGACGAATTCATTTTCAACTTTGGGATGTCAC-3'
```

The segment comprising the CaMV 35S promoter (530 bp), uidA $1^{st}$ exon (19 bp), and 5' half of the catalase intron (83 bp) was amplified from p35S-2301 plasmid DNA by PCR, using primers 35S-IE and CAT-A. This fragment was designated CAT-A.

Primers:

```
                                            [SEQ ID NO: 21]
35S-IE  5'-GAATTCCATGGAGTCAAAGATTCA-3'

[SEQ ID NO: 22]
CAT-A  5'-GCCCGCTGCAGAGTTTAAAGAAAGATCAAAGC-3'
```

The segment comprising the 3' half of the catalase intron (106 bp) and uidA $2^{nd}$ exon (1809 bp) was amplified from p35S-2301 plasmid DNA by PCR, using primers CAT-B and GUS-BstEII. This fragment was designated CAT-B.

Primers:

```
CAT-B
                                            [SEQ ID NO: 23]
5'-GCCCCGGTCGACGATCTATTTTTTAATTGATTGG-3'

GUS-BstEII
                                            [SEQ ID NO: 24]
5'-TTCGAGCTGGTCACCTGTAATTCACACGTGGTG-3'
```

Figure 8:
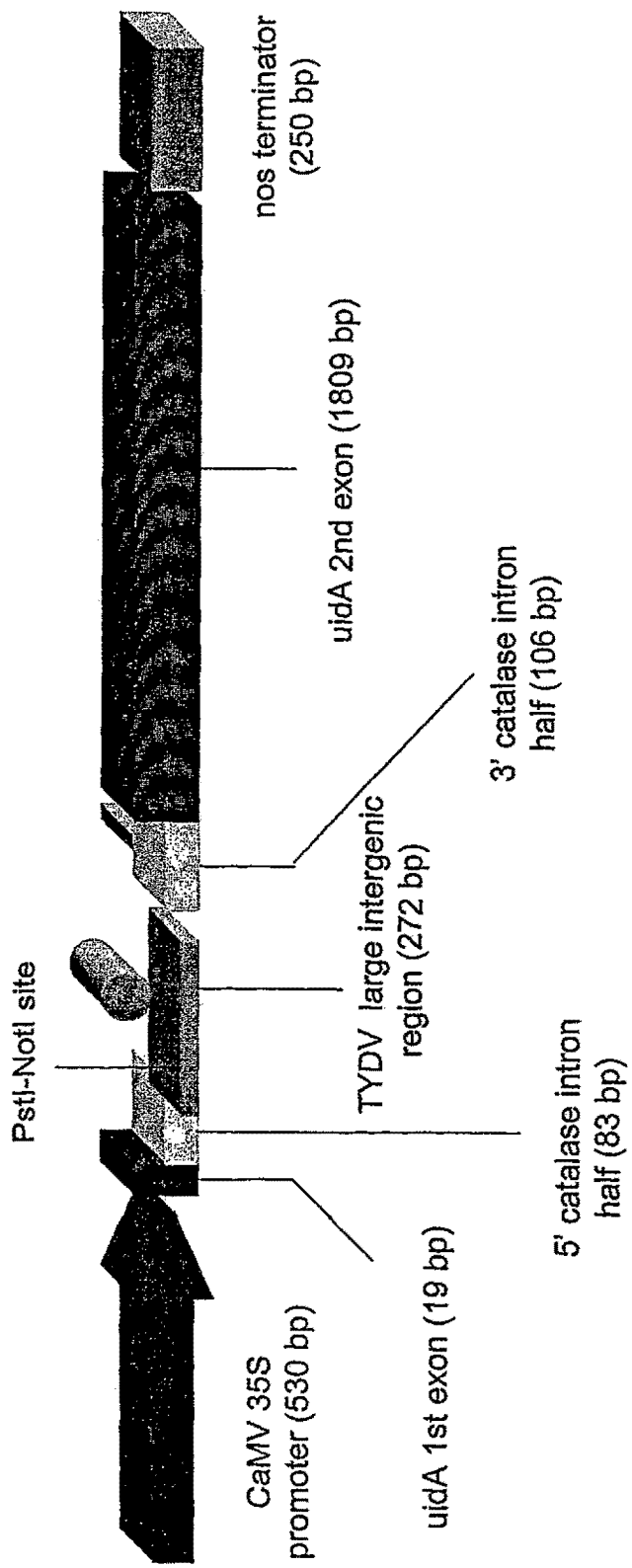

The resulting PCR products were cloned into pGEM-T and the nucleotide sequence verified. Ultimately, each fragment was excised (CAT-A using EcoRI/PstI, LIR using PstI/SalI, and CAT-B using SalI/BstEII) from pGEM-T, and ligated together into EcoRI/BstEII digested p35S-2301 to create the plasmid pTEST1 (FIG. 8).

(c) To Determine Whether GUS Expression is Affected by Insertion of the TYDV LIR into the Catalase Intron In order to determine whether GUS expression, and therefore intron splicing, was affected by insertion of the TYDV LIR into the catalase intron of p355-2301, constructs were bombarded into embryogenic banana cells and GUS activity transiently assayed. Test plasmid pTEST1 and positive control plasmid p35S-2301 were coated onto 1 μm gold particles and biolistically introduced into 5 day old banana (*Musa* spp.

cv. "Ladyfinger" AAA) embryogenic cells according to Becker et al. (2000). Two days post-bombardment, cells were harvested and GUS activity assayed histochemically (Jefferson et al., 1987).

No endogenous GUS activity was observed in non-bombarded cells. Strong GUS activity, evident as bright blue staining cell foci, was observed from cells bombarded with the positive control plasmid p355-2301. In contrast, GUS expression from cells bombarded with pTEST1, was lower (about 5-fold) as determined by number and intensity of blue staining cell foci. This result suggested that insertion of the TYDV LIR into the catalase intron of p358-2301 does not abolish GUS expression, but may affect intron processing to some degree.

(d) Identification of Cryptic Intron Splice Sites within the TYDV LIR

In order to determine whether the TYDV LIR contained potential cryptic intron splice sites, which may affect pre-mRNA processing, cDNA was synthesized from RNA extracts derived from cells bombarded with p355-2301 and pTEST1. Total RNA was isolated from banana cells two days post bombardment with p355-2301 and pTEST1 using the method of Chang et al. (1993) Complementary DNA was synthesized from total RNA using the primer uidA2. This cDNA served as a template for a nested PCR using primers uidA1 and uidA3. The resulting PCR products were cloned into pGEM-T and sequenced. Sequencing identified two potential sites within the TYDV LIR, which may contribute to aberrant splicing of the catalase baton from the uidA coding region pre-mRNA. The first sequence, CTGCAGVGC, located within the primer LIR-F used to isolated the TYDV LIR, bears strong similarity to the consensus 3' splice site (T(10X)GCAGVGT). The second sequence, TAVGTGAGT (nt +43 to nt +50), shares some similarity to the consensus 5' splice site (AGVGTAAGT).

Primers:

```
uidA1
5'-CCATGGTAGATCTGAGGG-3'           [SEQ ID NO: 25]

uidA2
5'-TACGTACACTTTTCCCGGCAATAAC-3'    [SEQ ID NO: 26]

uidA3
5'-GTAACGCGCTTTCCCACCAACGC-3'      [SEQ ID NO: 27]
```

(e) Removal of the 3' Cryptic Intron Splice Site from the TYDV LIR

Of the two cryptic intron splice sites identified, the first (CTGCAGGC) was considered the most significant due to its location in relation to the 5' catalase intron splice site. In order to remove this sequence from the TYDV LIR, a new primer, LIR-Xho, was designed incorporating a XhoI site in place of the original PstI and NotI restriction sites.

Figure 9:
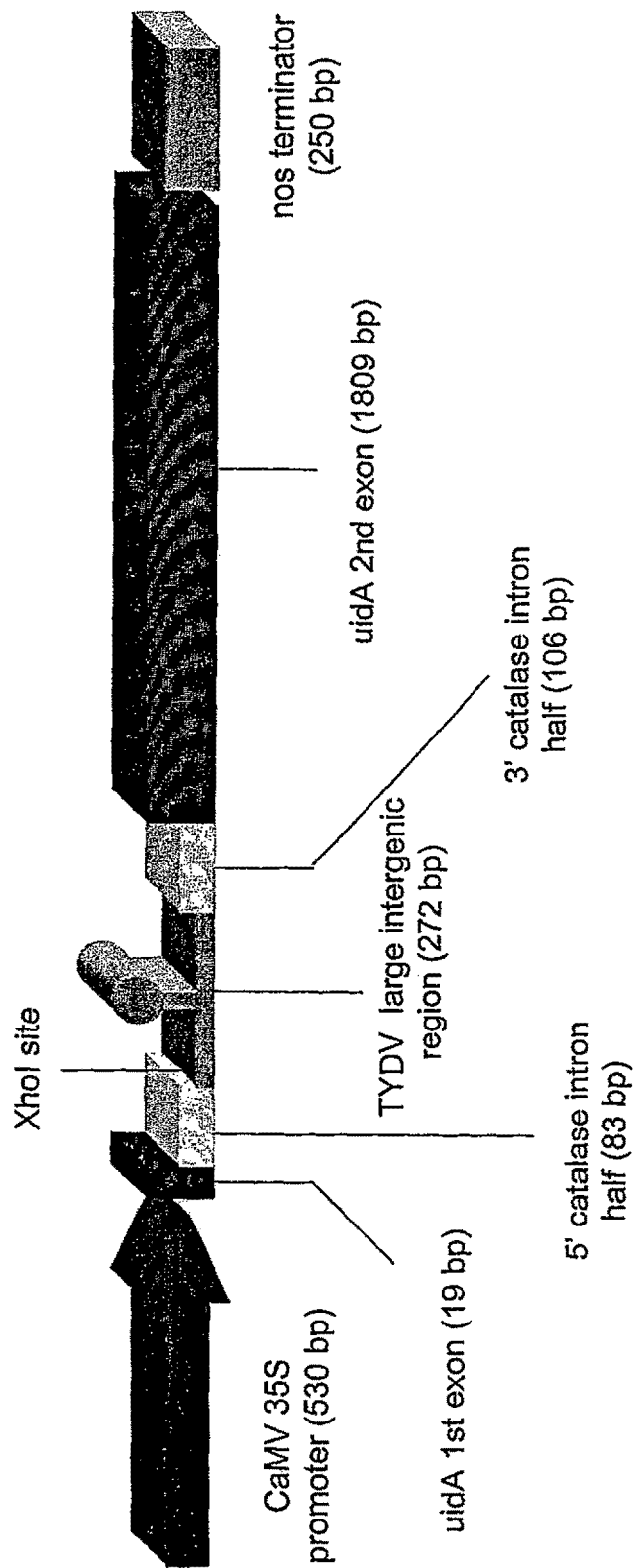

The TYDV LIR was re-amplified from pTEST1 plasmid DNA by PCR using primers LIR-Xho and LIR-R. This fragment was designated LIR-X. Similarly, the fragment comprising the CaMV 35S promoter (530 bp), uidA $1^{st}$ exon (19 bp) and 5' half of the catalase intron (83 bp) was re-amplified from pTEST1 plasmid DNA by PCR using primers FUP and CAT-Xho. This fragment was designated CAT-X. Both PCR products were cloned into pGEM-T and their sequences verified. Ultimately, PCR fragments were excised from pGEM-T (LIR-X using XhoI/SalI and CAT-X using PstI/XhoI) and ligated into PstI/SalI digested pTEST1, to replace the original inserts. This construct was designated pTEST2 (FIG. 9).

Removal of the cryptic intron splice site in pTEST2 generated higher levels of GUS expression than pTEST1 due to a reduction in aberrant splicing and improved mRNA processing.
Primers:

```
LIR-Xho
5'-CTCGAGATTAAGGCTCAAGTACCGTA-3'   [SEQ ID NO: 28]

CAT-Xho
5'-AGTTTAAAGAAAGATCAAAGC-3'        [SEQ ID NO: 29]

FUP
5'-AATTAACCCTCACTAAAGGG-3'         [SEQ ID NO: 30]
```

(f) Construction of the Rep-Activatable GUS Expression Vector

A 229 by fragment incorporating the TYDV small intergenic region (SIR) (nt +1275 to nt +1504) was amplified from TYDV-infected tobacco leaf tissue by PCR using primers SIR-F and SIR-R (see FIG. 2). The resulting PCR product was cloned into pGEM-T and the nucleotide sequence verified. This plasmid was designated pGEM-SIR. The TYDV SIR was excised from pGEM-SIR as a SphI fragment and inserted into the unique SphI site, downstream of the nos terminator, in pTEST1. This construct was designated pTEST1-SIR.
Primers:

```
SIR-F
                                    [SEQ ID NO: 31]
5'-GCATGCAAGAGTTGGCGGTAGATTCCGCATGT-3'

SIR-R
                                    [SEQ ID NO: 32]
5'-GCTCTTCGCGGCCGCGCTCCTGAATCGTCGAGTCA-3'
```

Figure 10:
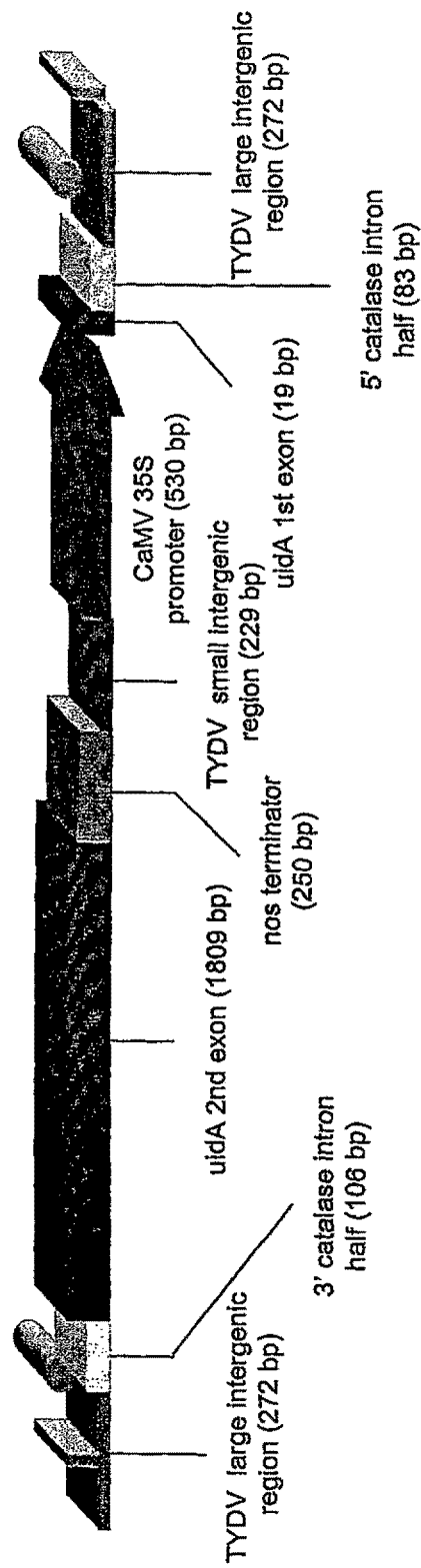
Figure 11:
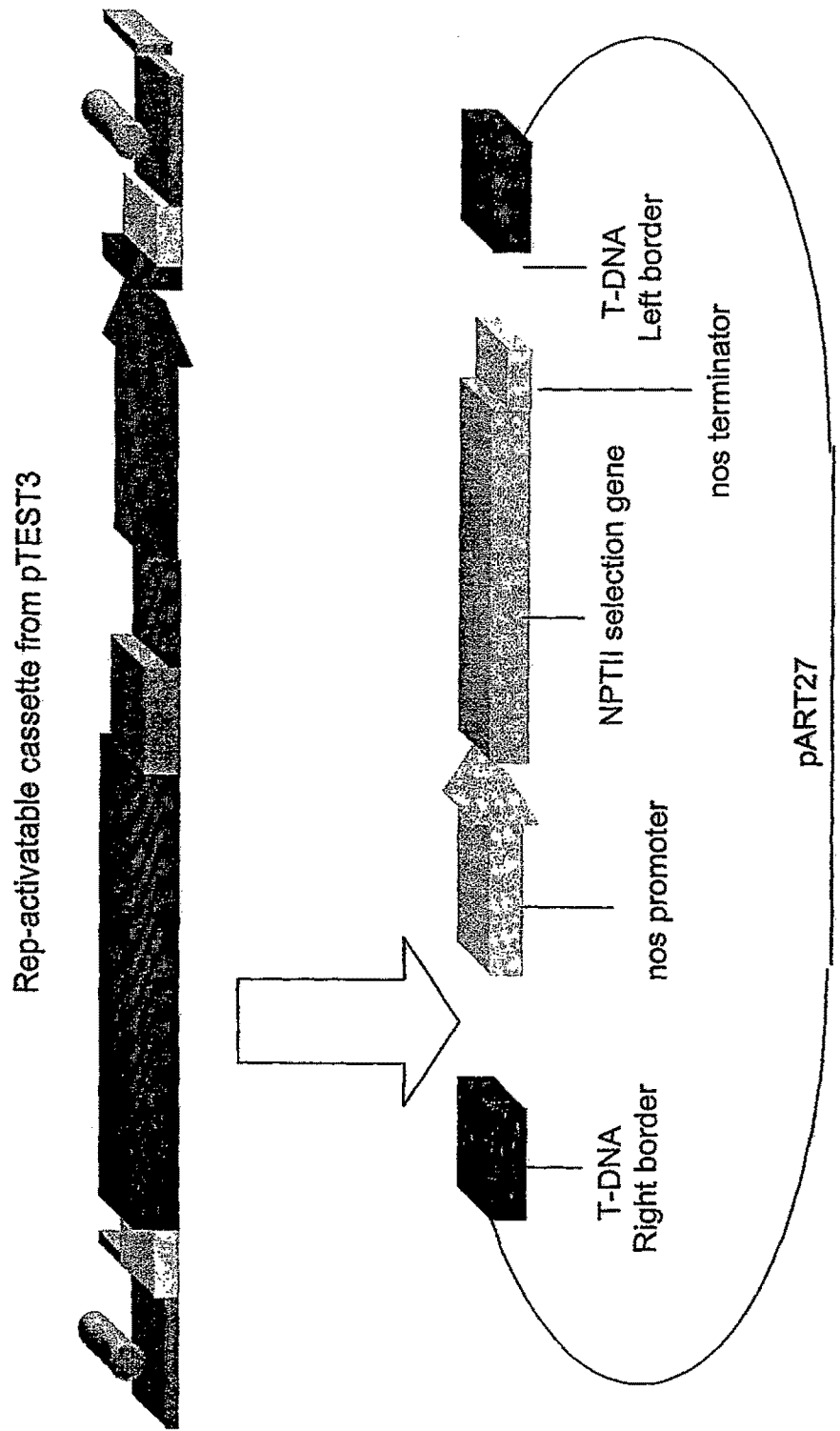

The CaMV 35S promoter, uidA exon, catalase intron 5' half, and TYDV LIR were excised from pTEST2 as a NotI/SalI fragment and inserted into a similarly-digested pGEM-T vector. The subsequent clone was designated pGEM-CATX. The TYDV catalase intron 3' half, uidA $2^{nd}$ exon, nos terminator, and TYDV SIR were excised from pTEST1-SIR as a NotI fragment and inserted into the unique NotI site in pGEM-CATX. This construct was designated pTEST3 (FIG. 10). The activatable GUS expression cassette was subsequently excised from pTEST3 by SacI/ApaI digestion, and inserted into the SacI/ApaI restriction sites located upstream of the nos pro-NPTII-nos ter cassette in the binary plasmid pART27 (cleave 1992). This construct was designated pTEST4 (FIG. 11). The vector pTEST4 was introduced into *Agrobacterium tumefaciens* (LBA4404) by electroporation using the method of Singh et al. (1993).

(g) Construction of the Infectious TYDV 1.1mer

Figure 12:
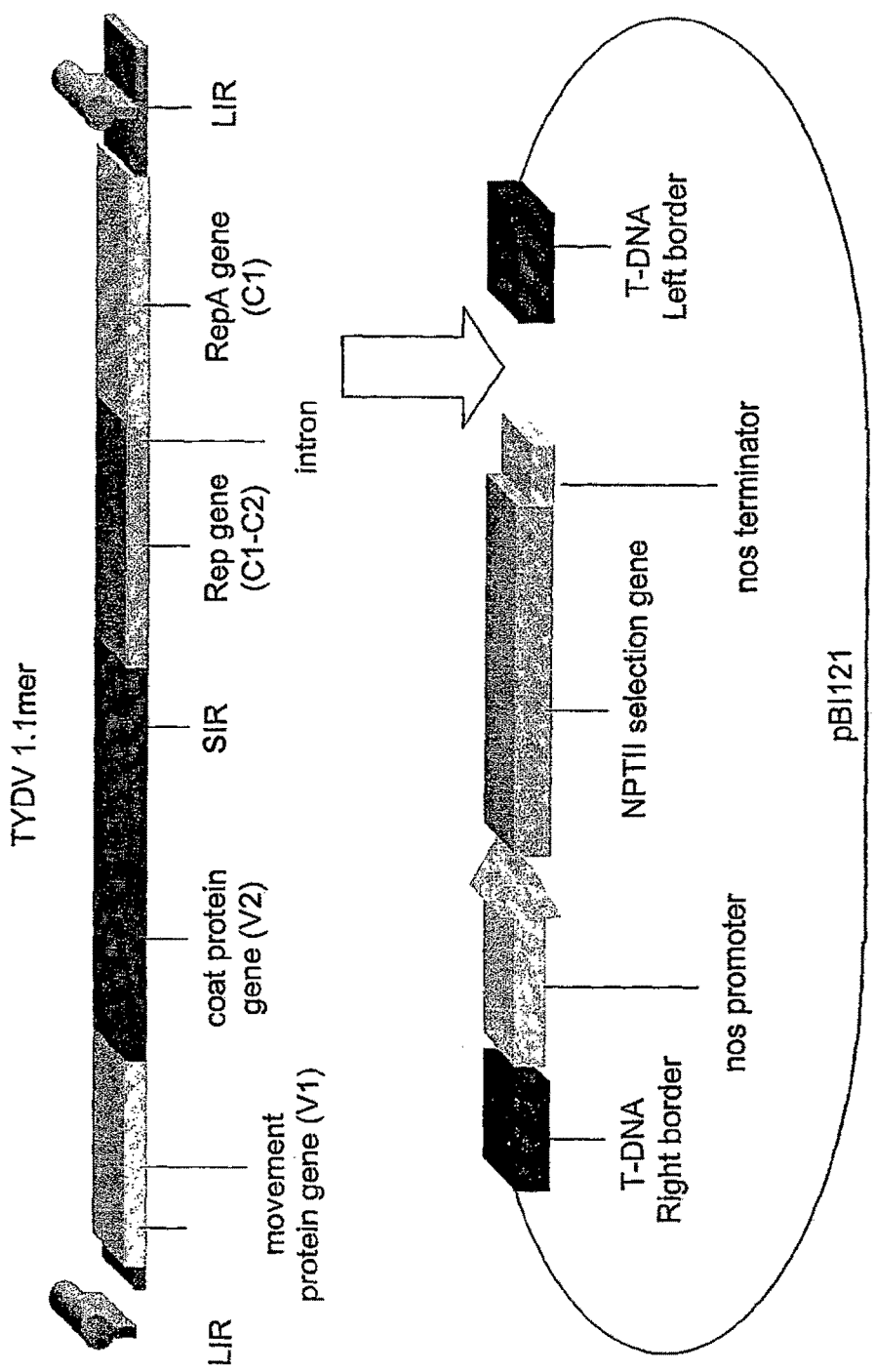

Two overlapping fragments of the TYDV genome were amplified from TYDV-infected tobacco leaf tissue by PCR using primer pairs LIR-F/SIR-R (SEQ ID NO:19/SEQ ID NO:32) and LIR-R/TYD-3F (SEQ ID NO:20/SEQ ID NO:33). The resulting PCR products (TYD-R and TYD-L, respectively) were cloned into pGEM-T and their sequences verified. These plasmids were designated pGEM-TYD-R and pGEM-TYD-L, respectively. A 1659 by fragment of the TYDV genome was excised from pGEM-TYD-L by digestion with EcoRI, and inserted into the unique EcoRI site in pGEM-TYD-R. This construct was designated pGEM-TYDV1.1mer. The TYDV 1.1mer was excised from pGEM-TYDV1.1mer by SalI/EcoRI partial digestion and inserted into similarly digested pBI101.3 vector (Clontech), to replace the uidA gene and nos terminator. This construct was designated pBI-TYDV1.1mer (FIG. 12). The vector pEI-TYDV1.1mer was introduced into *Agrobacterium tumefaciens* (LBA4404) by electroporation using the method of Singh et al. (1993).
Primers:

```
TYD-3F
5'-TTTAAACGTTTAGGGGTTAGCA-3'       [SEQ ID NO: 33]
```

(h) Construction of the CaMV 35S-TYDV Rep Fusion

Figure 13:
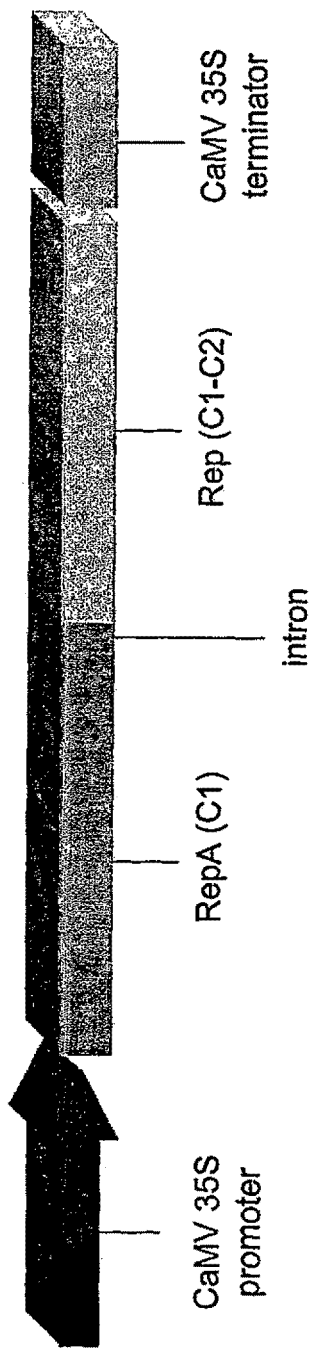

The complete Rep (including RepA) gene of TYDV (nt +2580 to nt +1481) was amplified from TYDV-infected tobacco leaf tissue by PCR using primers TYDVRepF and TYDVRepR. The resulting PCR product was directly cloned into the SmaI site located between the CaMV 35S promoter (530 bp) and CaMV 35S terminator (200 bp) in pDH51 (Pietrzak et al., 1986). This construct was designated p35S-Rep (FIG. 13).
Primers:

```
TYDVRepF
5'-TCAGTGACTCGACGATTC-3'           [SEQ ID NO: 34]

TYDVRepR
5'-TTAATATGCCTTCAGCCC-3'           [SEQ ID NO: 35]
```

Example 3

GUS Expression Assays Using TYDV Vectors (a) Transient Rep-Activated Expression of GUS in Dicot and Monocot Cells Tobacco (NT-1) cells are maintained essentially as described by An (1985), and prepared for microparticle bombardment as detailed by Dugdale et al. (1998). Banana (*Musa* spp. Cv. "Ladyfinger" AAA) embryogenic cell suspensions were prepared as previously described. Coating of gold particles and biolistic parameters were essentially as described by Dugdale et al. (1998) or Becker et al. (2000).

Plasmids used for this study included:—
(i) p355-2301 as positive control (FIG. 7),
(ii) pTEST3 (FIG. 10),
(iii) p355-Rep (FIG. 13), and
(iv) pTEST3 and p35S-Rep.

Five plates of both cell lines are bombarded for each of the four plasmid combinations. Cells are harvested three days post-bombardment and GUS activity assayed histochemically and/or fluorometrically (Jefferson et al., 1987).

No endogenous GUS activity is observed in non-bombarded cells. Strong GUS activity, evident as bright blue staining cell foci, is observed from cells bombarded with the positive control plasmid p35S-2301. No GUS expression is observed from cells bombarded with either p35S-Rep or pTEST3. In contrast, cells bombarded with both p355-Rep and pTEST3 stain intensely blue, greater than that obtained with the positive control plasmid p358-2301. This result suggests that only upon addition of the TYDV Rep in trans does the GUS expression cassette in pTEST3 become activated.

(b) Detection of Rep-Assisted Nicking, Joining and Replication of the GUS Multicopy Plant Episome (MPE)

Detection of the TYDV-based GUS MPEs is achieved using a PCR approach. Primers uidA1 (SEQ ID NO:25) and uidA3 (SEQ ID NO:27) amplify a fragment of the uidA gene spanning the catalase intron. Only upon Rep-assisted release of the TYDV-based MPE from the plasmid pTEST3 does this primer combination generate a 600 by product (including 140 by of the uidA gene, 190 by of the catalase intron and 270 by of the TYDV LIR) in a PCR.

Figure 7:
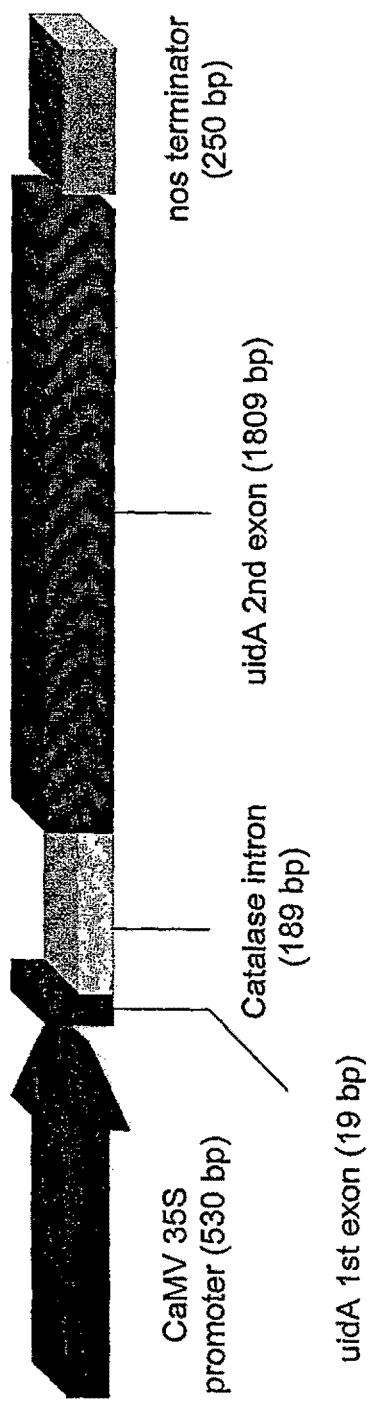

Tobacco NT-1 and banana cells are bombarded with each of the four plasmid combinations listed above. Three days post-bombardment, cells are harvested and total gDNA extracted using the method of Stewart and Via (1993). Total gDNA (1 µg) is used as a template for a PCR with primers uidA1 (SEQ ID NO:25) and uidA3 (SEQ ID NO:27). PCR products are electrophoresed through a 1.5% w/v agarose gel. A 330 by product is obtained from gDNA of cells bombarded with the control plasmid p358-2301 (FIG. 7). This product corresponded to the uidA and catalase intron sequence from the input plasmid DNA. No PCR product is obtained from gDNA of non-bombarded cells, or cells bombarded with pTEST3 or p35S-Rep alone. A 600 by product is obtained from gDNA of cells bombarded with both pTEST3 and p35S-Rep. This result supports previous GUS histochemical assays and suggests the TYDV-based MPEs are only generated in cells bombarded with both pTEST3 and p358-Rep.

Replication of the TYDV-based MPEs is assessed by Southern hybridization. Using this approach, multimeric forms of the MPE, indicative of rolling circle replication, are detected by hybridisation. Total gDNA (20 ug) from cells bombarded with each of the four plasmid combinations, are electrophoresed through a 1.5% w/v agarose gel. DNA is transferred to a nylon membrane (Roche) by the method of Southern (1975). A 600 by DIG-labelled probe, specific for the uidA and catalase intron, is amplified by PCR using primers uidA1 (SEQ ID NO:25) and uidA3 (SEQ ID NO:27). The uidA-specific probe is hybridised with the nylon membrane at 42° C. in DIG Easy-Hyb solution (Roche) and signal detected using CDP-Star substrate (Roche) according to manufacturer's instructions. Characteristic supercoiled, linear, and open circular forms and higher molecular weight multimeric forms of the TYVD-based MPEs are only detected in gDNA from plant cells bombarded with both pTEST3 and p35S-2301. Together these results confirm that, when provided in trans, the TYDV Rep is capable of nicking, joining, and replicating the TYDV-based AVE in both monocotyledonous and dicotyledonous cell types. Further, these results suggest that uidA expression from the plasmid pTEST3 is only activated upon addition of the TYDV Rep, and the addition results in significantly higher expression than a non-replicating GUS expression cassette (p35S-2301).

Example 4

Stable Transformation of a Monocotyledonous and a Dicotyledonous Plant with the Rep-Activatable Cassette Banana (*Musa* spp. Cv. "Ladyfinger" AAA) embryogenic cell suspensions are targeted for microprojectile-based stable transformation. Cells are bombarded with pTEST3, as previously described, except the plasmid is co-transformed with 1 ug of pDHKAN (Pietrzak et al., 1986). This plasmid contains a CaMV 35S pro-NPTII-CaMV 35S ter cassette, from which expression of the NPTII gene confers resistance to the antibiotics kanamycin or geneticin. Selection, culturing and regeneration of transgenic banana plants are done essentially as described by Becker et al. (2000). Independent transgenic plants are confirmed to contain both the NPTII and uidA genes by PCR, using primer pairs NPT-F/NPT-R and uidA4/uidA5, respectively. Ten independent transformants are selected for further studies.

Primers:

```
NPT-F
5'-ATGATTGAACAAGATGGATT-3'         [SEQ ID NO: 36]

NPT-R
5'-TGAGAAGAACTCGTCAAGA-3'          [SEQ ID NO: 37]

uidA4
5'-GTTATTGCCGGGAAAAGTGTACGTA-3'    [SEQ ID NO: 38]

uidA5
5'-CTAGCTTGTTTGCCTCCCTGCTGCG-3'    [SEQ ID NO: 39]
```

Tobacco (*Nicatiana tabacum* cv. "Samsun") is transformed by *Agrobacterium*-mediated infection of leaf discs according to the method of Horsch et al. (1988). Ten independent transgenic plants are transformed with T-DNA from the plasmid pTEST4. Each line is shown to contain the NPTII and uidA coding regions by PCR, as described above.

Leaf pieces from each of the ten transgenic banana and tobacco lines transformed with the Rep-activatable GUS expression cassette (i.e. pTEST3 [FIG. 10] and pTEST4 [FIG. 11], respectively) are bombarded with the plasmid p355-Rep. Three days post-bombardment, leaf pieces are subjected to GUS histochemical assays. No GUS expression is evident in unshot leaf pieces from each of the ten banana and tobacco lines. Leaf pieces, bombarded with the plasmid p35S-Rep, display multiple blue GUS-staining foci. Rep-directed nicking, joining, and replication of the TYDV based MPEs is confirmed in these leaf pieces, as described previously. These results indicate the TYDV Rep is capable of activating GUS expression from a stably integrated copy of either plasmid, and able to nick, join and replicate the TYDV-based MPE in vivo.

Example 5

TYDV-Infection Activated Expression in Transgenic Tobacco

Each of the 10 transgenic tobacco lines is infiltrated with *Agrobacterium* cultures transformed with pBI-TYDV1.1mer (refer to Example 2(f), FIG. 12) using the method of Boulton (1995). Over a two month period, samples are taken from the point of infection and throughout the plant, and GUS expression assessed using histochemical assays. GUS activity (i.e. blue staining tissue) is only noted in TYDV-infected plants, compared to mock-inoculated controls. Over time, GUS expression spreads, via the vasculature, from the initial point of infection to various plant parts. Rep-directed nicking, joining and replication of the GUS expression cassette is established as previously described. This result suggests that TYDV infection is sufficient for replicative release of the GUS expression cassette from an integrated chromosomal copy.

Example 6

Transient Cell-Death Assays Using Expression Vectors Based on BBTV

Figure 14:
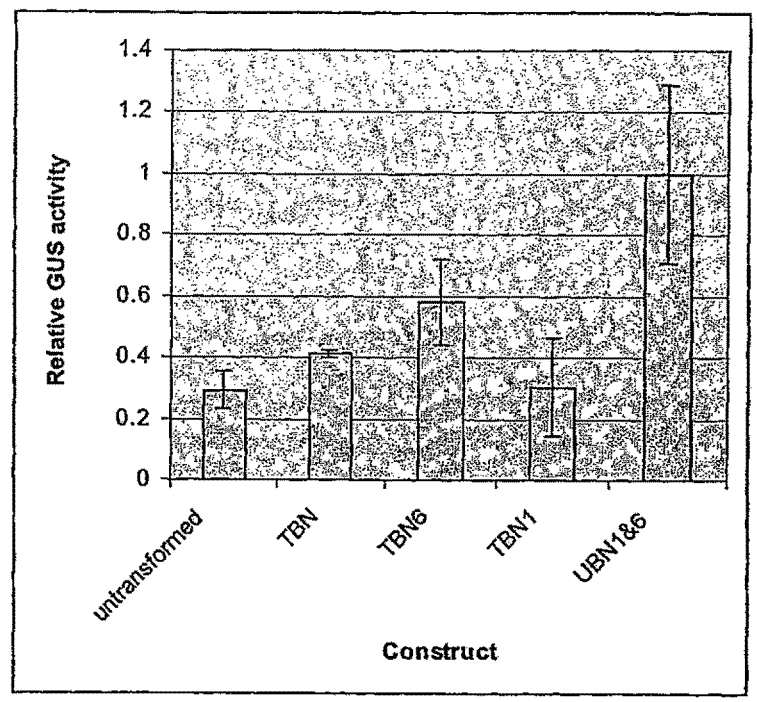
Figure 15:
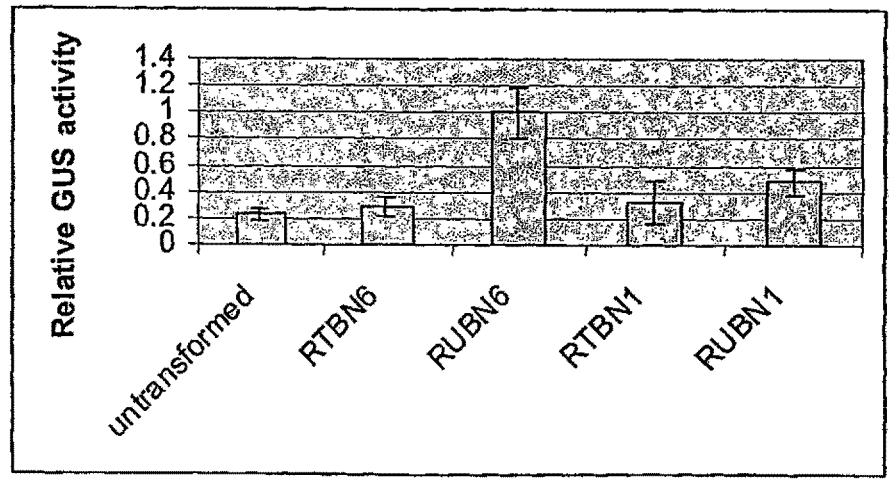
Figure 16:
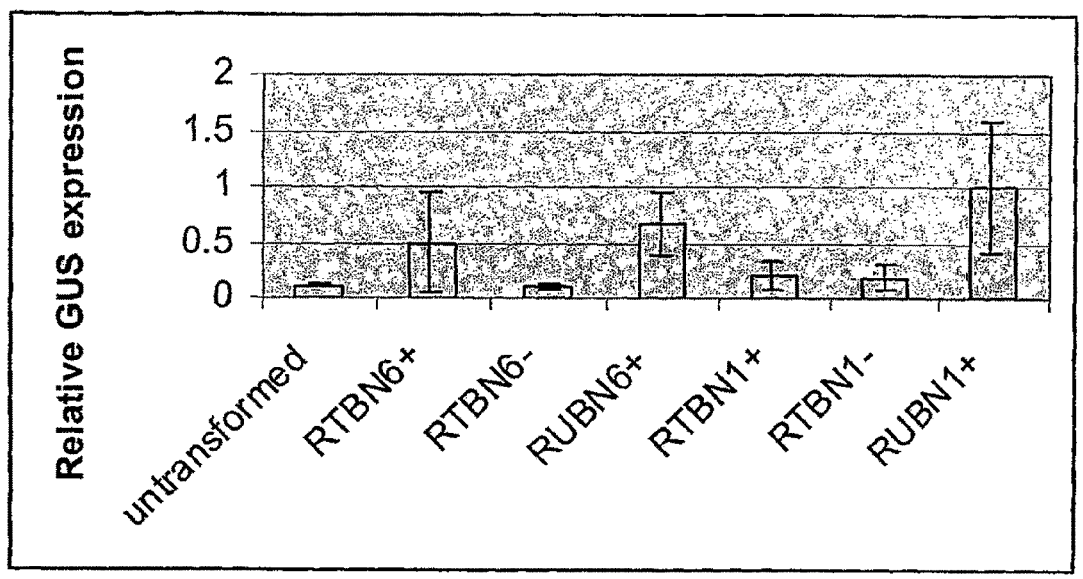

To demonstrate that barnase was capable of causing cell death, assays were carried out with the expression vectors (pTBN, pTBN6, pTBN1, FIGS. 1, 2 and 3). Negative controls were pUBN6 and pUBN1 (refer to Example 1, above). Each of these constructs was co-bombarded with a GUS vector into banana (*Musa* spp cv. Bluggoe) embryogenic cell suspensions essentially as described by Dugdale et al, 1998. The GUS vector contained a strong promoter (maize Ubi1, CaMV 35S or banana Act1 driving the expression of the reporter gene β-glucuronidase (Jefferson, 1987). Subsequent MUG assays for GUS activity showed that cells which were transformed with either pTBN, pTBN6 or pTBN1 had lower GUS activity than did the negative control (pUBN1 or pUBN6) (FIG. 14). This suggests that intron splicing is still occurring, and at least in the case of pTBN1, does not differ significantly from the original pTBN vector. Thus, the inclusion of the BBTV replication elements into the intron did not significantly decrease the splicing efficiency or subsequent activity of barnase, relative to pTBN.

Figure 17:
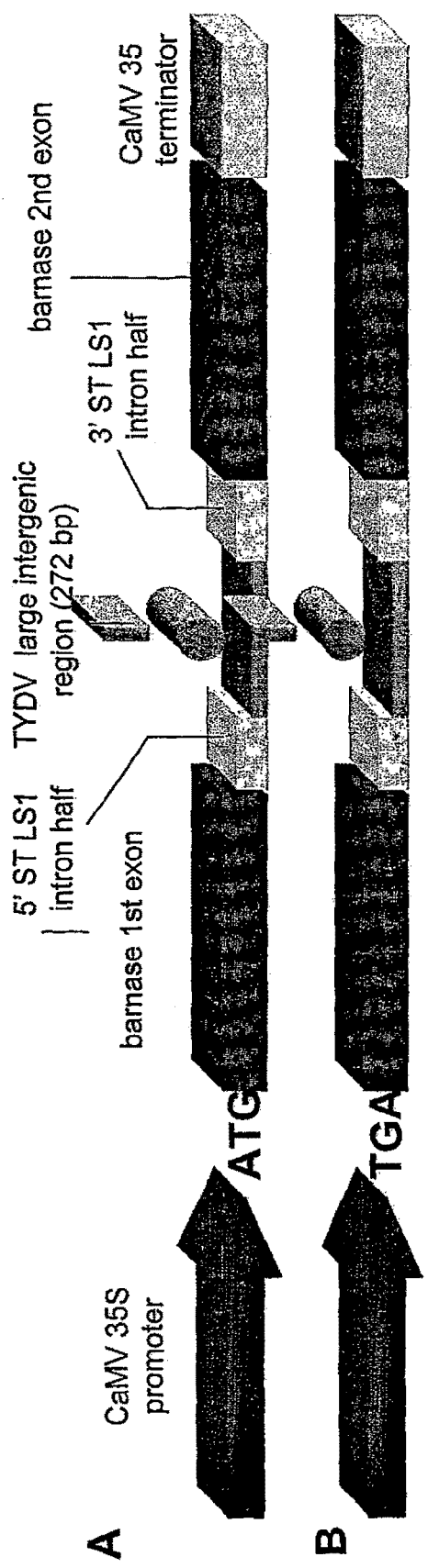
Figure 18:
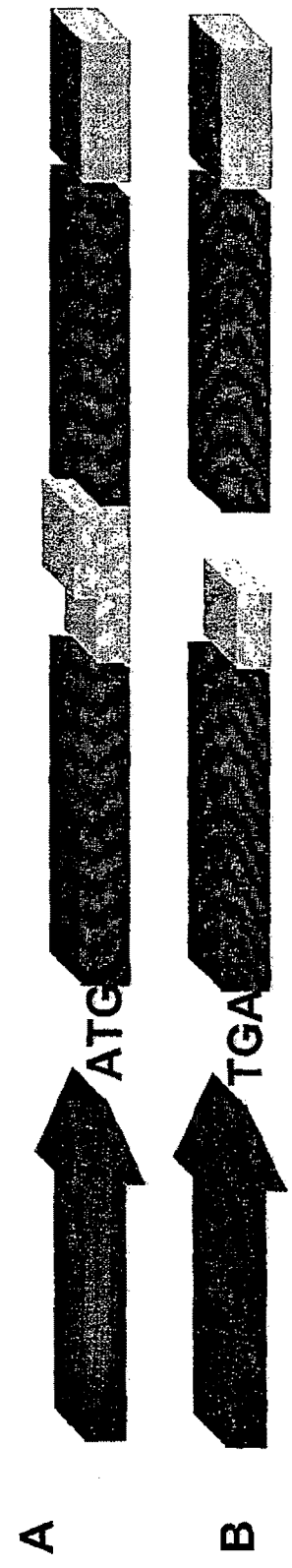

Experiments were conducted that show and pBUTR-LIR, respectively. The LIR-containing barnase genes in pBTR-LIR and pBUTR-LIR were excised as BamHI/PstI fragments and inserted into similarly-digested pGUS2 vector to replace the original uidA coding region. Plasmid pGUS2 contains a CaMV35S pro (530 bp)-uidA gene-CaMV 35S ter (200 bp). These constructs were designated p35S-BTR-LTR and p35S-BUTR-LIR, respectively (FIG. 17). Two control plasmids were constructed by excision of the barnase genes from pGEM-BTR and pGEM-BUTR with BamHI/PstI, and insertion into similarly digested pGUS2. These control plasmids were designated p35S-BTR and p35S-BUTR, respectively (FIG. 18).

(b) Transient Assessment of TYDV Rep-Activated Barnase Activity in Monocotyledonous and Dicotyledonous Cells In order to determine barnase activity in vivo, suicide constructs are co-bombarded with a green fluorescent protein (gfp) expression cassette. Barnase expression and action (i.e. cell death) is considered to occur when a significant reduction in green fluorescent foci is observed in comparison to the untranslatable barnase controls.

Banana (*Musa* spp. Cv. "Ladyfinger") and tobacco (*Nicotiana tabacum* NT-1) cells are bombarded with plasmids (i) p35S-BTR, (ii) p35S-BUTR, (iii) p35S-BTR-LIR, and (iv) p35S-BUTR-LIR (FIGS. 17 and 18) as described in Example 3, above. Each plasmid is co-bombarded with 1 ug of pWORM. The construct pWORM contains a CaMV 355 pro (530 bp)-gfp (750 bp)-CaMV 35S ter (200 bp) cassette and has previously been shown to provide strong green fluorescence in transient assays with both cell types (Dugdale et al., 1998).

Three days post-bombardment, green fluorescence is visualised using a Leica MZ12 stereo microscope with GFP-Plus fluorescence module (excitation=490, emission=510). Both p35S-BTR and p35S-BTR-LIR significantly reduce gfp expression from pWORM (as determined by the number and intensity of green fluorescent foci) in comparison to p355-BUTR and p35S-BUTR-LIR. This result suggests that insertion of the TYDV LIR into the ST LS1 intron within p355-BTR does not interfere with intron processing nor inhibit barnase expression.

(c) Construction of the TYDV Rep-Activatable Barnase Vector

Figure 19:
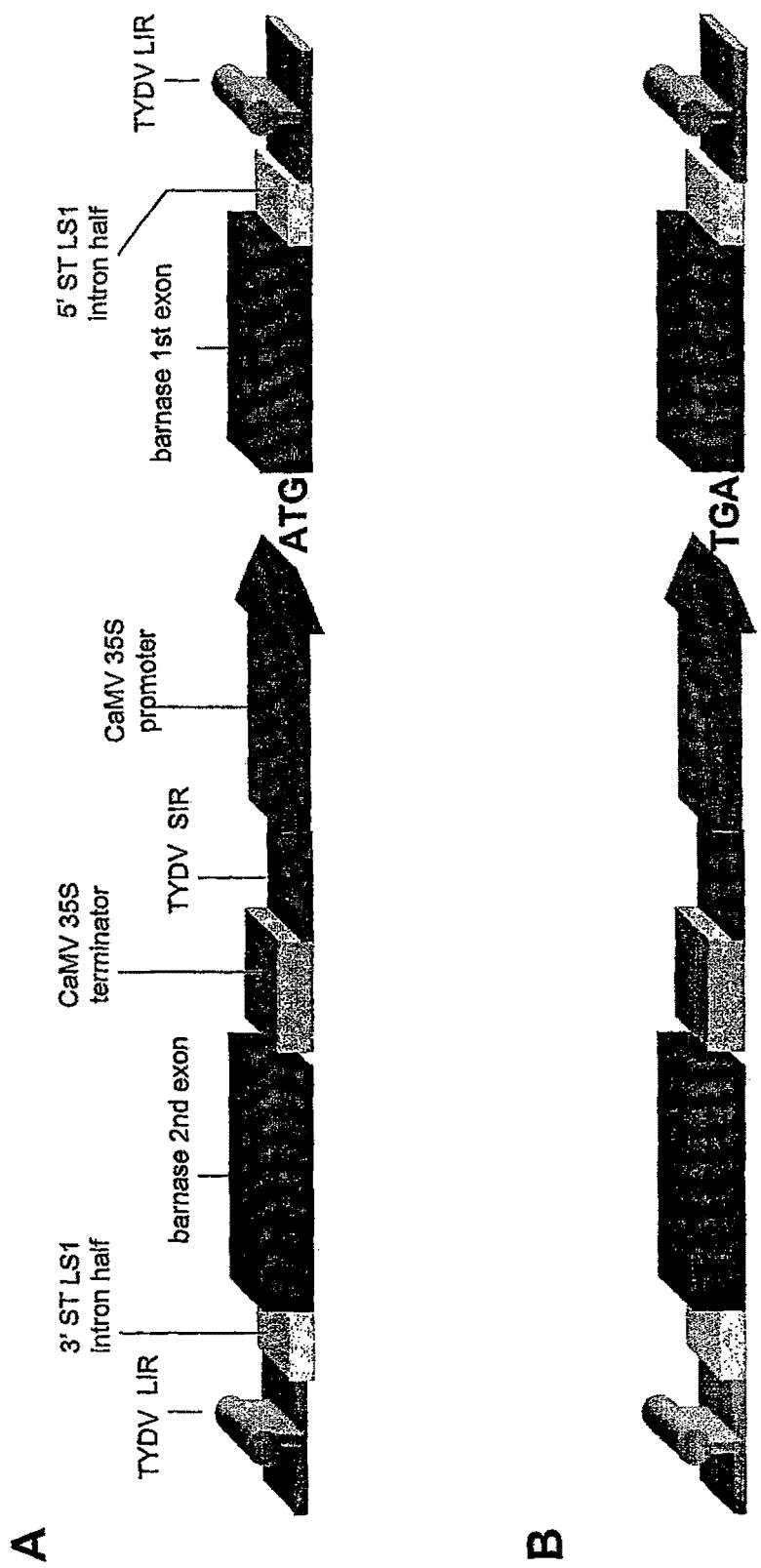

The CaMV 35S promoter, barnase 5' gene half, ST LS1 5' intron half and TYDV LIR are re-amplified from p35S-BTR-LIR (FIG. 17A) by PCR using primers 35S-IE (SEQ ID NO:21) and LIR-R (SEQ ID NO:20). The PCR product is cloned into pGEM-T vector and sequence-verified. This plasmid is designated pGEMB5'. The TYDV LIR, ST LS1 3' intron half, barnase 3' gene half and nos terminator is excised from p35S-BTR-LIR as a XhoI/SacI fragment, the TYDV SIR is excised from pGEM-SIR as a SacI/NcoI fragment, and the CaMV 35S promoter, barnase 5' gene half, ST LS1 5' intron half and TYDV LIR are excised from pGEMB5' as a NcoI/SacII partial fragment. Inserts are ligated together with XhoI/SacII digested pBluescript II (Stratagene). The resulting construct is designated pBTR.test1 (FIG. 19A). The untranslatable control vector is similarly prepared and the resulting construct designated pBUTR.test1 (FIG. 19B).

(d) Transient TYDV Rep-Activated Barnase Expression in Monocot and Dicot Cells.

Banana (*Musa* spp. Cv. "Ladyfinger") and tobacco (*Nicotiana tabacum* NT-1) cells are bombarded, as described above, with the plasmid combinations listed in Table 4, below:—

TABLE 4

Plasmid combinations for transient transformation assays in banana and tobacco cells, and there resulting gfp expression (asssessed as + or −)

| | Plasmid combination | | | | | |
|---|---|---|---|---|---|---|
| | p35S-BTR pWORM | p35S-BUTR pWORM | pBTR-test1 pWORM | pBUTR-test1 pWORM | pBTR-test1 pWORM p35S-Rep | pBUTR-test1 pWORM p35S-Rep |
| Green fluorescent foci 3 days post-bombardment | no | yes | yes | yes | no | yes |

Results in Table 4 suggest that barnase expression (and therefore cell death) is only activated from pBTR-test1 when the TYDV Rep is supplied in trans. Rep-activated expression of the untranslatable barnase gene cassette (pBUTR-test1) results in no significant reduction in gfp expression from pWORM. Rep-assisted nicking, joining, and replication of the MPEs from cells bombarded with pBUTR-test1, pWORM, and p35S-Rep is confirmed as previously described, except primers BARN.UTR (SEQ ID NO:40) and BARN.EXP2 (SEQ ID NO:41) are used for PCR and a DIG-labelled barnase-specific probe is synthesised using the before-mentioned primers.

(e) Construction of Binary Plasmids Containing the Rep-Activatable Barnase Gene Cassettes Rep-activatable barnase cassettes are excised from pBTR-test1 and pBUTR-test1 as PvuII fragments and inserted into the unique EcoRI site (blunt ended using DNA polymerase I large Klenow fragment) located downstream of the CaMV 35S pro-NPTII-CaMV 35S ter cassette in the binary plasmid pTAB5 (CSIRO, Canberra, Australia). The resulting constructs are designated pTAB-BTR1 and pTAB-BUTR1, respectively. Both vectors are introduced into *Agrobacterium tumefaciens* (LBA4404) by electroporation using the method of Singh et al. (1993).

(f) Stable Transformation of a Monocotyledonous and a Dicotyledonous Plant with the Rep-Activatable Barnase Cassettes.

Stable transformation of banana (*Musa* spp. Cv. "Ladyfinger") and tobacco (*Nicotiana tabacum* cv. "Samsun") is done as described in Example 4, above, except plasmids pBTR-test1 and pBUTR-test1 are independently co-transformed with pDHKAN for stable banana transformation and *Agrobacterium* cultures harbouring the plasmids pTAB-BTR1 and pTAB-BUTR1 are used for *Agrobacterium*-mediated transformation of tobacco leaf disks.

Transformed plants are confirmed to contain the barnase gene cassettes and the NPTII gene by PCR using primer pairs LIR-F/LIR-R (SEQ ID NO:19/SEQ ID NO:20) and NPT-F/NPT-R (SEQ ID NO:36/SEQ ID NO:37), respectively. Ten independent transgenic lines of both monocotyl-edonous and dicotyledonous species are selected for further studies.

(g) Rep-Activated Hypersensitive Resistance to TYDV in Transgenic Tobacco

Rep-activation of barnase expression in the ten independent tobacco plants transformed with pTAB-BTR1 and pTAB-BUTR1 is initially tested by particle bombardment of the p35S-Rep construct into leaf pieces, as described. Two days post-bombardment, necrosis of bombarded areas is only evident on leaves of tobacco plants transformed with the Rep-activatable translatable barnase gene cassette (pTAB-BTR1) in comparison to the untranslatable control (pTAB-BUTR-1). This result suggests introduction of the TYDV Rep in trans is sufficient for replicative release of the barnase expression cassette from an integrated chromosomal copy. Rep-assisted nicking, joining, and replication is confirmed in leaf pieces of tobacco plants transformed with pTAB-BUTR1, as was described for the transient assays in NT-1 cells.

To demonstrate hypersensitive resistance to TYDV in transgenic tobacco, viruliferous leafhoppers (Orosius argentatus) are allowed to feed on plants for up to 2 days. Over the following week, plants are inspected for characteristic TYDV symptoms as described originally by Hill (1937). Plants transformed with the Rep-activatable, untranslatable barnase expression cassette (pTAB-BUTR1) produce typical TYDV symptoms, including dwarfing, yellowing, bending down of margins and tips of young leaves, and shortening of the internodes. In contrast, tobacco plants transformed with the Rep-aetivatable, translatable barnase expression cassette (pTAB-BTR1) display atypical necrotic lesions at the site of aphid feeding (most likely the result of barnase-induced cell death). These plants develop normally over the ensuing three months, in comparison to uninfected tobacco plants, and at no point develop symptoms characteristic of TYDV infection.

Total gDNA is isolated from leaves of each of the 20 transgenic tobacco plants and uninfected controls, two weeks post-infection, using the method of Stewart and Via (1993). Total gDNA (1 µg) is used as a template for a PCR with primers designed to the TYDV coat protein gene (CP-F and CP-R). The 765 by coat protein gene, and therefore virus genome, is only detected in tobacco transformed with pTAB-BUTR1. This result suggests that tobacco plants transformed with pTAB-BTR1 are resistant to TYDV infection and remain free of TYDV-induced symptoms over extended periods of time.

Primers:

```
CP-F
5'-ATGGCGGGCCGGTATAAGGGTTTGG-3'    [SEQ ID NO: 43]

CP-R
5'-TTATTGATTGCCAACTGATTTGAAAT-3'   [SEQ ID NO: 44]
```

Example 8 gfp Vector Constructions

Based on BBTV

A similar series of vectors, based on the Rep-activatable barnase cassettes, were constructed using the reporter gene encoding green fluorescent protein (GFP) and BBTV intergenic regions. Both expression and re-circularization vectors were constructed by overlapping PCR in a manner similar to that of the pRTBN series of vectors and cloned into a pUC19 vector. Primers used in the construction of these vectors are indicated in Table 5. In some cases plasmids pBN, pTBN6 and pTBN1 were used as templates for PCRs.

TABLE 5

Oligonucleotide sequences

| Primer | Name | Sequence (5'-3') |
|---|---|---|
| +1 | 35SH | AAGCTTCATGGAGTCAAAGA (SEQ ID NO: 45) |
| +2 | 5'mGFPBam | GGATCCATGAGTAAAGGAGAAGAACTT (SEQ ID NO: 46) |
| +3 | GFPB1 | AAGTCAAGTTTGAGGTAAGTTTCTGCTTC (SEQ ID NO: 47) |
| -3 | B2GFP | GAAGCAGAAACTTACCTCAAACTTGACTT (SEQ ID NO: 448) |
| +4 | B1GFP | TTGTTGATGTGCAGGGAGACACCCTCGTC (SEQ ID NO: 49) |
| -4 | GFPB2 | GACGAGGGTGTCTCCCTGCACATCAACAA (SEQ ID NO: 50) |
| -5 | 3'mGFPSac | GAGCTCTTATTTGTATAGTTCATCCAT (SEQ ID NO: 51) |
| -6 | NOS4-H | AAGCTTTTCGCCATTCAGGCTGC (SEQ ID NO: 52) |
| +7 | B3-6 | TATCATTAATTAGTAAGTTGTGCTGTAA (SEQ ID NO: 53) |
| -8 | B4-6 | AATATTATATTACTCGCTTCTGCCTTCC (SEQ ID NO: 54) |
| +9 | B5-I | ATCATTAATTAGTCACACTATGACAAAAG (SEQ ID NO: 55) |
| -10 | B6-I | AATATTATATTACTGATGCAAATGTCCCCG (SEQ ID NO: 56) |

Figure 20:
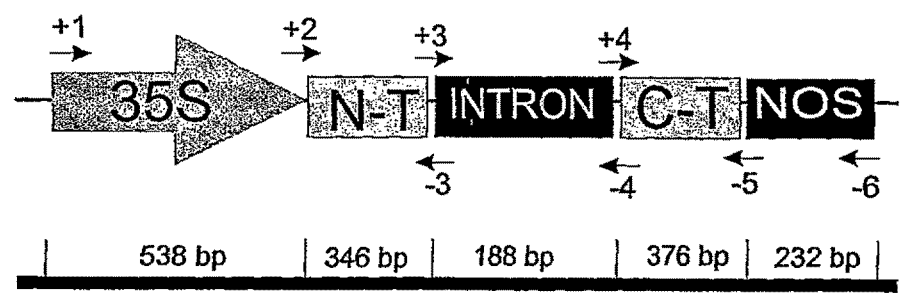
Figure 21:
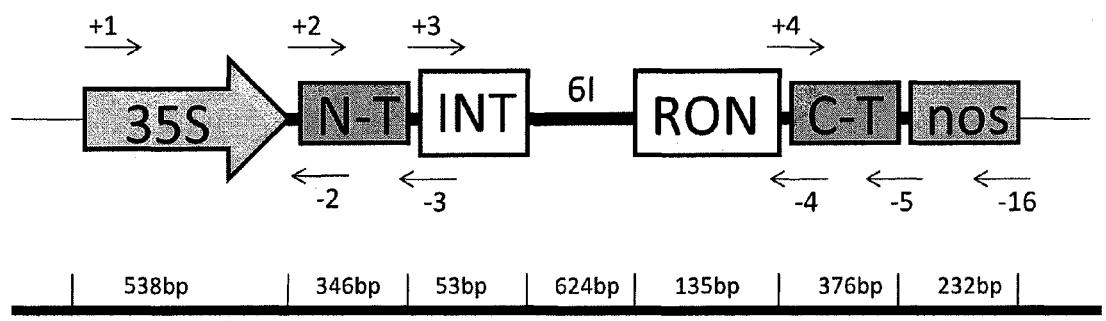
Figure 22:
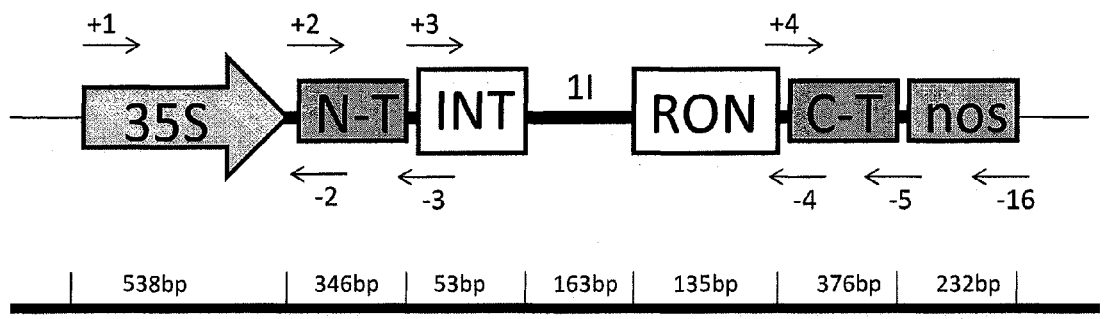
Figure 23:
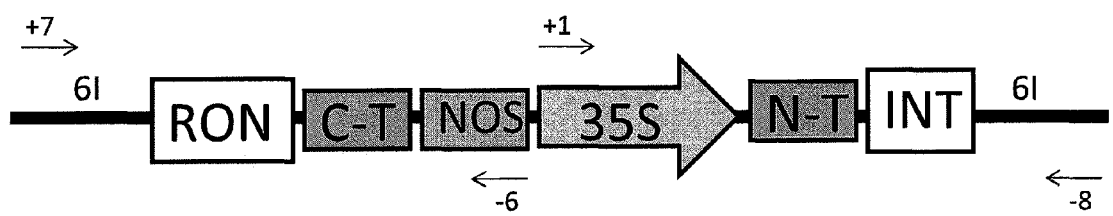
Figure 24:
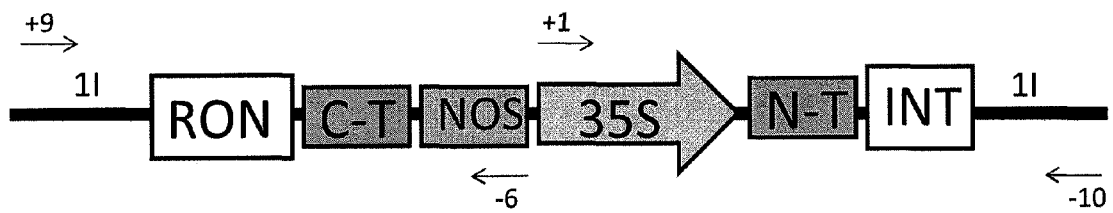
Figure 25:
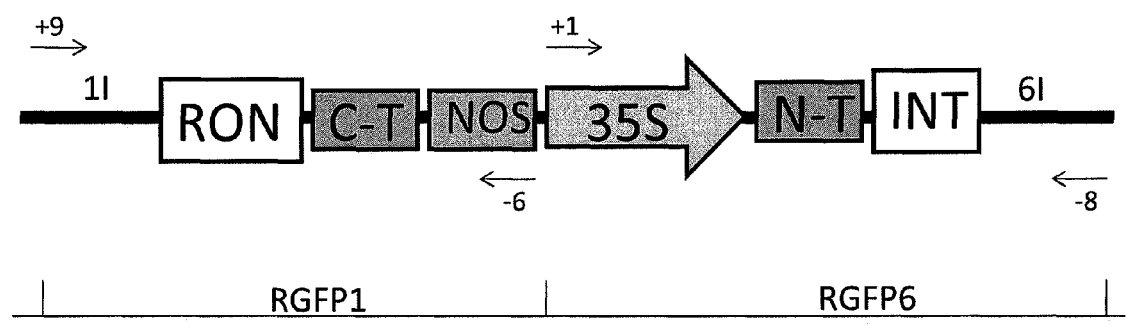
Figure 26:
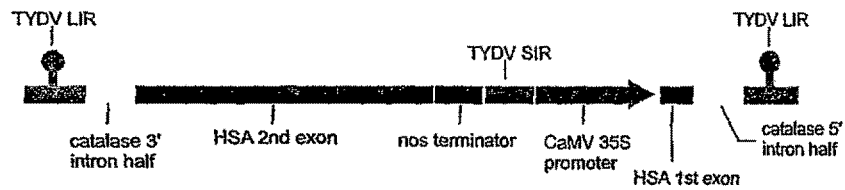
Figure 26:
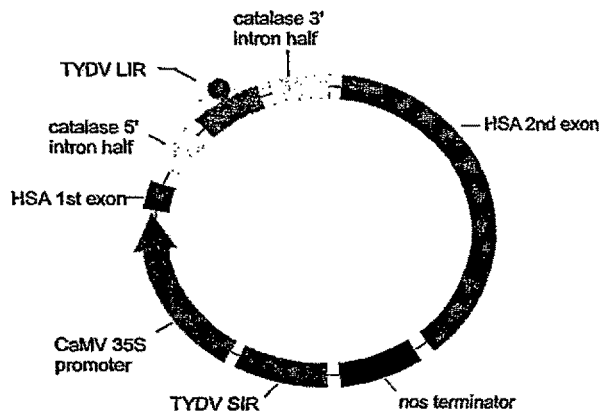
Figure 26:
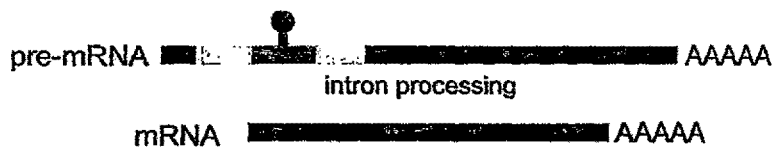

Initially, plasmids pGI (SEQ ID NO:69), pGI6 (SEQ ID NO:70), pGI1 (SEQ ID NO:71) were constructed and are shown in FIGS. 20, 21 and 22, respectively. Ultimately, plasmids pRGI6, pRGI1, pRGI1/6 were constructed and are shown in FIGS. 23, 24 and 25, respectively. In FIGS. 20 to 25, intron refers to the potato ST-LS1 intron, intergenic regions are derived from either BBTV DNA-1 or -6, and CT and NT refer to the C-terminal and N-terminal portions of the GFP reporter gene.

The efficacy of these various constructs is assessed in transient assays via micro-projectile bombardment of banana cell suspensions. The first transient assays, measure GFP expression to determine whether the various monomers are replicatively released and re-circularized, and that the GFP gene is transcribed, processed and expressed correctly. A BBTV DNA-1 1.1 mer is mixed in equimolar amounts of either pGI1 or pGI6 and bombarded into banana embryogenic cell suspensions. Eight days post-bombardment, replicative release and circularization are assayed by Southern hybridization, using a GFP-specific probe. GFP expression is monitored using a GFP microscope and quantified using Western blot analysis and a GFP-specific antisera.

Southern hybridization indicates the presence of monomeric circular molecules from either pGI1 or pGI6P only when the BBTV DNA-1 1.1mer is delivered in trans. Similarly, GFP expression is only detected, when the viral-derived 1.1 mer is present.

Example 9

Stable Transformation of Banana for Barnase-Induced Resistance to BBTV

Banana embryogenic cell suspensions of both Bluggoe and Cavendish are co-transformed with pRTBN6 and a plasmid carrying the selectable marker gene using microprojectile bombardment (Becker et al., 2000). Regenerated plantlets are assayed by PCR to determine whether a complete copy of the Rep-activatable barnase cassette has been incorporated into the banana genome. Positive transformants are multiplied and, initially five plants from each transformation are challenged with 20 BBTV viruliferous aphids. Southern hybridization analyses are used to compare levels of viral DNA accumulation between transformed and non-transformed plants. Promising transgenic lines are further multiplied, re-challenged and assayed.

In nearly all cases, transgenic banana plants show no evidence of banana bunchy top disease, in comparison to controls. Rather, atypical necrosis at the point of aphid feeding is observed, most likely reflecting barnase-induced cell death. Using PCR and Southern hybridisation the coat protein gene of BBTV can not be detected in any plant part tested, suggesting these lines are resistant to BBTV infection, replication and spread.

Example 10

Tissue-Specific and Inducible Rep-Activated Expression

Based on TYDV

In order to control the site of Rep expression, and therefore transgene activation/replication in planta, tissue-specific promoters were employed.

(a) Constitutive Expression

The vector pTAB16 contains a CaMV 35S pro-bar selection gene-ocs ter and CaMV 35S pro-uidA-CaMV 35S ter cassettes located between the right and left T-DNA borders in pBIN16. The CaMV 35S-TYDV Rep gene cassette is excised from p35S-Rep by EcoRI/BamHI digestion and inserted into similarly digested pTAB16 vector to replace the original CaMV 35S-uidA cassette. This construct is designated pTAB-TYDV-Rep.

(b) Seed-Specific Expression

The 1 kb rice glutelin promoter (Genbank Accession X52153) has been shown to direct seed-specific reporter gene expression in tobacco (Leisy et al., 1989). The rice glutelin promoter is excised from the plasmid pGT3-JEFLK (Miller, 2001) by NcoI digestion and ligated into similarly digested pTAB-TYDV-Rep vector to replace the original CaMV 35S promoter. This construct is designated pGL-TYDV-Rep.

(c) Root-Specific Expression

The 880 by *Arabidopsis thaliana* root-specific kinase homolog (ARSK1) promoter (Genbank Accession L22302) has been shown to direct tissue-specific uidA reporter gene expression in epidermal, endoepidermal, and cortex regions of *A. thaliana* roots (Hwang and Goodman, 1995). The ARSK1 promoter is amplified from *A. thaliana* gDNA by PCR using primers ARSK-F and ARSK-R. The resulting PCR product is cloned into pGEM-T and the sequence verified. The ARSK1 promoter is excised from pGEM-T by NcoI digestion and ligated into similarly-digested pTAB-TYDV-Rep to replace the original CaMV 35S promoter. This construct is designated pAR-TYDV-Rep.

Primers:

```
ARSK-F
                                       [SEQ ID NO: 57]
5'-CCATGGATCTCATTCTCCTTCAACAAGGCG-3'

ARSK-R
                                       [SEQ ID NO: 58]
5'-CCATGGTTTCAACTTCTTCTTTTGTGTTATTTG-3'
```

(d) Wound-Inducible Expression

The 2032 by *Asparagus officinalis* PR gene (AoPR1) promoter (Genbank Accession: A26573) has been shown to direct strong reporter gene expression in wounded and actively dividing cell types such as, for example, callus (Firek et al., 1993). The AoPR1 promoter is amplified from *A. officinalis* gDNA by PCR using primers AoPR-F and AoPR-R. The resulting PCR product is cloned into pGEM-T and the sequence verified. The AoPR1 promoter is excised from pGEM-T by NcoI digestion and ligated into similarly digested pTAB-TYDV-Rep to replace the original CaMV 35S promoter. This construct is designated pAo-TYDV-Rep.

Primers:

```
AoPR-F
5'-GAATTCAGGGGTAAGTTTGCAAATATC-3'    [SEQ ID NO: 59]

AoPR-R
5'-CGAGGTTGTGCCAGTCGAGCATTGCC-3'     [SEQ ID NO: 60]
```

(e) Alcohol-Inducible Expression

The ALC switch, derived from *Aspergillus nidulans*, is an alcohol-inducible promoter system based on the AlcA promoter and AlcR receptor. The ALC switch has been shown to function in plant systems using a uidA reporter gene model (Caddick et al., 1998). The plasmid pSRNAGS (BTI, Cornell University, Ithaca, N.Y.) contains a CaMV 35S pro-AlcR gene-nos ter and AlcA pro-uidA reporter gene-CaMV 35S ter cassette in pBIN16. The CaMV 35S pro-AlcR gene-nos ter-AlcA pro cassette is amplified from pSRNAGS by PCR using primers 35S-IE (SEQ ID NO:21) and Alc-R (SEQ ID NO:61). The PCR product is cloned into pGEM-T and sequence verified. The insert is then excised by NcoI digestion and ligated into similarly-digested pTAB-TYDV-Rep to replace the original CaMV 35S promoter. This construct is designated pAlc-TYDV-Rep.

Primer:

```
Alc-R
                                       [SEQ ID NO: 61]
5'-CCATGGTTTGAGGCGAGGTGATAGGATTGG-3'
```

Each of the binary TYDV Rep-containing plasmids are introduced into *Agrobacterium tumefaciens* (LBA4404) by electroporation using the method of Singh et al. (1993).

(f) Tissue-Specific and Inducible Rep Expression Directs Reporter Gene Activation in Precise Tissue Types Leaves from tobacco plants transformed with the plasmid pTEST4 are super-infected with *Agrobacterium* harbouring the plasmids pTAB-TYDV-Rep, pGL-TYDV-Rep, pAR-TYDV-Rep, pAo-TYDV-Rep, and pAlc-TYDV-Rep using the method of Horsch et al. (1988). In this case, selection of transformed tobacco plants is achieved using the herbicide phosphoinothricin ammonium (PPT). Transgenic plants are confirmed to contain the TYDV Rep gene by PCR using the primers TYDV.RepF and TYDV.RepR. Ten independent transformants for each plasmid are selected for further studies. Plants are grown to maturity, allowed to flower and seed collected. Different plant organs from independent transformants, including leaves, stems, roots, flower, and seed, are collected and GUS activity detected using histochemical assays.

Tobacco plants super-transformed with the plasmid pTAB-TYDV-Rep display strong GUS expression throughout all plant parts tested. The level of GUS expression in these plants is considerably higher than plants transformed with the non-replicating control, pTAB16.

In contrast, plants super-transformed with the plasmid pGL-TYDV-Rep show strong GUS expression in the seeds only, plants super-transformed with the plasmid pAR-TYDV-Rep show strong GUS expression in the roots only, plants super-transformed with the plasmid pAo-TYDV-Rep show strong GUS expression in wounded and meristematic cells, and plants super-transformed with the plasmid pAlc-TYDV-Rep show strong constitutive GUS expression when drenched in a 1% v/v ethanol solution only.

Rep-assisted nicking, joining and replication of the GUS expression cassette is confirmed (as described previously) in all tissue types of tobacco plants super-transformed with the plasmid pTAB-TYDV-Rep. In contrast, this activity is only detected in the seeds of plants super-transformed with the plasmid pGL-TYDV-Rep, in the roots of plants super-transformed with the plasmid pAR-TYDV-Rep, at the site of wounding in plants super-transformed with the plasmid pAo-TYDV-Rep, and constitutively in ethanol-induced plants super-transformed with the plasmid pAlc-TYDV-Rep. This result suggests tissue-specific or induced expression of the TYDV Rep gene confers high-level expression from the Rep-activatable GUS cassette in those tissue types only.

Example 11

MV p50 and hrmA Gene Mediated Resistance

Based on TYDV (a) TYDV Rep-Activated Expression of the TMV p50 Helicase Fragment Induces Systemic Acquired Resistance (SAR) in Tobacco Previous studies (Erickson et al., 1999) have demonstrated that non-viral expression of the 50 kDa tobacco mosaic virus (TMV) helicase fragment (p50) is sufficient to induce the N-mediated hypersensitive response (HR) in suitable tobacco varieties (e.g. *Nicotiana tabacum* cv. "Petite Havana" SR1 homozygous for the N gene). The defense response is characterised by cell death at the site of virus infection and induction of the systemic acquired resistance (SAR) pathway with resulting inhibition of viral replication and movement.

The p50 gene fragment is amplified by PCR using primers p50-F and p50-R from cloned genomic TMV DNA (Plant Gene Expression Centre, University of California, USA). The PCR product is cloned into pGEM-T and the sequence verified. The catalase intron containing the TYDV LIR from pTEST3 (FIG. 10) is engineered in frame into the unique EcoRI site in the p50 coding region. This plasmid is designated pGEM50-LIR. A pUC-based Rep-activatable p50 gene plasmid is subsequently constructed, as described for pTEST3 in Example 2, above. The cassette is inserted into pART27, as was described for pTEST4. The resulting p50 Rep-activatable binary plasmid is designated pSAR1. The plasmid pSAR1 is used to transform *Agrobacterium* as previously described.

Primers:

```
p50-F
                                    [SEQ ID NO: 62]
5'-CCATGGAGATAGAGTCTTTAGAGCAGTTTC-3' p50-R
                                    [SEQ ID NO: 63]
5'-GGATCCTATTGTGTTCCTGCATCGACCTTA-3'
```

(b) Systemic Acquired Resistance to TYDV in Tobacco

Ten tobacco plants (*Nicotiana tabacum* cv. "Petite Havana" SR1 homozygous for the N gene) transformed with T-DNA from plasmid pSAR1 are obtained by *Agrobacterium*-mediated transformation and confirmed to contain the Rep-activatable cassette and NPTII gene by PCR as described above. Plants are infected with TYDV and observed for symptoms, as previously described. Tobacco plants transformed with the Rep-activatable, p50 gene display atypical hypersensitive necrosis at the site of aphid feeding, two days post infection. These plants develop normally over the ensuing 3 months, in comparison to infected non-transgenic tobacco plants, which display typical TYDV-induced symptoms.

TYDV genomic DNA is detected in inoculated non-transgenic tobacco but not in transgenic nor uninfected control lines, as previously described. This result suggests TYDV Rep-induced expression of the TMV p50 gene is sufficient to stimulate the N gene hypersensitive response in suitable tobacco cultivars and provide resistance to TYDV infection.

(c) Wound-Inducible TYDV Rep Expression Activates TMV p50 Gene Expression and Triggers SAR to a Variety of Pathogens.

Leaves from pSAR1-transformed tobacco plants are super-infected with *Agrobacterium* containing the plasmid pAo-TYDV-Rep (Example 10), as previously described. Ten super-transformed lines, confirmed to contain the wound-inducible Rep gene, are selected for further studies. Transgenic plants and suitable controls are subjected to infection with a variety of viral pathogens e.g. (1) aphid transmission of tobacco vein mottling virus, (ii) tobacco rattle virus via the nematode vector *Paratrichodorus pachydermus*, and (iii) biolistic introduction of an infectious BeYDV 1.1mer. Over time, plants are observed for characteristic viral-induced symptoms. All transgenic plants display atypical hypersensitive necrosis at the site of virus inoculation in comparison to controls.

(d) Wound-Inducible Expression of TYDV Rep Activates hrmA-Mediated Broad Range Pathogen Resistance in Tobacco The hrmA gene product from *Pseudomonas syringae* pv. *syringae* has been shown to activate pathogen related genes in a number of tobacco cultivars, and confer resistance to variety of pathogens, including viruses, fungi and bacteria (Shen et al., 2000).

The hrmA gene is amplified from a plasmid containing the coding sequence by PCR using primers hrm-F and hrm-R. A pUC-based Rep-activatable hrmA plasmid is subsequently constructed, as described in Example 2, above, for pTEST3. The cassette is inserted into pART27, as described for pTEST4. The resulting hrmA-activatable binary plasmid is designated pSAR2. The plasmid pSAR2 is used to transform *Agrobacterium*, as described.

```
hrm-F
                                         [SEQ ID NO: 64]
5'-CCATGGGCATGCACGCTTCTCCAGCGTAGAAGCG-3' hrm-R
                                         [SEQ ID NO: 65]
5'-GGATCCTCAGTTTCGCGCCCTGAGCGCCGG-3'
```

Ten tobacco plants (*Nicotiana tabacum*) transformed with T-DNA from plasmid pSAR2 are obtained by *Agrobacterium*-mediated transformation and confirmed to contain the Rep-activatable cassette and NPTII gene by PCR as previously described. Leaves from pSAR2 transformed tobacco plants are super-infected with *Agrobacterium* containing the plasmid pAo-TYDV-Rep, as previously described. Ten super-transformed lines, confirmed to contain the wound-inducible Rep gene, are selected for further studies. Transgenic plants and suitable controls are subjected to infection with a variety of pathogens e.g. tobacco vein mottling virus, tobacco etch virus, blank shank fungus *Phytophthora parasitica*, and wild fire bacterium *Pseudomonas syrinagae* pv. *tabaci*. Over time, plants are observed for characteristic pathogen-induced symptoms. All transgenic plants display atypical hypersensitive necrosis at the site of inoculation, in comparison to controls.

Example 12

Over Expression of Human Serum Albumin

Based on TYDV (a) Rep-Activated, Over-Expression of a Commercially Important Protein, Human Serum Albumin Albumin is a soluble, monomeric protein which comprises about one-half of the blood serum protein. Albumin functions primarily as a carrier protein for steroids, fatty acids, and thyroid hormones and plays a role in stabilizing extracellular fluid volume.

The 1831 by Human serum albumin (HSA) coding region (Lawn et al., 1981) is amplified from a plasmid containing the gene by PCR using primers Alb-F and Alb-R. A pUC-based Rep-activatable HSA plasmid is subsequently constructed, as described in Example 2, above, for pTEST3. The cassette is inserted into pART27, as described for pTEST4. The resulting HSA-activatable binary plasmid is designated pHSA1. The plasmid pHSA1 is used to transform *Agrobacterium*, as described.

Ten tobacco plants (*Nicotiana tabacum*) transformed with T-DNA from plasmid pHSA1 are obtained by *Agrobacterium*-mediated transformation and confirmed to contain the Rep-activatable cassette and NPTII gene by PCR, as described. Leaves from pHSA1 transformed tobacco plants are super-infected with *Agrobacterium* containing plasmids pTAB-TYDV-Rep, pGL-TYDV-Rep, pAo-TYDV-Rep, pAlc-TYDV-Rep, as described. Ten super-transformed lines from each transformation are confirmed to contain the Rep gene, and selected for further studies. Plants are grown to maturity and HSA content assessed using ELISA and antibodies raised to the HSA gene product. HSA protein, is detected at high levels but in different plant parts or under specific conditions; i.e. constitutively (pTAB-TYDV-Rep), seed only (pGL-TYDV-Rep), wounded tissues (pAo-TYDV-Rep) and constitutively in alcohol treated plants (pAlc-TYDV-Rep). A proposed model for Rep-activated expression of the human serum albumin gene from the plasmid pHSA1 is depicted in FIG. 26.

Primers:

```
Primers:
Alb-F
                                        [SEQ ID NO: 72]
5'-CCATGGAGATGAAGTGGGTAACCTTTATTTCC-3'

Alb-R
                                        [SEQ ID NO: 73]
5'-GGATCCTTATAAGCCTAAGGCAGCTTGACT-3'
```

Those skilled in, the art will appreciate that the invention described herein is susceptible to variations and modifications other than those specifically described. It is to be understood that the invention includes all such variations and modifications. The invention also includes all of the steps, features, compositions and compounds referred to or indicated in this specification, individually or collectively, and any and all combinations of any two or more of said steps or features.

BIBLIOGRAPHY

Altschul et al. (1997) *Nucl. Acids Res.* 25:3389. 1997.

An G (1985) High efficiency transformation of cultured tobacco cells. *Plant Physiology* 79: 568-570

Ausubel et al., "Current Protocols in Molecular Biology" John Wiley & Sons Inc, 1994-1998, Chapter 15.

Becker D K., Dugdale B, Smith M K, Harding R M, Dale J L (2000) Genetic transformation of Cavendish banana (*Musa* spp. AAA group) cv "Grand Nain" via microprojectile bombardment. *Plant Cell Reports* 19 (3): 229-234

Bonner and Laskey (1974) *Eur. J. Biochem.* 46: 83

Boulton M I (1995) *Agrobacterium*-mediated transfer of geminiviruses to plant tissues. *Methods in Molecular Biology* 49: 77-93.

Caddick M X, Greenland A J, Jepson I, Krause K P, Qu N, Riddell K V, Salter M G, Schuch W, Sonnewald U, Tomsett A B (1998) An ethanol inducible gene switch for plants used to manipulate carbon metabolism. *Nature Biotechnology* 16(2): 177-80

Chang S, Puryear J, Caimey J (1993) A simple and efficient method for isolating RNA from Pine trees. *Plant Molecular Biology Reporter* 11 (2): 113-116

Dugdale B, Beetham P R, Becker D K, Harding R M, Dale J L (1998) Promoter activity associated with the intergenic regions of banana bunchy top virus DNA-1 to -6 in transgenic tobacco and banana cells. *Journal of General Virology* 79 (10): 2301-11

Erickson F L, Holzberg S, Calderon-Urrea A, Handley V, Axtell M, Con. C, Baker B (1999) The helicase domain of the TMV replicase proteins induces the N-mediated defence response in tobacco. *Plant Journal* 18(1): 67-75

Firek S, Ozcan S, Warner S A, Draper J (1993) A wound-induced promoter driving npt-II expression limited to dedifferentiated cells at wound sites is sufficient to allow selection of transgenic shoots. *Plant Molecular Biology* 22(1): 129-42

Gleave A P (1992) A versatile binary vector system with a T-DNA organisational structure conducive to efficient integration of cloned DNA into the plant genome. *Plant Molecular Biology* 20(6): 1203-1207

Hill A V (1937) Yellow dwarf of tobacco in Australia: V. transmission by Orosius argentatus (Evans) to some alternative host plants. *Journal for Scientific and Industrial Research Australia* 10: 228-230

Horsch R B, Fry J, Hoffmann N, Neidermeyer I, Rogers S G, Fraley R T (1988) Leaf disc transformation. In *Plant*

*Molecular Biology Manual*, pp. A5/1-A5/9. Edited by S. B. Gelvin & R. A. Schilperoort. Dordrecht: Kluwer.

Hwang I, Goodman H M (1995) An *Arabidopsis thaliana* root-specific kinase homolog is induced by dehydration, ABA, and NaCl. *Plant Journal* 8(1):37-43

Jefferson R A (1987) Assaying chimeric plant genes: The GUS fusion system. *Plant Molecular Biology Reporter* 5: 381-405

Lawn R M, Adelman J, Bock S C, Franke A E, Houck C M, Najarian R C, Seeburg P H, Wion K L (1981) The sequence of human serum albumin cDNA and its expression in *E. coli*. *Nucleic Acids Research* 9(22): 6103-114

Leisy D J, Hnilo J, Zhao Y, Okita T W (1990) Expression of a rice glutelin promoter in transgenic tobacco. *Plant Molecular Biology* 14(1): 41-50

Marmur and Doty (1962) *J. Mol. Biol.* 5: 109

Miller J (2001) Expression of potential vaccines in plants. *PhD Thesis, Queensland University of Technology, Brisbane, Australia.*

Pietrzak M, Shillito R D, Hohn T, Potrykus I (1986) Expression in plants of two bacterial antibiotic resistance genes after protoplast transformation with a new plant expression vector. *Nucleic Acids Research* 14(14): 5857-5868

Shen S, Li Q, He S Y, Barker K R, Li D, Hunt AG (2000) Conversion of compatible plant-pathogen interactions into incompatible interactions by expression of the *Pseudomonas syringae* pv. *syringae* 61 hrmA gene in transgenic tobacco plants. *Plant Journal* 23(2): 205-13

Singh A, Kao T, Lin J J (1993) Transformation of *Agrobacterium tumefaciens* with T-DNA vector using high-voltage electroporation. *Focus* 15: 84-87

Southern (1975) Detection of specific sequences among DNA fragments separated by gel electrophoresis. *Journal of Molecular Biology* 98: 503-517

Stewart C N, Via L E (1993) A rapid CTAB DNA isolation technique for RAPD fingerprint and PCR applications. *Biotechniques* 14: 748-750

---

The invention claimed is:

1. A construct system comprising:
   (i) a first construct comprising in 5' to 3' linear form a first Rep protein recognition sequence recognizable by a geminivirus Rep protein, the 3' end of an intron, the 3' end portion of a gene of interest operably linked to a terminator, a promoter operably linked to the 5' end of the gene of interest, the 5' end of the intron and a second Rep protein recognition sequence recognizable by the geminivirus Rep protein; wherein the Rep recognition sequences are compatible with each other to promote circularization, wherein the 3' end and the 5' end intron sequences are capable of splicing; wherein the 3' end and 5' end portions of the gene of interest together constitute the coding region of the gene of interest; wherein upon circularization, the 3' end of the intron and the 5' end of the intron form an intronic sequence, and the 5' end portion of the gene of interest is separated from said 3' end portion of the gene of interest by the intronic sequence; wherein upon excision of the intronic sequence, the 5' end portion of the gene of interest is operably linked to the 3' end portion of the gene of interest; and wherein upon expression of the gene of interest, the gene of interest exhibits an activity or property or a capacity to exhibit an activity or property not present in the separate portions of the gene of interest prior to circularization of the construct and prior to excision of the intronic sequence; and
   (ii) a second construct comprising a nucleotide sequence encoding the geminivirus Rep protein operably linked to a promoter.

2. The construct system of claim 1, wherein the promoter is a regulatable promoter.

3. The construct system of claim 1, wherein the promoter is an inducible promoter.

4. The construct system of claim 3, wherein the inducible promoter is an alcohol inducible promoter.

5. The construct system of claim 1, wherein the promoter is a tissue-specific promoter.

6. The construct system of claim 5, wherein the tissue-specific promoter is a seed-specific promoter.

7. The construct system of claim 5, wherein the tissue-specific promoter is a root-specific promoter.

8. The construct system of claim 1, wherein the promoter is a wound-specific promoter.

* * * * *